US012668806B2

(12) United States Patent
Rothberg et al.

(10) Patent No.: US 12,668,806 B2
(45) Date of Patent: Jun. 30, 2026

(54) GENETICALLY ENGINEERED VEGETABLES

(71) Applicant: Impossible Vines Inc., Miami Beach, FL (US)

(72) Inventors: Gabriella Rothberg, Miami Beach, FL (US); Jonathan M. Rothberg, Miami Beach, FL (US)

(73) Assignee: Impossible Vines Inc., Miami Beach, FL (US)

( * ) Notice: Subject to any disclaimer, the term of this patent is extended or adjusted under 35 U.S.C. 154(b) by 0 days.

(21) Appl. No.: 19/376,424

(22) Filed: Oct. 31, 2025

(65) Prior Publication Data

US 2026/0125693 A1     May 7, 2026

Related U.S. Application Data

(60) Provisional application No. 63/715,207, filed on Nov. 1, 2024.

(51) Int. Cl.
| | |
|---|---|
| *C12N 15/82* | (2006.01) |
| *C07K 14/32* | (2006.01) |
| *C07K 14/415* | (2006.01) |

(52) U.S. Cl.
CPC .......... *C12N 15/8205* (2013.01); *C07K 14/32* (2013.01); *C07K 14/415* (2013.01); *C12N 15/8209* (2013.01); *C12N 15/8257* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 6,031,155 A * | 2/2000 | Cameron-Mills .... | C12N 9/2482 435/69.7 |
| 9,896,696 B2 * | 2/2018 | Begemann ........... | C12N 15/102 |
| 11,732,268 B2 * | 8/2023 | Krieger .............. | C12N 15/8213 435/469 |

FOREIGN PATENT DOCUMENTS

| | | | | |
|---|---|---|---|---|
| CN | 110923262 A * | 3/2020 | ........... | C12N 9/2414 |
| WO | WO-2008107509 A1 * | 9/2008 | ......... | C12N 15/8289 |

| | | | | |
|---|---|---|---|---|
| WO | WO-2014187311 A1 * | 11/2014 | ........ | C12N 15/8289 |
| WO | WO-2023036984 A1 * | 3/2023 | ......... | C12N 15/8281 |
| WO | WO-2024026348 A1 * | 2/2024 | ........... | C07K 14/805 |
| WO | WO-2024064694 A2 * | 3/2024 | ......... | C12N 15/8282 |

OTHER PUBLICATIONS

Roque, E., Gómez, M. D., Ellul, P., Wallbraun, M., Madueno, F., Beltrán, J. P., & Canas, L. A. (2007). The PsEND1 promoter: a novel tool to produce genetically engineered male-sterile plants by early anther ablation. Plant Cell Reports, 26(3), 313-325. (Year: 2007).*
Parvathy, S. T., Udayasuriyan, V., & Bhadana, V. (2022). Codon usage bias. Molecular biology reports, 49(1), 539-565. (Year: 2022).*
Gisbert, C., Timoneda, A., Porcel, R., Ros, R., & Mulet, J. M. (2020). Overexpression of BvHb2, a class 2 non-symbiotic hemoglobin from sugar beet, confers drought-induced withering resistance and alters iron content in tomato. Agronomy, 10(11), 1754. (Year: 2020).*
Coale et al., Nitrogen-fixing organelle in a marine alga. Science. Apr. 12, 2024;384(6692):217-222. doi: 10.1126/science.adk1075. Epub Apr. 11, 2024. with supplemental materials.

* cited by examiner

*Primary Examiner* — Charles Logsdon
*Assistant Examiner* — Jessica Nicole Stockdale
(74) *Attorney, Agent, or Firm* — Wolf, Greenfield & Sacks, P.C.

(57) ABSTRACT

The present disclosure relates at least in part to genetic engineering of vegetable (e.g., tomato) plants to, for example, produce heme, a molecule contributing to a meat-like flavor, and to the incorporation of male sterility in these plants to facilitate the production of F1 hybrid seeds. Described herein, in some embodiments, are methods for constructing and introducing into such plants genetic constructs containing both a heme gene and a male sterility gene, the resulting plants, and the use of these plants in hybrid seed production. The present disclosure also provides at least in part methods for enhancing lycopene content in plants, such as tomato plants, either through genetic modification or selective breeding. While introducing key genes like Psy is effective, adding multiple genes or knocking out competing pathways can lead to more substantial increases in lycopene levels. Enhanced lycopene content can provide added health benefits, including potential cancer protection, making these plants, such as tomatoes, particularly valuable in the context of functional foods. The plants may be of varieties with high lycopene content combined with genetic modifications as provided herein. The present disclosure offers a comprehensive solution for producing plants (e.g., tomatoes) with increased nutritional value.

10 Claims, 8 Drawing Sheets

Specification includes a Sequence Listing.

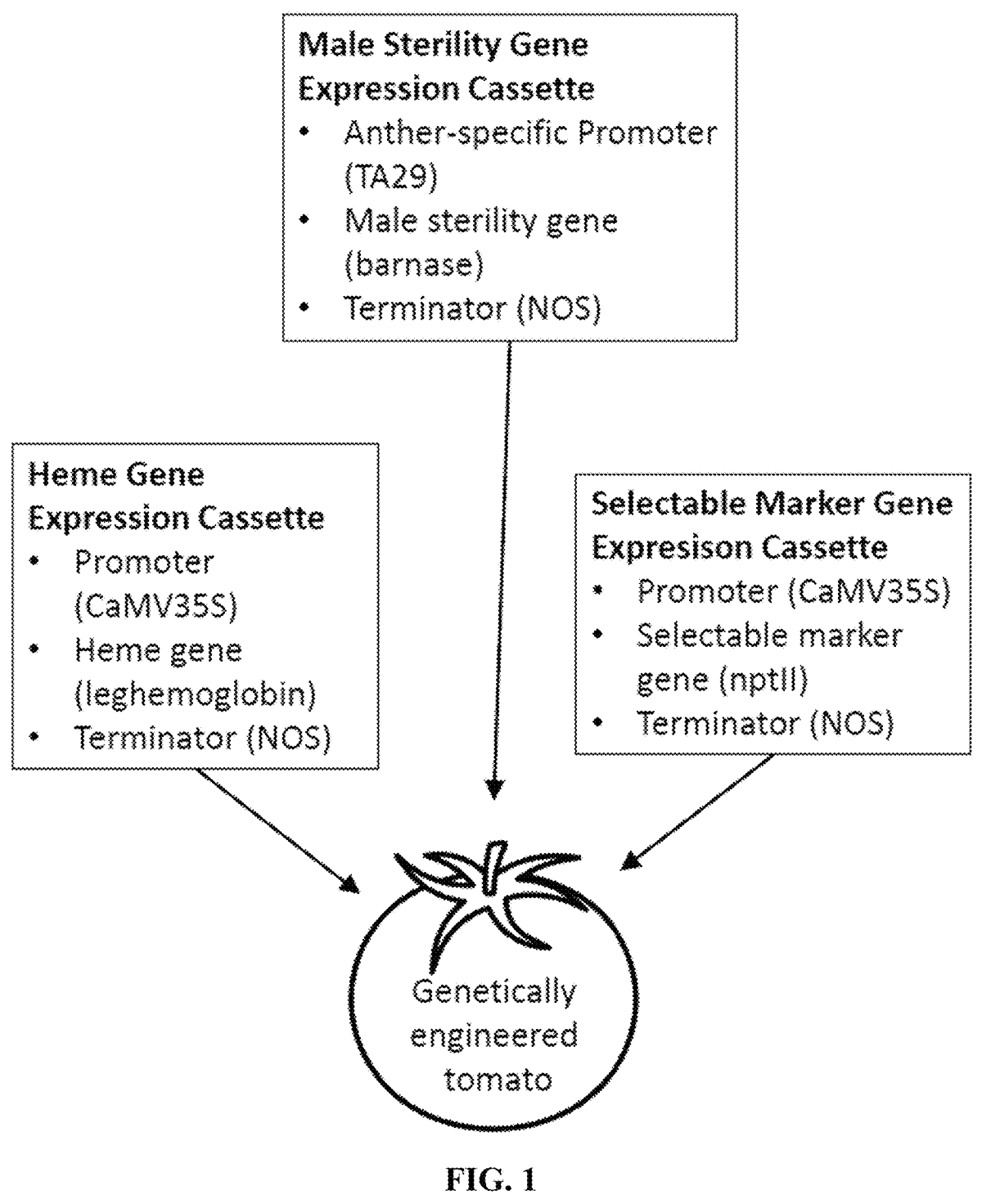

Male Sterility Gene Expression Cassette
* Anther-specific Promoter (TA29)
* Male sterility gene (barnase)
* Terminator (NOS)

Heme Gene Expression Cassette
* Promoter (CaMV35S)
* Heme gene (leghemoglobin)
* Terminator (NOS)

Selectable Marker Gene Expresison Cassette
* Promoter (CaMV35S)
* Selectable marker gene (nptII)
* Terminator (NOS)

Genetically engineered tomato

FIG. 1

GENETICALLY ENGINEERED VEGETABLES

CROSS REFERENCE TO RELATED APPLICATIONS

This application claims the benefit of priority under 35 U.S.C. § 119 (e) to U.S. Provisional Application No. 63/715, 207, filed Nov. 1, 2024, the entire contents of which are herein incorporated by reference.

REFERENCE TO AN ELECTRONIC SEQUENCE LISTING

The contents of the electronic sequence listing (1063470000US02-SEQ-KVC.xml; Size: 77,300 bytes; and Date of Creation: Oct. 31, 2025) are herein incorporated by reference in their entirety.

FIELD

The present disclosure generally relates, at least in part, to the field of plant biotechnology and genetic engineering. More specifically, it relates to the production of genetically engineered vegetable plants, such as tomato (*Solanum lycopersicum*) plants and eggplant (*Solanum melongena*) plants, engineered to express a protein to enhance iron content and contribute to a meat-like flavor, optionally combined with a male sterility gene to facilitate F1 hybrid seed production. The present disclosure also relates to increasing lycopene production, such as in tomato plants, to, in some embodiments, enhance its health benefits and antioxidant properties.

SUMMARY

Vegetables are widely recognized for their nutritional and health benefits, and the global demand for plant-based foods has continued to increase in response to growing consumer interest in sustainability and wellness. Tomatoes are among the most extensively cultivated vegetables and serve as an important dietary source of vitamins and antioxidants. In particular, the naturally occurring carotenoid, lycopene, imparts the characteristic red color and has health-promoting properties, including potential roles in reducing cancer risk and supporting cardiovascular and skin health. Iron and associated carrier molecules, such as heme, contribute to the characteristic meat-like flavor of many foods. The iron content in tomatoes, however, is inherently low, limiting their contribution to dietary iron intake.

Advances in plant genetic engineering can enable the precise enhancement of nutritional and sensory compounds in crops, offering an efficient and sustainable means to improve food quality, reduce agricultural inputs, and align with global trends towards plant-based diets. Accordingly, developing genetically improved tomato plant varieties that exhibit enhanced lycopene accumulation and/or elevated iron levels provides a promising opportunity to deliver greater nutritional benefits to the world's expanding population.

Aspects of the present disclosure relate, at least in part, to genetically engineered plants (e.g., vegetable plants such as tomato plants and eggplant plants) that can exhibit enhanced nutritional and/or sensory properties through the introduction of genes coding for heme production and, optionally, male sterility to enable controlled F1 hybrid seed production. The present disclosure further encompasses strategies for enhancing lycopene biosynthesis through genetic modification to yield plants (e.g., vegetable plants such as tomato plants) that can produce fruit (e.g., tomatoes) with improved antioxidant capacity.

Aspects of the present disclosure further provide genetically engineered vegetable plants that combine enhanced nutritional composition with improved hybridization efficiency. In some embodiments, the present disclosure relates to tomatoes or eggplants engineered to express a protein to produce heme, an iron-carrier molecule contributing to a meat-like flavor, while also introducing a male-sterility gene to facilitate efficient and controlled F1 hybrid seeds. The integration of these two traits enables the development of hybrid tomato or eggplant varieties that deliver desirable flavors without the need for manual emasculation during breeding.

Aspects of the present disclosure provides methods for enhancing lycopene biosynthesis in vegetable fruit, such as tomato fruit, through the overexpression of key enzymes involved in its biosynthesis, such as phytoene synthase (Psy). In some embodiments, the present disclosure relates to the use of gene-editing technologies, such as CRISPR/Cas9-mediated technology, to downregulate competing pathways, thereby reducing precursor flux toward lycopene production and achieving elevated antioxidant content.

The present disclosure thus can integrate flavor enhancement, nutritional fortification, and reproductive control into a single transgenic platform. This combination allows for sustainable, high-value vegetable cultivation that aligns with consumer demands for nutritious, plant-based foods, with improved sensory traits such as meatier tastes. Furthermore, the present disclosure provides the corresponding genetic constructs, transformation methods, and resulting plants, seeds, and fruits produced thereby.

Accordingly, aspects of the present disclosure relate to a genetic construct or set of genetic constructs comprising a first promoter operably linked to a first coding sequence and, optionally, a second promoter operably linked to a second coding sequence, wherein the first coding sequence encodes a heme-producing gene, and wherein the second coding sequence encodes a male-sterility gene. In some embodiments of any one of the compositions or methods provided herein, the first and second promoter are the same promoter or are different promoters that can result in the expression of the first and second coding sequence.

In some embodiments of any one of the compositions or methods provided herein, the genetic construct or set of genetic constructs comprises any one of the nucleotide sequences provided herein, such as a nucleotide sequence that is at least 70%, at least 75%, at least 80%, at least 85%, at least 90%, at least 95%, or at least 98% identical to SEQ ID NO: 3. In some embodiments of any one of the compositions or methods provided herein, the genetic construct or set of genetic constructs comprises the nucleotide sequence of SEQ ID NO: 3.

In some embodiments of any one of the compositions or methods provided herein, the genetic construct or set of genetic constructs comprises a nucleotide sequence that is at least 70%, at least 75%, at least 80%, at least 85%, at least 90%, at least 95%, or at least 98% identical to SEQ ID NO: 4. In some embodiments of any one of the compositions or methods provided herein, the genetic construct or set of genetic constructs comprises the nucleotide sequence of SEQ ID NO: 4.

In some embodiments of any one of the compositions or methods provided herein, the heme-producing gene is any one of the heme-producing genes provided herein, such as a leghemoglobin gene derived from *Glycine max*. In some embodiments of any one of the compositions or methods provided herein, a leghemoglobin gene comprises a nucleotide sequence that is at least 70%, at least 75%, at least 80%, at least 85%, at least 90%, at least 95%, or at least 98% identical to SEQ ID NO: 5. In some embodiments of any one of the compositions or methods provided herein, a leghemoglobin gene comprises the nucleotide sequence of SEQ ID NO: 5.

In some embodiments of any one of the compositions or methods provided herein, the male-sterility gene is any one of the male-sterility genes provided herein, such as a barnase gene derived from *Bacillus amyloliquefaciens.* In some embodiments of any one of the compositions or methods provided herein, a barnase gene comprises a nucleotide sequence that is at least 70%, at least 75%, at least 80%, at least 85%, at least 90%, at least 95%, or at least 98% identical to SEQ ID NO: 6. In some embodiments of any one of the compositions or methods provided herein, a barnase gene comprises the nucleotide sequence of SEQ ID NO: 6.

In some embodiments of any one of the compositions or methods provided herein, the first and/or second promoter is any one of the promoters provided herein. In some embodiments of any one of the compositions or methods provided herein, the first promoter is a constitutive promoter. In some embodiments of any one of the compositions or methods provided herein, the second promoter is a constitutive promoter. In some embodiments of any one of the compositions or methods provided herein, the constitutive promoter comprises a nucleotide sequence that is at least 70%, at least 75%, at least 80%, at least 85%, at least 90%, at least 95%, or at least 98% identical to SEQ ID NO: 9. In some embodiments of any one of the compositions or methods provided herein, the constitutive promoter comprises the nucleotide sequence of SEQ ID NO: 9.

In some embodiments of any one of the compositions or methods provided herein, the first promoter is a plant promoter. In some embodiments of any one of the compositions or methods provided herein, the first promoter is a plant-specific promoter. In some embodiments of any one of the compositions or methods provided herein, the first promoter is a fruit-specific promoter. In some embodiments of any one of the compositions or methods provided herein, the first promoter comprises a nucleotide sequence that is at least 70%, at least 75%, at least 80%, at least 85%, at least 90%, at least 95%, or at least 98% identical to SEQ ID NO: 10. In some embodiments of any one of the compositions or methods provided herein, the first promoter comprises the nucleotide sequence of SEQ ID NO: 10. In some embodiments of any one of the compositions or methods provided herein, the first promoter comprises a nucleotide sequence that is at least 70%, at least 75%, at least 80%, at least 85%, at least 90%, at least 95%, or at least 98% identical to SEQ ID NO: 11. In some embodiments of any one of the compositions or methods provided herein, the first promoter comprises the nucleotide sequence of SEQ ID NO: 11. In some embodiments of any one of the compositions or methods provided herein, the first promoter comprises a nucleotide sequence that is at least 70%, at least 75%, at least 80%, at least 85%, at least 90%, at least 95%, or at least 98% identical to SEQ ID NO: 12. In some embodiments of any one of the compositions or methods provided herein, the first promoter comprises the nucleotide sequence of SEQ ID NO: 12. In some embodiments of any one of the compositions or methods provided herein, the first promoter and/or the second promoter is a plant promoter. In some embodiments of any one of the compositions or methods provided herein, the plant promoter comprises the nucleotide sequence of any one of SEQ ID NOs: 10-12.

In some embodiments of any one of the compositions or methods provided herein, the first promoter and the second promoter are the same. In some embodiments of any one of the compositions or methods provided herein, the first promoter and the second promoter are different. In some embodiments of any one of the compositions or methods provided herein, the promoter controls expression of one or more genes. In some embodiments of any one of the compositions or methods provided herein, the promoter controls expression of two genes. In some embodiments of any one of the compositions or methods provided herein, the first and second promoter are the same single promoter in the genetic construct or set of genetic constructs.

In some embodiments of any one of the compositions or methods provided herein, the genetic construct or set of genetic constructs further comprises a terminator sequence. In some embodiments of any one of the compositions or methods provided herein, the terminator sequence is any one of such sequences provided herein. In some embodiments of any one of the compositions or methods provided herein, the terminator sequence comprises the nucleotide sequence of SEQ ID NO: 13 or SEQ ID NO: 14. In some embodiments of any one of the compositions or methods provided herein, the terminator sequence comprises a nucleotide sequence that is at least 70%, at least 75%, at least 80%, at least 85%, at least 90%, at least 95%, or at least 98% identical to SEQ ID NO: 13. In some embodiments of any one of the compositions or methods provided herein, the terminator sequence comprises the nucleotide sequence of SEQ ID NO: 13. In some embodiments of any one of the compositions or methods provided herein, the terminator sequence comprises a nucleotide sequence that is at least 70%, at least 75%, at least 80%, at least 85%, at least 90%, at least 95%, or at least 98% identical to SEQ ID NO: 14. In some embodiments of any one of the compositions or methods provided herein, the terminator sequence comprises the nucleotide sequence of SEQ ID NO: 14.

In some embodiments of any one of the compositions or methods provided herein, the genetic construct or set of genetic constructs further comprises a selectable marker gene and/or reporter gene and/or an antibiotic resistance gene. In some embodiments of any one of the compositions or methods provided herein, the selectable marker gene and/or reporter gene and/or antibiotic resistance gene is any one such genes provided herein. In some embodiments of any one of the compositions or methods provided herein, the antibiotic resistance gene is a hygromycin resistance gene. In some embodiments of any one of the compositions or methods provided herein, the hygromycin resistance gene comprises a nucleotide sequence that is at least 70%, at least 75%, at least 80%, at least 85%, at least 90%, at least 95%, or at least 98% identical to SEQ ID NO: 7. In some embodiments of any one of the compositions or methods provided herein, the hygromycin resistance gene comprises the nucleotide sequence of SEQ ID NO: 7.

In some embodiments of any one of the compositions or methods provided herein, the genetic construct or set of genetic constructs further comprises a first flanking sequence and/or a second flanking sequence. In some embodiments of any one of the compositions or methods provided herein, the first flanking sequence and/or a second flanking sequence is any one of such sequences provided herein. In some embodiments of any one of the compositions or methods provided herein, the first flanking sequence comprises the nucleotide sequence of SEQ ID NO: 15. In some embodiments of any one of the compositions or methods provided herein, the second flanking sequence comprises the nucleotide sequence of SEQ ID NO: 16. In some embodiments of any one of the compositions or methods provided herein, the first flanking sequence comprises a nucleotide sequence that is at least 70%, at least 75%, at least 80%, at least 85%, at least 90%, at least 95%, or at least 98% identical to SEQ ID NO: 15. In some embodiments of any one of the compositions or methods provided herein, the first flanking sequence comprises the nucleotide sequence of SEQ ID NO: 15. In some embodiments of any one of the compositions or methods provided herein, the second flanking sequence comprises a nucleotide sequence that is at least 70%, at least 75%, at least 80%, at least 85%, at least 90%, at least 95%, or at least 98% identical to SEQ ID NO: 16. In some embodiments of any one of the compositions or methods provided herein, the second flanking sequence comprises the nucleotide sequence of SEQ ID NO: 16.

Aspects of the present disclosure relate to a genetic construct or set of genetic constructs comprising a first promoter (e.g., fruit specific promoter such as the E8 promoter) operably linked to a first coding sequence, wherein the first coding sequence encodes a phytoene synthase (Psy) gene. In some embodiments of any one of the compositions or methods provided herein, in addition to the genetic construct or set of genetic constructs also comprised are means for knocking out genes that compete with the lycopene biosynthesis pathway, such as any one of the gene editing systems provided herein or any one or more or combination of components thereof. Aspects of the present disclosure relate to a plant cell (e.g., vegetable plant cell) comprising any genetic construct or set of genetic constructs provided herein. In some embodiments of any one of the compositions or methods provided herein, the plant cell is tomato plant cell or an eggplant plant cell. In some embodiments of any one of the compositions or methods provided herein, the plant or plant cell is of a variety with a naturally elevated lycopene content such as Tangerine, Double Rich, or Health Kick.

Aspects of the present disclosure relate to a method, the method comprising transforming a plant cell (e.g., vegetable plant cell) with any genetic construct or set of genetic constructs provided herein. In some embodiments of any one of the compositions or methods provided herein, transforming is via any one of such methods provided herein such as via Agrobacterium-mediated transformation. In some embodiments of any one of the compositions or methods provided herein, the plant cell is tomato plant cell or an eggplant plant cell.

Aspects of the present disclosure relate to a method of producing a genetically engineered plant (e.g., vegetable plant), the method comprising introducing into a plant any genetic construct or set of genetic constructs provided herein. In some embodiments of any one of the methods provided herein, the introducing is via any one of such methods provided herein, such as via Agrobacterium-mediated transformation. In some embodiments of any one of the compositions or methods provided herein, the genetically engineered plant is a tomato plant or an eggplant plant.

Aspects of the present disclosure relate to a method of producing an F1 hybrid vegetable plant (e.g., tomato plant or eggplant plant), the method comprising: crossing any genetically engineered plant described herein with a male-fertile vegetable plant (e.g., tomato plant or eggplant plant) to produce a crossed plant; harvesting seeds from the crossed plant; and growing the F1 hybrid tomato plant from the seeds.

BRIEF DESCRIPTION OF THE DRAWINGS

The following drawings form part of the present specification and are included to further demonstrate certain aspects of the present disclosure, which may be better understood by reference to one or more of these drawings in combination with the detailed description of specific embodiments presented in this disclosure. The accompanying drawings are not intended to be drawn to scale. The drawings are illustrative only and are not required for enablement of the disclosure. For purposes of clarity, not every component may be labeled in every drawing. In the drawings:

FIG. 1 is a block diagram illustrating elements of a system according to embodiments of the present disclosure.

DETAILED DESCRIPTION

Figure 2:
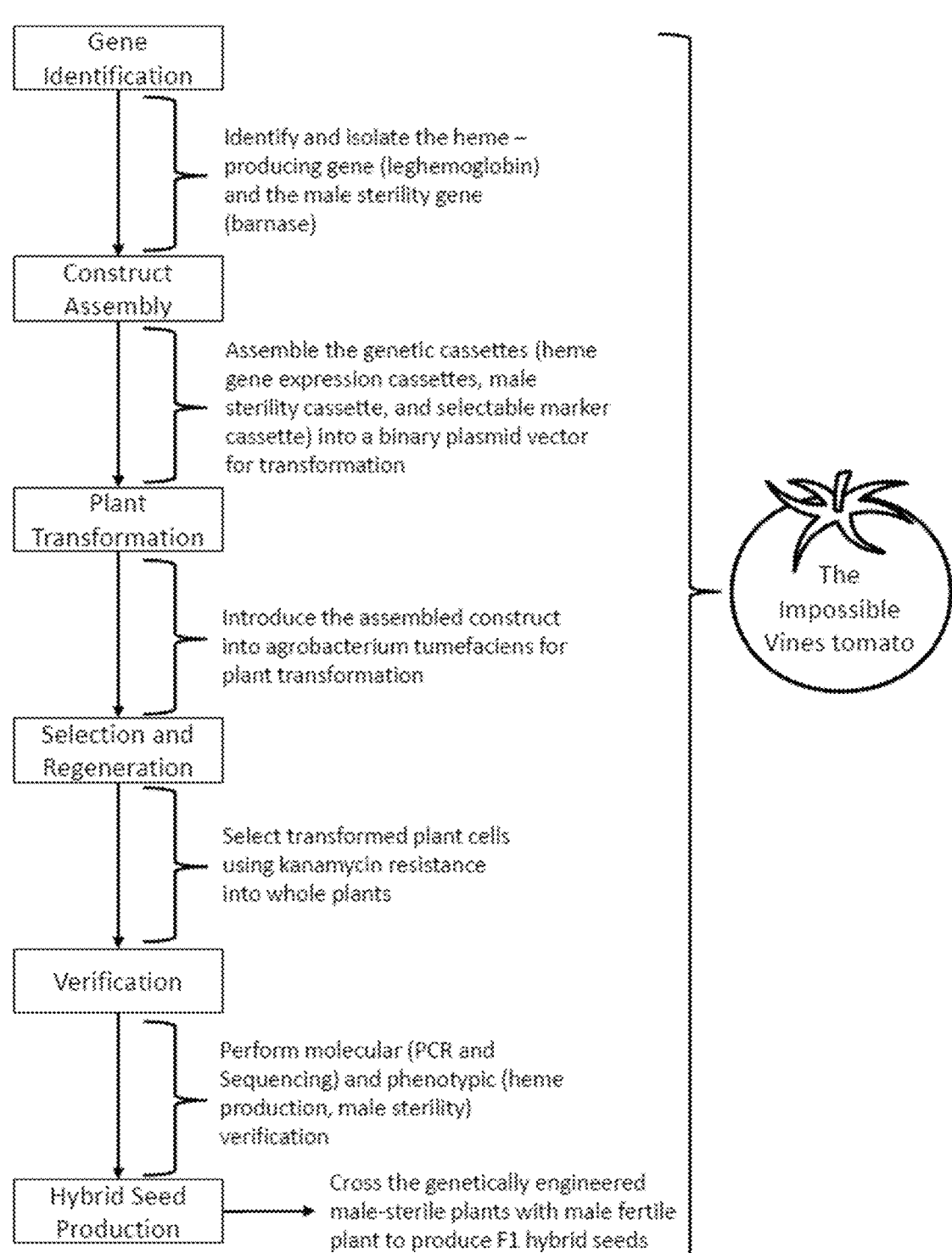
FIG. 2 is a flow diagram illustrating steps of an engineering process according to embodiments of the present disclosure.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes. Such incorporation by reference is not intended to be an admission that any of the incorporated publications, patents and patent applications cited herein constitute prior art.

As used in this specification and the appended claims, the singular forms "a," "an" and "the" include plural referents unless the content clearly dictates otherwise. For example, reference to "a molecule" includes a mixture of two or more such molecules or a plurality of such molecules, and the like.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, elements, characteristics, properties, method/process steps or limitations) but not the exclusion of any other integer or group of integers. Thus, as used herein, the term "comprising" is inclusive and does not exclude additional, unrecited integers or method/process steps. In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/ process step or limitation) or group of integers (e.g. features, elements, characteristics, properties, method/process steps or limitations) alone.

The following description is provided to enable any person skilled in the art of plant biotechnology to make and use the invention of the present disclosure and sets forth the best modes contemplated by the inventors for carrying out the invention of the present disclosure. It is understood that variations in the described embodiments may be made without departing from the scope of the present disclosure.

Accordingly, aspects of the present disclosure relate to a genetically engineered vegetable plant that (i) produces heme, contributing to a meat-like flavor, and is (ii) male-sterile, facilitating the production of F1 hybrid seeds (FIG. 1). Aspects of the present disclosure also relate to a genetic construct or set of genetic constructs comprising a heme gene expression cassette, including a promoter, the leghemoglobin gene (or a functional homolog or equivalent), and a terminator; a male sterility gene expression cassette, including an anther-specific promoter, the barnase gene (or a functional homolog or equivalent), and a terminator; and, optionally, a selectable marker and/or reporter and/or antibiotic resistance gene expression cassette.

Further aspects of the present disclosure relate to a method for producing transgenic plants (e.g., vegetable plants) by Agrobacterium-mediated transformation using cotyledons, followed by selection, shoot regeneration, and genomic validation of the desired traits. FIG. 2 is a flow diagram illustrating steps of an engineering process according to an embodiment of the present disclosure.

Further aspects of the present disclosure relate to a method for increasing lycopene content in tomatoes through upregulation of the biosynthesis pathway, under a fruit-specific promoter, and synergistic downregulation of competing pathways.

Further aspects of the present disclosure relate to use of male sterile plants (e.g., vegetable plants such as tomato plants or eggplant plants) as Parental Line A in controlled cross-pollination with male-fertile Parental Line B to produce F1 hybrid seeds exhibiting the described genetically modified traits.

Further aspects of the present disclosure relate to F1 hybrid plants (e.g., vegetable plants such as tomato plants or eggplant plants) and fruits produced by the foregoing methods, characterized by enhanced lycopene accumulation, increased heme and iron levels, desirable flavor attributes, and/or overall improved nutritional value.

Genetic Constructs

Figure 3:
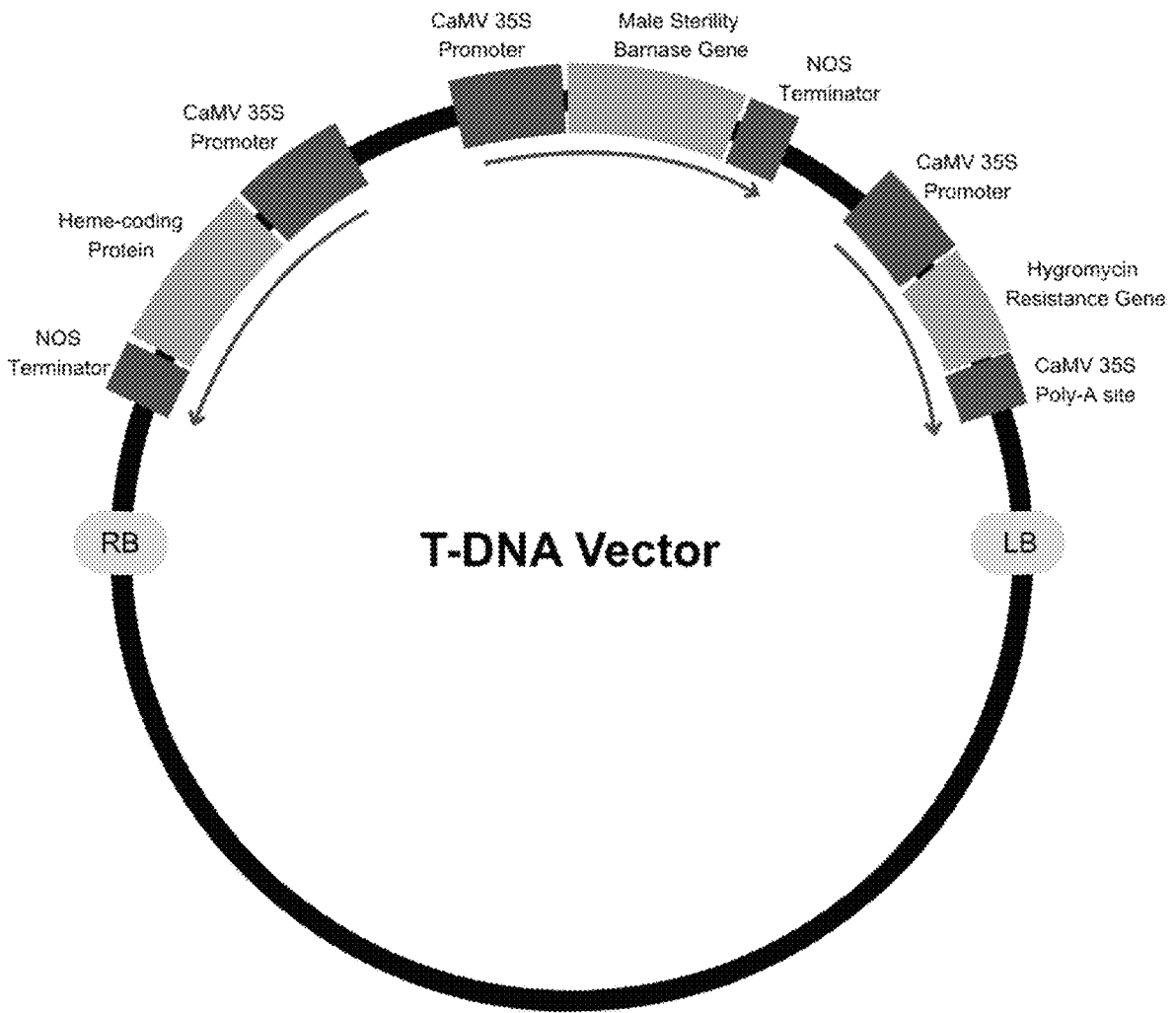
FIG. 3 is a plasmid map depicting an exemplary dual-cassette genetic construct comprising an expression cassette encoding the heme protein under the control of a constitutive promoter and an expression cassette encoding the barnase gene under an anther-specific promoter.

Aspects of the present disclosure relate to genetic constructs useful for expressing one or more genes in a plant (i.e., a genetically engineered plant). The term "genetic construct," as used herein, includes synthetic deoxyribonucleic acid (DNA) molecules that contain specific genetic information intended for manipulation or expression in a target organism. Genetic constructs typically include several components, such as coding sequences (genes), promoters, enhancers and regulatory elements, selectable markers, and terminator sequences. A non-limiting example of a genetic construct described herein is shown in FIG. 3. In an embodiment, the genetic constructs are vectors such as for introducing the one or more genes into a plant or plant cell as provided herein. The term "vector," as used herein, includes DNA molecules used to carry foreign genetic material into another cell, serving as a vehicle for delivering DNA. In some embodiments, a genetic construct is a plasmid. The term "plasmid," as used herein, includes small, circular DNA molecules used to introduce specific genes into host cells.

In some embodiments, a genetic construct of the present disclosure delivers a single gene to a cell. In some embodiments, a genetic construct of the present disclosure delivers two or more genes to a cell. In some embodiments, a genetic construct of the present disclosure is a dual-gene genetic construct.

In some embodiments, a set of genetic constructs of the present disclosure delivers two or more genes to a cell.

Vectors

Figure 4:
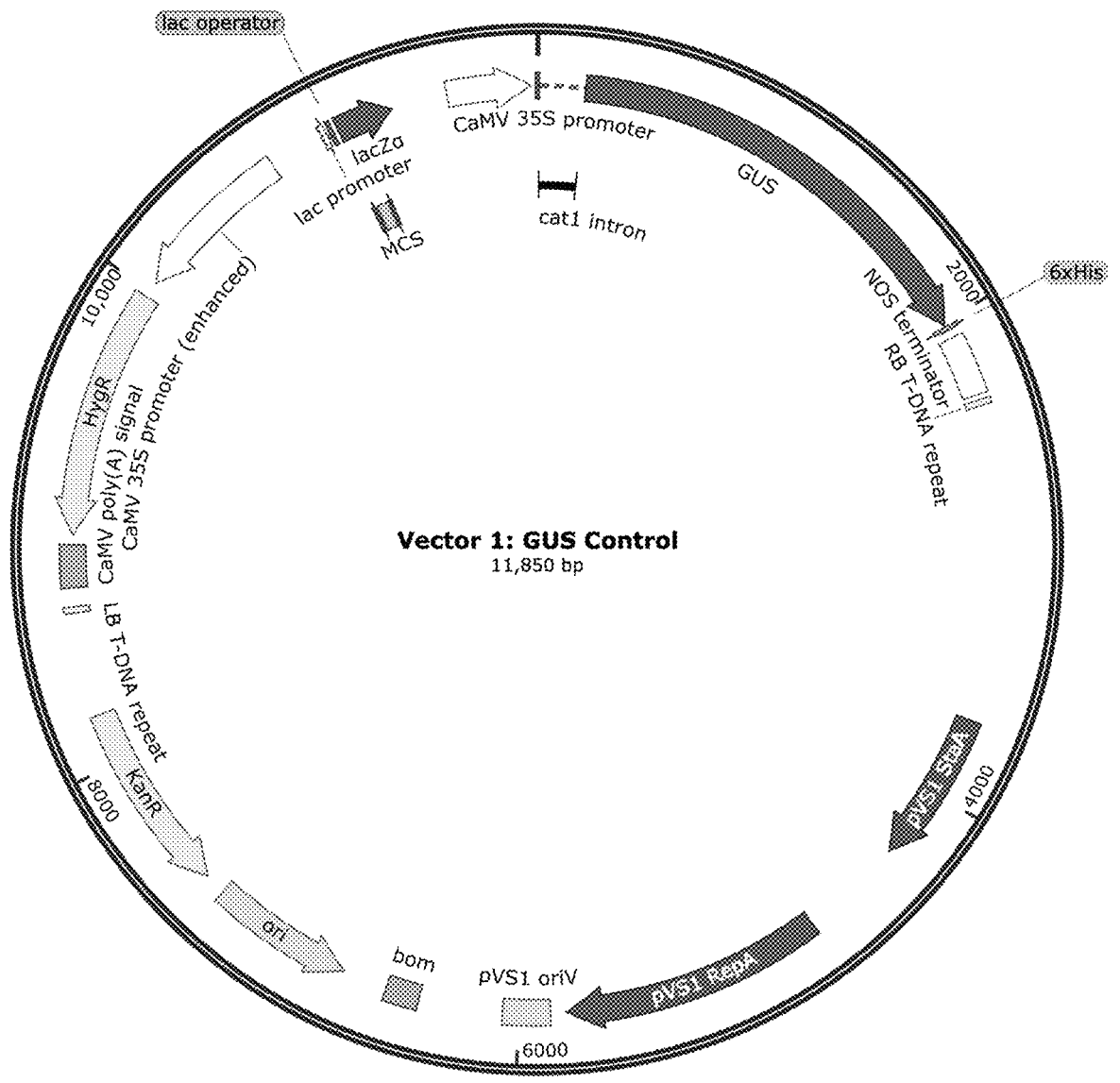
FIG. 4 is a plasmid map depicting a control plasmid comprising a β-glucuronidase (GUS) reporter gene and a hygromycin resistance gene to ensure effective gene uptake for Agrobacterium-mediated transformation.

Aspects of the present disclosure relate to genetic constructs as vectors for delivering one or more genes to a plant cell (e.g., a tomato cell or an eggplant cell). In some embodiments, a vector of the present disclosure is useful for ensuring effective gene uptake by a plant or plant cell via transformation (e.g., Agrobacterium-mediated transformation). A non-limiting example of a vector comprising a β-glucuronidase (GUS) reporter gene flanked by a Cauliflower Mosaic Virus (CaMV 35S) promoter and a Noplaine Synthase (NOS) terminator, a hygromycin resistance gene under control of a CaMV 35S promoter and a CaMV polyadenylation (polyA) termination signal, and a left border (LB) T-DNA repeat and a right border (RB) T-DNA repeat is shown in FIG. 4 and provided as SEQ ID NO: 1:

(SEQ ID NO: 1)

GATCTGAGGGTAAATTTCTAGTTTTTCTCCTTCATTTTCTTGGTTAGGACCCTTTTCTCTTTTTATTTTTTTGAGCT

TTGATCTTTCTTTAAACTGATCTATTTTTTAATTGATTGGTTATGGTGTAAATATTACATAGCTTTAACTGATAATC

-continued

```
TGATTACTTTATTTCGTGTGTCTATGATGATGATGATAGTTACAGAACCGACGACTCGTCCGTCCTGTAGAAACCCC

AACCCGTGAAATCAAAAAACTCGACGGCCTGTGGGCATTCAGTCTGGATCGCGAAAACTGTGGAATTGATCAGCGTT

GGTGGGAAAGCGCGTTACAAGAAAGCCGGGCAATTGCTGTGCCAGGCAGTTTTAACGATCAGTTCGCCGATGCAGAT

ATTCGTAATTATGCGGGCAACGTCTGGTATCAGCGCGAAGTCTTTATACCGAAAGGTTGGGCAGGCCAGCGTATCGT

GCTGCGTTTCGATGCGGTCACTCATTACGGCAAAGTGTGGGTCAATAATCAGGAAGTGATGGAGCATCAGGGCGGCT

ATACGCCATTTGAAGCCGATGTCACGCCGTATGTTATTGCCGGGAAAAGTGTACGTATCACCGTTTGTGTGAACAAC

GAACTGAACTGGCAGACTATCCCGCCGGGAATGGTGATTACCGACGAAAACGGCAAGAAAAAGCAGTCTTACTTCCA

TGATTTCTTTAACTATGCCGGAATCCATCGCAGCGTAATGCTCTACACCACGCCGAACACCTGGGTGGACGATATCA

CCGTGGTGACGCATGTCGCGCAAGACTGTAACCACGCGTCTGTTGACTGGCAGGTGGTGGCCAATGGTGATGTCAGC

GTTGAACTGCGTGATGCGGATCAACAGGTGGTTGCAACTGGACAAGGCACTAGCGGGACTTTGCAAGTGGTGAATCC

GCACCTCTGGCAACCGGGTGAAGGTTATCTCTATGAACTCGAAGTCACAGCCAAAAGCCAGACAGAGTCTGATATCT

ACCCGCTTCGCGTCGGCATCCGGTCAGTGGCAGTGAAGGGCCAACAGTTCCTGATTAACCACAAACCGTTCTACTTT

ACTGGCTTTGGTCGTCATGAAGATGCGGACTTACGTGGCAAAGGATTCGATAACGTGCTGATGGTGCACGACCACGC

ATTAATGGACTGGATTGGGGCCAACTCCTACCGTACCTCGCATTACCCTTACGCTGAAGAGATGCTCGACTGGGCAG

ATGAACATGGCATCGTGGTGATTGATGAAACTGCTGCTGTCGGCTTTCAGCTGTCTTTAGGCATTGGTTTCGAAGCG

GGCAACAAGCCGAAAGAACTGTACAGCGAAGAGGCAGTCAACGGGGAAACTCAGCAAGCGCACTTACAGGCGATTAA

AGAGCTGATAGCGCGTGACAAAAACCACCCAAGCGTGGTGATGTGGAGTATTGCCAACGAACCGGATACCCGTCCGC

AAGGTGCACGGGAATATTTCGCGCCACTGGCGGAAGCAACGCGTAAACTCGACCCGACGCGTCCGATCACCTGCGTC

AATGTAATGTTCTGCGACGCTCACACCGATACCATCAGCGATCTCTTTGATGTGCTGTGCCTGAACCGTTATTACGG

ATGGTATGTCCAAAGCGGCGATTTGGAAACGGCAGAGAAGGTACTGGAAAAAGAACTTCTGGCCTGGCAGGAGAAAC

TGCATCAGCCGATTATCATCACCGAATACGGCGTGGATACGTTAGCCGGGCTGCACTCAATGTACACCGACATGTGG

AGTGAAGAGTATCAGTGTGCATGGCTGGATATGTATCACCGCGTCTTTGATCGCGTCAGCGCCGTCGTCGGTGAACA

GGTATGGAATTTCGCCGATTTTGCGACCTCGCAAGGCATATTGCGCGTTGGCGGTAACAAGAAAGGGATCTTCACTC

GCGACCGCAAACCGAAGTCGGCGGCTTTTCTGCTGCAAAAACGCTGGACTGGCATGAACTTCGGTGAAAAACCGCAG

CAGGGAGGCAAACAAGCTAGCCACCACCACCACCACCACGTGTGAATTACAGGTGACCAGCTCGAATTTCCCCGATC

GTTCAAACATTTGGCAATAAAGTTTCTTAAGATTGAATCCTGTTGCCGGTCTTGCGATGATTATCATATAATTTCTG

TTGAATTACGTTAAGCATGTAATAATTAACATGTAATGCATGACGTTATTTATGAGATGGGTTTTTATGATTAGAGT

CCCGCAATTATACATTTAATACGCGATAGAAAACAAAATATAGCGCGCAAACTAGGATAAATTATCGCGCGCGGTGT

CATCTATGTTACTAGATCGGGAATTAAACTATCAGTGTTTGACAGGATATATTGGCGGGTAAACCTAAGAGAAAAGA

GCGTTTATTAGAATAACGGATATTTAAAAGGGCGTGAAAAGGTTTATCCGTTCGTCCATTTGTATGTGCATGCCAAC

CACAGGGTTCCCCTCGGGATCAAAGTACTTTGATCCAACCCCTCCGCTGCTATAGTGCAGTCGGCTTCTGACGTTCA

GTGCAGCCGTCTTCTGAAAACGACATGTCGCACAAGTCCTAAGTTACGCGACAGGCTGCCGCCCTGCCCTTTTCCTG

GCGTTTTCTTGTCGCGTGTTTTAGTCGCATAAAGTAGAATACTTGCGACTAGAACCGGAGACATTACGCCATGAACA

AGAGCGCCGCCGCTGGCCTGCTGGGCTATGCCCGCGTCAGCACCGACGACCAGGACTTGACCAACCAACGGGCCGAA

CTGCACGCGGCCGGCTGCACCAAGCTGTTTTCCGAGAAGATCACCGGCACCAGGCGCGACCGCCCGGAGCTGGCCAG

GATGCTTGACCACCTACGCCCTGGCGACGTTGTGACAGTGACCAGGCTAGACCGCCTGGCCCGCAGCACCCGCGACC

TACTGGACATTGCCGAGCGCATCCAGGAGGCCGGCGCGGGCCTGCGTAGCCTGGCAGAGCCGTGGGCCGACACCACC

ACGCCGGCCGGCCGCATGGTGTTGACCGTGTTCGCCGGCATTGCCGAGTTCGAGCGTTCCCTAATCATCGACCGCAC

CCGGAGCGGGCGCGAGGCCGCCAAGGCCCGAGGCGTGAAGTTTGGCCCCCGCCCTACCCTCACCCCGGCACAGATCG

CGCACGCCCGCGAGCTGATCGACCAGGAAGGCCGCACCGTGAAAGAGGCGGCTGCACTGCTTGGCGTGCATCGCTCG

ACCCTGTACCGCGCACTTGAGCGCAGCGAGGAAGTGACGCCCACCGAGGCCAGGCGGCGCGGTGCCTTCCGTGAGGA
```

-continued

```
CGCATTGACCGAGGCCGACGCCCTGGCGGCCGCCGAGAATGAACGCCAAGAGGAACAAGCATGAAACCGCACCAGGA

CGGCCAGGACGAACCGTTTTTCATTACCGAAGAGATCGAGGCGGAGATGATCGCGGCCGGGTACGTGTTCGAGCCGC

CCGCGCACGTCTCAACCGTGCGGCTGCATGAAATCCTGGCCGGTTTGTCTGATGCCAAGCTGGCGGCCTGGCCGGCC

AGCTTGGCCGCTGAAGAAACCGAGCGCCGCCGTCTAAAAAGGTGATGTGTATTTGAGTAAAACAGCTTGCGTCATGC

GGTCGCTGCGTATATGATGCGATGAGTAAATAAACAAATACGCAAGGGGAACGCATGAAGGTTATCGCTGTACTTAA

CCAGAAAGGCGGGTCAGGCAAGACGACCATCGCAACCCATCTAGCCCGCGCCCTGCAACTCGCCGGGGCCGATGTTC

TGTTAGTCGATTCCGATCCCCAGGGCAGTGCCCGCGATTGGGCGGCCGTGCGGGAAGATCAACCGCTAACCGTTGTC

GGCATCGACCGCCCGACGATTGACCGCGACGTGAAGGCCATCGGCCGGCGCGACTTCGTAGTGATCGACGGAGCGCC

CCAGGCGGCGGACTTGGCTGTGTCCGCGATCAAGGCAGCCGACTTCGTGCTGATTCCGGTGCAGCCAAGCCCTTACG

ACATATGGGCCACCGCCGACCTGGTGGAGCTGGTTAAGCAGCGCATTGAGGTCACGGATGGAAGGCTACAAGCGGCC

TTTGTCGTGTCGCGGGCGATCAAAGGCACGCGCATCGGCGGTGAGGTTGCCGAGGCGCTGGCCGGGTACGAGCTGCC

CATTCTTGAGTCCCGTATCACGCAGCGCGTGAGCTACCCAGGCACTGCCGCCGCCGGCACAACCGTTCTTGAATCAG

AACCCGAGGGCGACGCTGCCCGCGAGGTCCAGGCGCTGGCCGCTGAAATTAAATCAAAACTCATTTGAGTTAATGAG

GTAAAGAGAAAATGAGCAAAAGCACAAACACGCTAAGTGCCGGCCGTCCGAGCGCACGCAGCAGCAAGGCTGCAACG

TTGGCCAGCCTGGCAGACACGCCAGCCATGAAGCGGGTCAACTTTCAGTTGCCGGCGGAGGATCACACCAAGCTGAA

GATGTACGCGGTACGCCAAGGCAAGACCATTACCGAGCTGCTATCTGAATACATCGCGCAGCTACCAGAGTAAATGA

GCAAATGAATAAATGAGTAGATGAATTTTAGCGGCTAAAGGAGGCGGCATGGAAAATCAAGAACAACCAGGCACCGA

CGCCGTGGAATGCCCCATGTGTGGAGGAACGGGCGGTTGGCCAGGCGTAAGCGGCTGGGTTGTCTGCCGGCCCTGCA

ATGGCACTGGAACCCCCAAGCCCGAGGAATCGGCGTGAGCGGTCGCAAACCATCCGGCCCGGTACAAATCGGCGCGG

CGCTGGGTGATGACCTGGTGGAGAAGTTGAAGGCCGCGCAGGCCGCCCAGCGGCAACGCATCGAGGCAGAAGCACGC

CCCGGTGAATCGTGGCAAGCGGCCGCTGATCGAATCCGCAAAGAATCCCGGCAACCGCCGGCAGCCGGTGCGCCGTC

GATTAGGAAGCCGCCCAAGGGCGACGAGCAACCAGATTTTTTCGTTCCGATGCTCTATGACGTGGGCACCCGCGATA

GTCGCAGCATCATGGACGTGGCCGTTTTCCGTCTGTCGAAGCGTGACCGACGAGCTGGCGAGGTGATCCGCTACGAG

CTTCCAGACGGGCACGTAGAGGTTTCCGCAGGGCCGGCCGGCATGGCCAGTGTGTGGGATTACGACCTGGTACTGAT

GGCGGTTTCCCATCTAACCGAATCCATGAACCGATACCGGGAAGGGAAGGGAGACAAGCCCGGCCGCGTGTTCCGTC

CACACGTTGCGGACGTACTCAAGTTCTGCCGGCGAGCCGATGGCGGAAAGCAGAAAGACGACCTGGTAGAAACCTGC

ATTCGGTTAAACACCACGCACGTTGCCATGCAGCGTACGAAGAAGGCCAAGAACGGCCGCCTGGTGACGGTATCCGA

GGGTGAAGCCTTGATTAGCCGCTACAAGATCGTAAAGAGCGAAACCGGGCGGCCGGAGTACATCGAGATCGAGCTAG

CTGATTGGATGTACCGCGAGATCACAGAAGGCAAGAACCCGGACGTGCTGACGGTTCACCCCGATTACTTTTTGATC

GATCCCGGCATCGGCCGTTTTCTCTACCGCCTGGCACGCCGCGCCGCAGGCAAGGCAGAAGCCAGATGGTTGTTCAA

GACGATCTACGAACGCAGTGGCAGCGCCGGAGAGTTCAAGAAGTTCTGTTTCACCGTGCGCAAGCTGATCGGGTCAA

ATGACCTGCCGGAGTACGATTTGAAGGAGGAGGCGGGGCAGGCTGGCCCGATCCTAGTCATGCGCTACCGCAACCTG

ATCGAGGGCGAAGCATCCGCCGGTTCCTAATGTACGGAGCAGATGCTAGGGCAAATTGCCCTAGCAGGGGAAAAAGG

TCGAAAAGGTCTCTTTCCTGTGGATAGCACGTACATTGGGAACCCAAAGCCGTACATTGGGAACCGGAACCCGTACA

TTGGGAACCCAAAGCCGTACATTGGGAACCGGTCACACATGTAAGTGACTGATATAAAAGAGAAAAAAGGCGATTTT

TCCGCCTAAAACTCTTTAAAACTTATTAAAACTCTTAAAACCCGCCTGGCCTGTGCATAACTGTCTGGCCAGCGCAC

AGCCGAAGAGCTGCAAAAAGCGCCTACCCTTCGGTCGCTGCGCTCCCTACGCCCCGCCGCTTCGCGTCGGCCTATCG

CGGCCGCTGGCCGCTCAAAAATGGCTGGCCTACGGCCAGGCAATCTACCAGGGCGCGGACAAGCCGCGCCGTCGCCA

CTCGACCGCCGGCGCCCACATCAAGGCACCCTGCCTCGCGCGTTTCGGTGATGACGGTGAAAACCTCTGACACATGC

AGCTCCCGGAGACGGTCACAGCTTGTCTGTAAGCGGATGCCGGGAGCAGACAAGCCCGTCAGGGCGCGTCAGCGGGT
```

-continued

```
GTTGGCGGGTGTCGGGGCGCAGCCATGACCCAGTCACGTAGCGATAGCGGAGTGTATACTGGCTTAACTATGCGGCA

TCAGAGCAGATTGTACTGAGAGTGCACCATATGCGGTGTGAAATACCGCACAGATGCGTAAGGAGAAAATACCGCAT

CAGGCGCTCTTCCGCTTCCTCGCTCACTGACTCGCTGCGCTCGGTCGTTCGGCTGCGGCGAGCGGTATCAGCTCACT

CAAAGGCGGTAATACGGTTATCCACAGAATCAGGGGATAACGCAGGAAAGAACATGTGAGCAAAAGGCCAGCAAAAG

GCCAGGAACCGTAAAAAGGCCGCGTTGCTGGCGTTTTTCCATAGGCTCCGCCCCCCTGACGAGCATCACAAAAATCG

ACGCTCAAGTCAGAGGTGGCGAAACCCGACAGGACTATAAAGATACCAGGCGTTTCCCCCTGGAAGCTCCCTCGTGC

GCTCTCCTGTTCCGACCCTGCCGCTTACCGGATACCTGTCCGCCTTTCTCCCTTCGGGAAGCGTGGCGCTTTCTCAT

AGCTCACGCTGTAGGTATCTCAGTTCGGTGTAGGTCGTTCGCTCCAAGCTGGGCTGTGTGCACGAACCCCCCGTTCA

GCCCGACCGCTGCGCCTTATCCGGTAACTATCGTCTTGAGTCCAACCCGGTAAGACACGACTTATCGCCACTGGCAG

CAGCCACTGGTAACAGGATTAGCAGAGCGAGGTATGTAGGCGGTGCTACAGAGTTCTTGAAGTGGTGGCCTAACTAC

GGCTACACTAGAAGGACAGTATTTGGTATCTGCGCTCTGCTGAAGCCAGTTACCTTCGGAAAAAGAGTTGGTAGCTC

TTGATCCGGCAAACAAACCACCGCTGGTAGCGGTGGTTTTTTTGTTTGCAAGCAGCAGATTACGCGCAGAAAAAAAG

GATCTCAAGAAGATCCTTTGATCTTTTCTACGGGGTCTGACGCTCAGTGGAACGAAAACTCACGTTAAGGGATTTTG

GTCATGCATTCTAGGTACTAAAACAATTCATCCAGTAAAATATAATATTTTATTTTCTCCCAATCAGGCTTGATCCC

CAGTAAGTCAAAAAATAGCTCGACATACTGTTCTTCCCCGATATCCTCCCTGATCGACCGGACGCAGAAGGCAATGT

CATACCACTTGTCCGCCCTGCCGCTTCTCCCAAGATCAATAAAGCCACTTACTTTGCCATCTTTCACAAAGATGTTG

CTGTCTCCCAGGTCGCCGTGGGAAAAGACAAGTTCCTCTTCGGGCTTTTCCGTCTTTAAAAAATCATACAGCTCGCG

CGGATCTTTAAATGGAGTGTCTTCTTCCCAGTTTTCGCAATCCACATCGGCCAGATCGTTATTCAGTAAGTAATCCA

ATTCGGCTAAGCGGCTGTCTAAGCTATTCGTATAGGGACAATCCGATATGTCGATGGAGTGAAAGAGCCTGATGCAC

TCCGCATACAGCTCGATAATCTTTTCAGGGCTTTGTTCATCTTCATACTCTTCCGAGCAAAGGACGCCATCGGCCTC

ACTCATGAGCAGATTGCTCCAGCCATCATGCCGTTCAAAGTGCAGGACCTTTGGAACAGGCAGCTTTCCTTCCAGCC

ATAGCATCATGTCCTTTTCCCGTTCCACATCATAGGTGGTCCCTTTATACCGGCTGTCCGTCATTTTTAAATATAGG

TTTTCATTTTCTCCCACCAGCTTATATACCTTAGCAGGAGACATTCCTTCCGTATCTTTTACGCAGCGGTATTTTTC

GATCAGTTTTTTCAATTCCGGTGATATTCTCATTTTAGCCATTTATTATTTCCTTCCTCTTTTCTACAGTATTTAAA

GATACCCCAAGAAGCTAATTATAACAAGACGAACTCCAATTCACTGTTCCTTGCATTCTAAAACCTTAAATACCAGA

AAACAGCTTTTTCAAAGTTGTTTTCAAAGTTGGCGTATAACATAGTATCGACGGAGCCGATTTTGAAACCGCGGTGA

TCACAGGCAGCAACGCTCTGTCATCGTTACAATCAACATGCTACCCTCCGCGAGATCATCCGTGTTTCAAACCCGGC

AGCTTAGTTGCCGTTCTTCCGAATAGCATCGGTAACATGAGCAAAGTCTGCCGCCTTACAACGGCTCTCCCGCTGAC

GCCGTCCCGGACTGATGGGCTGCCTGTATCGAGTGGTGATTTTGTGCCGAGCTGCCGGTCGGGGAGCTGTTGGCTGG

CTGGTGGCAGGATATATTGTGGTGTAAACAAATTGACGCTTAGACAACTTAATAACACATTGCGGACGTTTTTAATG

TACTGAATTAACGCCGAATTAATTCGGGGGATCTGGATTTTAGTACTGGATTTTGGTTTTAGGAATTAGAAATTTTA

TTGATAGAAGTATTTTACAAATACAAATACATACTAAGGGTTTCTTATATGCTCAACACATGAGCGAAACCCTATAG

GAACCCTAATTCCCTTATCTGGGAACTACTCACACATTATTATGGAGAAACTCGAGCTTGTCGATCGACAGATCCGG

TCGGCATCTACTCTATTTCTTTGCCCTCGGACGAGTGCTGGGGCGTCGGTTTCCACTATCGGCGAGTACTTCTACAC

AGCCATCGGTCCAGACGGCCGCGCTTCTGCGGGCGATTTGTGTACGCCCGACAGTCCCGGCTCCGGATCGGACGATT

GCGTCGCATCGACCCTGCGCCCAAGCTGCATCATCGAAATTGCCGTCAACCAAGCTCTGATAGAGTTGGTCAAGACC

AATGCGGAGCATATACGCCCGGAGTCGTGGCGATCCTGCAAGCTCCGGATGCCTCCGCTCGAAGTAGCGCGTCTGCT

GCTCCATACAAGCCAACCACGGCCTCCAGAAGAAGATGTTGGCGACCTCGTATTGGGAATCCCCGAACATCGCCTCG

CTCCAGTCAATGACCGCTGTTATGCGGCCATTGTCCGTCAGGACATTGTTGGAGCCGAAATCCGCGTGCACGAGGTG

CCGGACTTCGGGGCAGTCCTCGGCCCAAAGCATCAGCTCATCGAGAGCCTGCGCGACGGACGCACTGACGGTGTCGT

CCATCACAGTTTGCCAGTGATACACATGGGGATCAGCAATCGCGCATATGAAATCACGCCATGTAGTGTATTGACCG
```

-continued

ATTCCTTGCGGTCCGAATGGGCCGAACCCGCTCGTCTGGCTAAGATCGGCCGCAGCGATCGCATCCATAGCCTCCGC

GACCGGTTGTAGAACAGCGGGCAGTTCGGTTTCAGGCAGGTCTTGCAACGTGACACCCTGTGCACGGCGGGAGATGC

AATAGGTCAGGCTCTCGCTAAACTCCCCAATGTCAAGCACTTCCGGAATCGGGAGCGCGGCCGATGCAAAGTGCCGA

TAAACATAACGATCTTTGTAGAAACCATCGGCGCAGCTATTTACCCGCAGGACATATCCACGCCCTCCTACATCGAA

GCTGAAAGCACGAGATTCTTCGCCCTCCGAGAGCTGCATCAGGTCGGAGACGCTGTCGAACTTTTCGATCAGAAACT

TCTCGACAGACGTCGCGGTGAGTTCAGGCTTTTTCATATCTCATTGCCCCCCGGGATCTGCGAAAGCTCGAGAGAGA

TAGATTTGTAGAGAGAGACTGGTGATTTCAGCGTGTCCTCTCCAAATGAAATGAACTTCCTTATATAGAGGAAGGTC

TTGCGAAGGATAGTGGGATTGTGCGTCATCCCTTACGTCAGTGGAGATATCACATCAATCCACTTGCTTTGAAGACG

TGGTTGGAACGTCTTCTTTTTCCACGATGCTCCTCGTGGGTGGGGGTCCATCTTTGGGACCACTGTCGGCAGAGGCA

TCTTGAACGATAGCCTTTCCTTTATCGCAATGATGGCATTTGTAGGTGCCACCTTCCTTTTCTACTGTCCTTTTGAT

GAAGTGACAGATAGCTGGGCAATGGAATCCGAGGAGGTTTCCCGATATTACCCTTTGTTGAAAAGTCTCAATAGCCC

TTTGGTCTTCTGAGACTGTATCTTTGATATTCTTGGAGTAGACGAGAGTGTCGTGCTCCACCATGTTATCACATCAA

TCCACTTGCTTTGAAGACGTGGTTGGAACGTCTTCTTTTTCCACGATGCTCCTCGTGGGTGGGGGTCCATCTTTGGG

ACCACTGTCGGCAGAGGCATCTTGAACGATAGCCTTTCCTTTATCGCAATGATGGCATTTGTAGGTGCCACCTTCCT

TTTCTACTGTCCTTTTGATGAAGTGACAGATAGCTGGGCAATGGAATCCGAGGAGGTTTCCCGATATTACCCTTTGT

TGAAAAGTCTCAATAGCCCTTTGGTCTTCTGAGACTGTATCTTTGATATTCTTGGAGTAGACGAGAGTGTCGTGCTC

CACCATGTTGGCAAGCTGCTCTAGCCAATACGCAAACCGCCTCTCCCCGCGCGTTGGCCGATTCATTAATGCAGCTG

GCACGACAGGTTTCCCGACTGGAAAGCGGGCAGTGAGCGCAACGCAATTAATGTGAGTTAGCTCACTCATTAGGCAC

CCCAGGCTTTACACTTTATGCTTCCGGCTCGTATGTTGTGTGGAATTGTGAGCGGATAACAATTTCACACAGGAAAC

AGCTATGACCATGATTACGAATTCGAGCTCGGTACCCGGGGATCCTCTAGAGTCGACCTGCAGGCATGCAAGCTTGG

CACTGGCCGTCGTTTTACAACGTCGTGACTGGGAAAACCCTGGCGTTACCCAACTTAATCGCCTTGCAGCACATCCC

CCTTTCGCCAGCTGGCGTAATAGCGAAGAGGCCCGCACCGATCGCCCTTCCCAACAGTTGCGCAGCCTGAATGGCGA

ATGCTAGAGCAGCTTGAGCTTGGATCAGATTGTCGTTTCCCGCCTTCAGTTTAGCTTCATGGAGTCAAAGATTCAAA

TAGAGGACCTAACAGAACTCGCCGTAAAGACTGGCGAACAGTTCATACAGAGTCTCTTACGACTCAATGACAAGAAG

AAAATCTTCGTCAACATGGTGGAGCACGACACACTTGTCTACTCCAAAAATATCAAAGATACAGTCTCAGAAGACCA

AAGGGCAATTGAGACTTTTCAACAAAGGGTAATATCGGGAAACCTCCTCGGATTCCATTGCCCAGCTATCTGTCACT

TTATTGTGAAGATAGTGGAAAAGGAAGGTGGCTCCTACAAATGCCATCATTGCGATAAAGGAAAGGCCATCGTTGAA

GATGCCTCTGCCGACAGTGGTCCCAAAGATGGACCCCCACCCACGAGGAGCATCGTGGAAAAAGAAGACGTTCCAAC

CACGTCTTCAAAGCAAGTGGATTGATGTGATATCTCCACTGACGTAAGGGATGACGCACAATCCCACTATCCTTCGC

AAGACCCTTCCTCTATATAAGGAAGTTCATTTCATTTGGAGAGAACACGGGGGACTCTTGACCATGGTA

In some embodiments, a vector of the present disclosure (e.g., a plasmid) is useful for delivering a heme-producing gene to a plant cell (e.g., a tomato cell or an eggplant cell).

Figure 5:
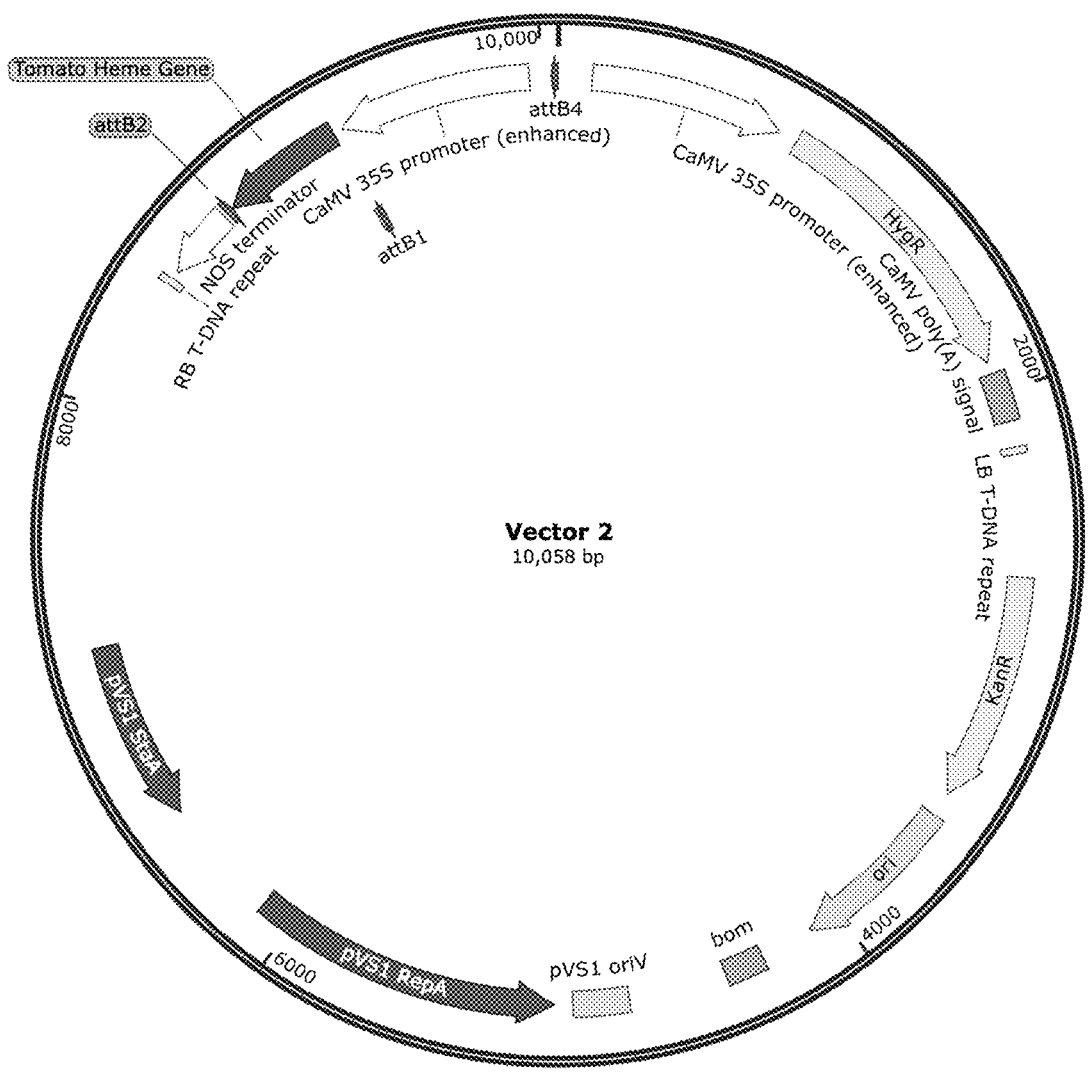
FIG. 5 is a plasmid map depicting a codon-optimized leghemoglobin gene under control of a Cauliflower Mosaic Virus (CaMV 35S) promoter and a Noplaine Synthase (NOS) terminator, with hygromycin resistance gene under control of a CaMV 35S promoter and a CaMV polyadenylation (polyA) termination signal.

A non-limiting example of a vector comprising a codon-optimized heme-producing gene flanked by a CaMV 35S promoter and a NOS terminator, a hygromycin resistance gene under control of a CaMV 35S promoter and a CaMV polyA termination signal, and a left border (LB) T-DNA repeat and a right border (RB) T-DNA repeat is shown in FIG. 5 and provided as SEQ ID NO: 2:

(SEQ ID NO: 2)

AGCTTGCATGCCTGCAGGTCGACTCTAGAGGATCCCCGGGTACGCCAACATGGTGGAGCACGACACTCTCGTCTACT

CCAAGAATATCAAAGATACAGTCTCAGAAGACCAAAGGGCTATTGAGACTTTTCAACAAAGGGTAATATCGGGAAAC

CTCCTCGGATTCCATTGCCCAGCTATCTGTCACTTCATCAAAAGGACAGTAGAAAAGGAAGGTGGCACCTACAAATG

CCATCATTGCGATAAAGGAAAGGCTATCGTTCAAGATGCCTCTGCCGACAGTGGTCCCAAAGATGGACCCCCACCCA

CGAGGAGCATCGTGGAAAAAGAAGACGTTCCAACCACGTCTTCAAAGCAAGTGGATTGATGTGAACATGGTGGAGCA

-continued

```
CGACACTCTCGTCTACTCCAAGAATATCAAAGATACAGTCTCAGAAGACCAAAGGGCTATTGAGACTTTTCAACAAA

GGGTAATATCGGGAAACCTCCTCGGATTCCATTGCCCAGCTATCTGTCACTTCATCAAAAGGACAGTAGAAAAGGAA

GGTGGCACCTACAAATGCCATCATTGCGATAAAGGAAAGGCTATCGTTCAAGATGCCTCTGCCGACAGTGGTCCCAA

AGATGGACCCCCACCCACGAGGAGCATCGTGGAAAAAGAAGACGTTCCAACCACGTCTTCAAAGCAAGTGGATTGAT

GTGATATCTCCACTGACGTAAGGGATGACGCACAATCCCACTATCCTTCGCAAGACCCTTCCTCTATATAAGGAAGT

TCATTTCATTTGGAGAGGACACGCTGAAATCACCAGTCTCTCTCTACAAATCTATCTCTCTCGAGCTTTCGCAGATC

CGGGGGGCAATGAGATATGAAAAAGCCTGAACTCACCGCGACGTCTGTCGAGAAGTTTCTGATCGAAAAGTTCGACA

GCGTCTCCGACCTGATGCAGCTCTCGGAGGGCGAAGAATCTCGTGCTTTCAGCTTCGATGTAGGAGGGCGTGGATAT

GTCCTGCGGGTAAATAGCTGCGCCGATGGTTTCTACAAAGATCGTTATGTTTATCGGCACTTTGCATCGGCCGCGCT

CCCGATTCCGGAAGTGCTTGACATTGGGGAGTTTAGCGAGAGCCTGACCTATTGCATCTCCCGCCGTTCACAGGGTG

TCACGTTGCAAGACCTGCCTGAAACCGAACTGCCCGCTGTTCTACAACCGGTCGCGGAGGCTATGGATGCGATCGCT

GCGGCCGATCTTAGCCAGACGAGCGGGTTCGGCCCATTCGGACCGCAAGGAATCGGTCAATACACTACATGGCGTGA

TTTCATATGCGCGATTGCTGATCCCCATGTGTATCACTGGCAAACTGTGATGGACGACACCGTCAGTGCGTCCGTCG

CGCAGGCTCTCGATGAGCTGATGCTTTGGGCCGAGGACTGCCCCGAAGTCCGGCACCTCGTGCACGCGGATTTCGGC

TCCAACAATGTCCTGACGGACAATGGCCGCATAACAGCGGTCATTGACTGGAGCGAGGCGATGTTCGGGGATTCCCA

ATACGAGGTCGCCAACATCTTCTTCTGGAGGCCGTGGTTGGCTTGTATGGAGCAGCAGACGCGCTACTTCGAGCGGA

GGCATCCGGAGCTTGCAGGATCGCCACGACTCCGGGCGTATATGCTCCGCATTGGTCTTGACCAACTCTATCAGAGC

TTGGTTGACGGCAATTTCGATGATGCAGCTTGGGCGCAGGGTCGATGCGACGCAATCGTCCGATCCGGAGCCGGGAC

TGTCGGGCGTACACAAATCGCCCGCAGAAGCGCGGCCGTCTGGACCGATGGCTGTGTAGAAGTACTCGCCGATAGTG

GAAACCGACGCCCCAGCACTCGTCCGAGGGCAAAGAAATAGAGTAGATGCCGACCGGGATCTGTCGATCGACAAGCT

CGAGTTTCTCCATAATAATGTGTGAGTAGTTCCCAGATAAGGGAATTAGGGTTCCTATAGGGTTTCGCTCATGTGTT

GAGCATATAAGAAACCCTTAGTATGTATTTGTATTTGTAAAATACTTCTATCAATAAAATTTCTAATTCCTAAAACC

AAAATCCAGTACTAAAATCCAGATCCCCCGGTACCGAGCTCGAATTCAATTCGGCGTTAATTCAGTACATTAAAAAC

GTCCGCAATGTGTTATTAAGTTGTCTAAGCGTCAATTTGTTTACACCACAATATATCCTGCCACCAGCCAGCCAACA

GCTCCCCGACCGGCAGCTCGGCACAAAATCACCACTCGATACAGGCAGCCCATCAGTCCGGGACGGCGTCAGCGGGA

GAGCCGTTGTAAGGCGGCAGACTTTGCTCATGTTACCGATGCTATTCGGAAGAACGGCAACTAAGCTGCCGGGTTTG

AAACACGGATGATCTCGCGGAGGGTAGCATGTTGATTGTAACGATGACAGAGCGTTGCTGCCTGTGATCACCGCGGT

TTCAAAATCGGCTCCGTCGATACTATGTTATACGCCAACTTTGAAAACAACTTTGAAAAAGCTGTTTTCTGGTATTT

AAGGTTTTAGAATGCAAGGAACAGTGAATTGGAGTTCGTCTTGTTATAATTAGCTTCTTGGGGTATCTTTAAATACT

GTAGAAAAGAGGAAGGAAATAATAAATGGCTAAAATGAGAATATCACCGGAATTGAAAAAACTGATCGAAAAATACC

GCTGCGTAAAAGATACGGAAGGAATGTCTCCTGCTAAGGTATATAAGCTGGTGGGAGAAAATGAAAACCTATATTTA

AAAATGACGGACAGCCGGTATAAAGGGACCACCTATGATGTGGAACGGGAAAAGGACATGATGCTATGGCTGGAAGG

AAAGCTGCCTGTTCCAAAGGTCCTGCACTTTGAACGGCATGATGGCTGGAGCAATCTGCTCATGAGTGAGGCCGATG

GCGTCCTTTGCTCGGAAGAGTATGAAGATGAACAAAGCCCTGAAAAGATTATCGAGCTGTATGCGGAGTGCATCAGG

CTCTTTCACTCCATCGACATATCGGATTGTCCCTATACGAATAGCTTAGACAGCCGCTTAGCCGAATTGGATTACTT

ACTGAATAACGATCTGGCCGATGTGGATTGCGAAACTGGGAAGAAGACACTCCATTTAAAGATCCGCGCGAGCTGT

ATGATTTTTTAAAGACGGAAAAGCCCGAAGAGGAACTTGTCTTTTCCCACGGCGACCTGGGAGACAGCAACATCTTT

GTGAAAGATGGCAAAGTAAGTGGCTTTATTGATCTTGGGAGAAGCGGCAGGGCGGACAAGTGGTATGACATTGCCTT

CTGCGTCCGGTCGATCAGGGAGGATATCGGGGAAGAACAGTATGTCGAGCTATTTTTTGACTTACTGGGGATCAAGC

CTGATTGGGAGAAAATAAAAATATTATATTTTACTGGATGAATTGTTTTAGTACCTAGAATGCATGACCAAAATCCCT

TAACGTGAGTTTTCGTTCCACTGAGCGTCAGACCCCGTAGAAAAGATCAAAGGATCTTCTTGAGATCCTTTTTTTCT
```

-continued

```
GCGCGTAATCTGCTGCTTGCAAACAAAAAAACCACCGCTACCAGCGGTGGTTTGTTTGCCGGATCAAGAGCTACCAA

CTCTTTTTCCGAAGGTAACTGGCTTCAGCAGAGCGCAGATACCAAATACTGTCCTTCTAGTGTAGCCGTAGTTAGGC

CACCACTTCAAGAACTCTGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCGGTCGGGCTGAACGGGGG

GTTCGTGCACACAGCCCAGCTTGGAGCGAACGACCTACACCGAACTGAGATACCTACAGCGTGAGCTATGAGAAAGC

GCCACGCTTCCCGAAGGGAGAAAGGCGGACAGGTATCCGGTAAGCGGCAGGGTCGGAACAGGAGAGCGCACGAGGGA

GCTTCCAGGGGGAAACGCCTGGTATCTTTATAGTCCTGTCGGGTTTCGCCACCTCTGACTTGAGCGTCGATTTTTGT

GATGCTCGTCAGGGGGGCGGAGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTACCGCCTTTGAGTGAGCTGA

TACCGCTCGCCGCAGCCGAACGACCGAGCGCAGCGAGTCAGTGAGCGAGGAAGCGGAAGAGCGCCTGATGCGGTATT

TTCTCCTTACGCATCTGTGCGGTATTTCACACCGCATATGGTGCACTCTCAGTACAATCTGCTCTGATGCCGCATAG

TTAAGCCAGTATACACTCCGCTATCGCTACGTGACTGGGTCATGGCTGCGCCCCGACACCCGCCAACACCCGCTGAC

GCGCCCTGACGGGCTTGTCTGCTCCCGGCATCCGCTTACAGACAAGCTGTGACCGTCTCCGGGAGCTGCATGTGTCA

GAGGTTTTCACCGTCATCACCGAAACGCGCGAGGCAGGGTGCCTTGATGTGGGCGCCGGCGGTCGAGTGGCGACGGC

GCGGCTTGTCCGCGCCCTGGTAGATTGCCTGGCCGTAGGCCAGCCATTTTTGAGCGGCCAGCGGCCGCGATAGGCCG

ACGCGAAGCGGCGGGGCGTAGGGAGCGCAGCGACCGAAGGGTAGGCGCTTTTTGCAGCTCTTCGGCTGTGCGCTGGC

CAGACAGTTATGCACAGGCCAGGCGGGTTTTAAGAGTTTTAATAAGTTTTAAAGAGTTTTAGGCGGAAAAATCGCCT

TTTTTCTCTTTTATATCAGTCACTTACATGTGTGACCGGTTCCCAATGTACGGCTTTGGGTTCCCAATGTACGGGTT

CCGGTTCCCAATGTACGGCTTTGGGTTCCCAATGTACGTGCTATCCACAGGAAAGAGACCTTTTCGACCTTTTTCCC

CTGCTAGGGCAATTTGCCCTAGCATCTGCTCCGTACATTAGGAACCGGCGGATGCTTCGCCCTCGATCAGGTTGCGG

TAGCGCATGACTAGGATCGGGCCAGCCTGCCCCGCCTCCTCCTTCAAATCGTACTCCGGCAGGTCATTTGACCCGAT

CAGCTTGCGCACGGTGAAACAGAACTTCTTGAACTCTCCGGCGCTGCCACTGCGTTCGTAGATCGTCTTGAACAACC

ATCTGGCTTCTGCCTTGCCTGCGGCGCGGCGTGCCAGGCGGTAGAGAAAACGGCCGATGCCGGGATCGATCAAAAAG

TAATCGGGGTGAACCGTCAGCACGTCCGGGTTCTTGCCTTCTGTGATCTCGCGGTACATCCAATCAGCTAGCTCGAT

CTCGATGTACTCCGGCCGCCCGGTTTCGCTCTTTACGATCTTGTAGCGGCTAATCAAGGCTTCACCCTCGGATACCG

TCACCAGGCGGCCGTTCTTGGCCTTCTTCGTACGCTGCATGGCAACGTGCGTGGTGTTTAACCGAATGCAGGTTTCT

ACCAGGTCGTCTTTCTGCTTTCCGCCATCGGCTCGCCGGCAGAACTTGAGTACGTCCGCAACGTGTGGACGGAACAC

GCGGCCGGGCTTGTCTCCCTTCCCTTCCCGGTATCGGTTCATGGATTCGGTTAGATGGGAAACCGCCATCAGTACCA

GGTCGTAATCCCACACACTGGCCATGCCGGCCGGCCCTGCGGAAACCTCTACGTGCCCGTCTGGAAGCTCGTAGCGG

ATCACCTCGCCAGCTCGTCGGTCACGCTTCGACAGACGGAAAACGGCCACGTCCATGATGCTGCGACTATCGCGGGT

GCCCACGTCATAGAGCATCGGAACGAAAAAATCTGGTTGCTCGTCGCCCTTGGGCGGCTTCCTAATCGACGGCGCAC

CGGCTGCCGGCGGTTGCCGGGATTCTTTGCGGATTCGATCAGCGGCCGCTTGCCACGATTCACCGGGGCGTGCTTCT

GCCTCGATGCGTTGCCGCTGGGCGGCCTGCGCGGCCTTCAACTTCTCCACCAGGTCATCACCCAGCGCCGCGCCGAT

TTGTACCGGGCCGGATGGTTTGCGACCGCTCACGCCGATTCCTCGGGCTTGGGGGTTCCAGTGCCATTGCAGGGCCG

GCAGGCAACCCAGCCGCTTACGCCTGGCCAACCGCCCGTTCCTCCACACATGGGGCATTCCACGGCGTCGGTGCCTG

GTTGTTCTTGATTTTCCATGCCGCCTCCTTTAGCCGCTAAAATTCATCTACTCATTTATTCATTTGCTCATTTACTC

TGGTAGCTGCGCGATGTATTCAGATAGCAGCTCGGTAATGGTCTTGCCTTGGCGTACCGCGTACATCTTCAGCTTGG

TGTGATCCTCCGCCGGCAACTGAAAGTTGACCCGCTTCATGGCTGGCGTGTCTGCCAGGCTGGCCAACGTTGCAGCC

TTGCTGCTGCGTGCGCTCGGACGGCCGGCACTTAGCGTGTTTGTGCTTTTGCTCATTTTCTCTTTACCTCATTAACT

CAAATGAGTTTTGATTTAATTTCAGCGGCCAGCGCCTGGACCTCGCGGGCAGCGTCGCCCTCGGGTTCTGATTCAAG
```

-continued

```
AACGGTTGTGCCGGCGGCGGCAGTGCCTGGGTAGCTCACGCGCTGCGTGATACGGGACTCAAGAATGGGCAGCTCGT

ACCCGGCCAGCGCCTCGGCAACCTCACCGCCGATGCGCGTGCCTTTGATCGCCCGCGACACGACAAAGGCCGCTTGT

AGCCTTCCATCCGTGACCTCAATGCGCTGCTTAACCAGCTCCACCAGGTCGGCGGTGGCCCATATGTCGTAAGGGCT

TGGCTGCACCGGAATCAGCACGAAGTCGGCTGCCTTGATCGCGGACACAGCCAAGTCCGCCGCCTGGGGCGCTCCGT

CGATCACTACGAAGTCGCGCCGGCCGATGGCCTTCACGTCGCGGTCAATCGTCGGGCGGTCGATGCCGACAACGGTT

AGCGGTTGATCTTCCCGCACGGCCGCCCAATCGCGGGCACTGCCCTGGGGATCGGAATCGACTAACAGAACATCGGC

CCCGGCGAGTTGCAGGGCGCGGGCTAGATGGGTTGCGATGGTCGTCTTGCCTGACCCGCCTTTCTGGTTAAGTACAG

CGATAACCTTCATGCGTTCCCCTTGCGTATTTGTTTATTTACTCATCGCATCATATACGCAGCGACCGCATGACGCA

AGCTGTTTTACTCAAATACACATCACCTTTTTAGACGGCGGCGCTCGGTTTCTTCAGCGGCCAAGCTGGCCGGCCAG

GCCGCCAGCTTGGCATCAGACAAACCGGCCAGGATTTCATGCAGCCGCACGGTTGAGACGTGCGCGGGCGGCTCGAA

CACGTACCCGGCCGCGATCATCTCCGCCTCGATCTCTTCGGTAATGAAAAACGGTTCGTCCTGGCCGTCCTGGTGCG

GTTTCATGCTTGTTCCTCTTGGCGTTCATTCTCGGCGGCCGCCAGGGCGTCGGCCTCGGTCAATGCGTCCTCACGGA

AGGCACCGCGCCGCCTGGCCTCGGTGGGCGTCACTTCCTCGCTGCGCTCAAGTGCGCGGTACAGGGTCGAGCGATGC

ACGCCAAGCAGTGCAGCCGCCTCTTTCACGGTGCGGCCTTCCTGGTCGATCAGCTCGCGGGCGTGCGCGATCTGTGC

CGGGGTGAGGGTAGGGCGGGGGCCAAACTTCACGCCTCGGGCCTTGGCGGCCTCGCGCCCGCTCCGGGTGCGGTCGA

TGATTAGGGAACGCTCGAACTCGGCAATGCCGGCGAACACGGTCAACACCATGCGGCCGGCCGGCGTGGTGGTGTCG

GCCCACGGCTCTGCCAGGCTACGCAGGCCCGCGCCGGCCTCCTGGATGCGCTCGGCAATGTCCAGTAGGTCGCGGGT

GCTGCGGGCCAGGCGGTCTAGCCTGGTCACTGTCACAACGTCGCCAGGGCGTAGGTGGTCAAGCATCCTGGCCAGCT

CCGGGCGGTCGCGCCTGGTGCCGGTGATCTTCTCGGAAAACAGCTTGGTGCAGCCGGCCGCGTGCAGTTCGGCCCGT

TGGTTGGTCAAGTCCTGGTCGTCGGTGCTGACGCGGGCATAGCCCAGCAGGCCAGCGGCGGCGCTCTTGTTCATGGC

GTAATGTCTCCGGTTCTAGTCGCAAGTATTCTACTTTATGCGACTAAAACACGCGACAAGAAAACGCCAGGAAAAGG

GCAGGGCGGCAGCCTGTCGCGTAACTTAGGACTTGTGCGACATGTCGTTTTCAGAAGACGGCTGCACTGAACGTCAG

AAGCCGACTGCACTATAGCAGCGGAGGGGTTGGATCAAAGTACTTTGATCCCGAGGGGAACCCTGTGGTTGGCATGC

ACATACAAATGGACGAACGGATAAACCTTTTCACGCCCTTTTAAATATCCGATTATTCTAATAAACGCTCTTTTCTC

TTAGGTTTACCCGCCAATATATCCTGTCAAACACTGATAGTTTAAAAGCTTTCCCGATCTAGTAACATAGATGACAC

CGCGCGCGATAATTTATCCTAGTTTGCGCGCTATATTTTGTTTTCTATCGCGTATTAAATGTATAATTGCGGGACTC

TAATCATAAAAACCCATCTCATAAATAACGTCATGCATTACATGTTAATTATTACATGCTTAACGTAATTCAACAGA

AATTATATGATAATCATCGCAAGACCGGCAACAGGATTCAATCTTAAGAAACTTTATTGCCAAATGTTTGAACGATC

GGGGAAATTCGAGCTACCACTTTGTACAAGAAAGCTGGGTTTAAGCCTTCTTGATAGCAGCAGCGAGTTCATCGTAA

GCAACTTCCCAAGCCCTAGACAATTCATCTGACCATTTATCACCAACAGCAGCTTTAATAGTTTTAAGCAAAGCTTC

TTTCACAACAACGAACTGAGGATCTGTAACAGCCTTTTGAGCATGAACTGAACCCAAAGCAGCATCAGCAACAACTG

TCCCAGAAGCTTTAAGCTGACCAGCTGAATCTCTCACCAGAGCAAAAAGCTTTTCTGCATGTCCAGTCAACTTAGGA

TTTGTTGGATCAACACCGTTAGCCAAAAATGAAAACAAATCCTTAGCAGCAGGAGCTTTTTCCAAAATTGATGTGTA

GAAAACCACAGAATATTGTGGAATATTTGCCTTGAAAGCTTCAAATGATGATGAAACAAGAGCATCTTGCTTTTCAG

TAAAAGCAACCATGGTGGCAGCCTGCTTTTTTGTACAAACTTGTCAGCGTGTCCTCTCCAAATGAAATGAACTTCCT

TATATAGAGGAAGGGTCTTGCGAAGGATAGTGGGATTGTGCGTCATCCCTTACGTCAGTGGAGATATCACATCAATC

CACTTGCTTTGAAGACGTGGTTGGAACGTCTTCTTTTTCCACGATGCTCCTCGTGGGTGGGGGTCCATCTTTGGGAC

CACTGTCGGCAGAGGCATCTTGAACGATAGCCTTTCCTTTATCGCAATGATGGCATTTGTAGGTGCCACCTTCCTTT

TCTACTGTCCTTTTGATGAAGTGACAGATAGCTGGGCAATGGAATCCGAGGAGGTTTCCCGATATTACCCTTTGTTG

AAAAGTCTCAATAGCCCTTTGGTCTTCTGAGACTGTATCTTTGATATTCTTGGAGTAGACGAGAGTGTCGTGCTCCA

CCATGTTCACATCAATCCACTTGCTTTGAAGACGTGGTTGGAACGTCTTCTTTTTCCACGATGCTCCTCGTGGGTGG
```

-continued

```
GGGTCCATCTTTGGGACCACTGTCGGCAGAGGCATCTTGAACGATAGCCTTTCCTTTATCGCAATGATGGCATTTGT

AGGTGCCACCTTCCTTTTCTACTGTCCTTTTGATGAAGTGACAGATAGCTGGGCAATGGAATCCGAGGAGGTTTCCC

GATATTACCCTTTGTTGAAAAGTCTCAATAGCCCTTTGGTCTTCTGAGACTGTATCTTTGATATTCTTGGAGTAGAC

GAGAGTGTCGTGCTCCACCATGTTGGCCAACTTTTCTATACAAAGTTG
```

In some embodiments, a vector of the present disclosure (e.g., a plasmid) is useful for delivering a heme-producing gene and a male-sterility gene to a plant cell (e.g., a tomato cell or an eggplant cell).

Figure 6:
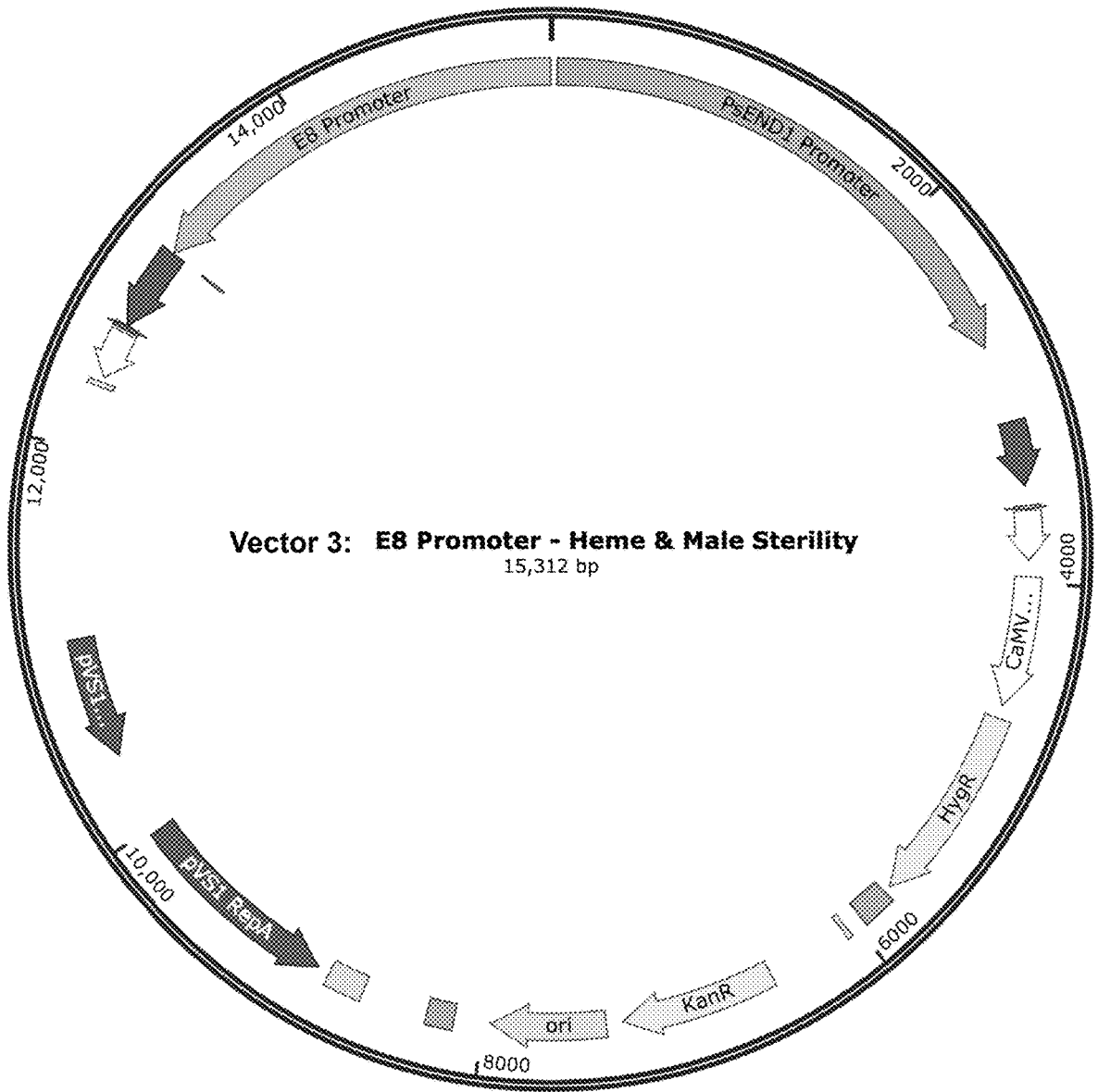
FIG. 6 is a plasmid map depicting a codon-optimized leghemoglobin gene under control of an E8S promoter and a NOS terminator, a barnase gene under control of a Pisum sativum Endothecium 1 (PSEND1) promoter and a NOS terminator, and a hygromycin resistance gene under control of a CaMV 35S promoter and a CaMV polyA termination signal.

A non-limiting example of a vector comprising a codon-optimized heme-producing gene flanked by a plant promoter (e.g., E8 promoter) and a NOS terminator, a male-sterility gene (e.g., a barnase gene) flanked by a *Pisum sativum* Endothecium 1 (PSEND1) promoter and a NOS terminator, a hygromycin resistance gene under control of a CaMV 35S promoter and a CaMV polyA termination signal, and a left border (LB) T-DNA repeat and a right border (RB) T-DNA repeat is shown in FIG. 6 and provided as SEQ ID NO: 3:

(SEQ ID NO: 3)

```
AGCTTGCATGCCTGCAGGTCGACTCTAGAGGATCGACTTCAACCTTATTAGTGAATGGACAATAAAGGTTATAAGCT

CCTTTACTGTGAAAGCCCACCAGTAACATCACCTTGCTTATATCATTCAGCTTCTTTCTAGTAACATTTGGAACGTG

TTTATAACAGAAAAAAACCCAAAAACTCTGAAAAGACTCACACTTTTCTTATCTCCAGTCCACCTCTCAAAAGGAAC

AATTTCCTTCAGCTTCTTGGTTGGACACCTGTTGAGCACATATGCTGCAGTGGCAACAGTTTCTCCCCACAAAGTGT

TAGGAAGCTTCTTCTCCTTCAGCATGTTCCTTGTCATATCAAGCAAAGTTCGGTTTTCAACAAGACCATTATGTTGA

GGAGTATATGGATCAGTCACTTCATGCTCAATTCCATTCTCTTTACAGAACTTCTTGAACTCTGTAGAGTTATACTC

ACCTCCACCATCAGTTCTGAGAATCTTCAGAAGTCTGACCACTTTATTTCTCAGCCTTGATTATGAATTTCTTAAAT

TCAGCAAACACCTCGTGTTTGAATTTTATAAGGGATACCCATGTCATCCTTGTGAACTCATCCATAAATGACATAAA

GTATTATTCCCTCCTAGTGAAAGGTTTGTAATGGGCCACACACATAAGAATGCACTACTCCTAAAGCATGTTTTGCT

CTTTGAGCTACTTTTGATGAAAATGGCAGTCTTGGTTGCTTCCCTTTCATGCACACATTACATGACTTTTTTGGTTT

CTTAATTGTAGGAATTCCACGTACCAGTTTCTTTGAATTCAAATTCCCTAAGCTCCTAAAGTTCAAATGACCAAATC

TTTTGTTCCACAACTCACTTTCCTTCACAACACTTGTTGCGCTAAGGCATTCAGAGTCTGCAGTTTTAACATTCGCC

TTGAATGTTTTACTCCTTCCATGTTCTGACTCCATAATCAACTTCTGATAACAGTCATACAGCTTCAAAAGAATGTC

ATTCATGGTAACTGGAAATCCCTTTTCAATTAATTGACCTACACTCATCAGATTGCTCTTCATGCCAAGAACGTACC

AAGACGTTCTGAATTAATGCAGATTTTCTATTATTCATAATCACTCTAACATTCCCCATTCCTTTAGCATTTAGTTA

CTTATCATCAGCACATCTAATCTTGGTTTTCTTCCTAGAGTCAAAATCAACCAGCCATTTCTTATTTCCAGTATGAT

GGTTTGAACAACCAGTGTCCATATATCACCAGTCTTCTATAGACGCACTATCATAACTAGAAGCCATTAATAGCACA

TGTTCATCATGGTGCTCAGATCCTTAGAATGTTCAATTGCTACAACGATGTAATCAAACTGATGAGTAAGAGATCTA

AGTACCTTCTCAATGATACTTTCCTCATAAAGAGTTTCTCCATGCGACTTCATCTCATTTGTGATCAGAATCACTCT

AGAGATGTAGTCAGATAACTTCTCATTGTTCTTCATGCTTAGATTCTCATACTGCTCACGTAGAGACTGAAGTTTCA

CCTTCTACACTGATGCATCACTATCGTAGCACCACACCAGTCTGTCTCACACAACCTTTTCCGTCATTGAATCAACG

ATTTTCTTAAACACGTTCACATCCACACACTGATGGATGTAGAACAACGCATTCTGATCCTTCTTCCTCATATCACA

CTGAGCATTTCTTTGCGCATCCGTTGCATTTTCTAGAAGTGAAGCATAAACTTCGTTGATGAGATCAAGAACATCTT

GAGCACCAAATAACACACACATCTGAATCATCCAACGATTCCAGTTGTTGTCGTCGAACAATGGNAGCNTGGTGCAC

AGATTCACAACGATATATTATAANTTTTGTTTTATGAAATTTAAGAACAAATTTCCATTATTCTTAAAATGTTTACA

CACTGATGTAGACTGCAAAAGGAATAAAGATACAATTTGTTCACACCACTCACTTGCGTAAATATAAGTGAGAGTTA

ATGAGAAATACTAAAATACCCTCTAAAATTATGAATTAATTCTAACAATCTCTAATGTTAGTATAATCCATTAAACA

CTTTGATGGCAGGTATAACAAGGGTGTAAGTTAGTGTATACATATTAGGCTCTTATTATTTTTATATTATCTCTGCT

TTTCTTCTTCATGTTCTCACTAATATGATATTATCTCCCTTCCCTAAATTATTTATATTTATTAGAAAAAGAGTTTC

ATTTTTTAAAAATATATTACCGTAATTTTTCAAAAAATAAAATTTAAATATATTTTATAAAAAAATTATTTAATAAT
```

-continued

```
TTATTTACATTAATGCATAAATATAAATAAATACTGTCATTTAATATTTAACCTTTTAACAATAAATTATATTTATT

TAATTCAACTAATATAAGCTAAGTTATCTCATCCAACCAATTAAAAAGATCATTTGAAAATACCTTTTTATTTAGTT

TGTGGCGGTTTCAACTGTCAAAAAAAAGGAATTTTTACGACGATATAAATTTAAACCAGCAAAAAATTGAAGCAGTT

AAGCGAACCAACTCATGGTATGTGGATATATTTATCTTTGTCGTTTATATCGGATTCGAATCTCTATAATGATGAAA

AATTAATATCAAACTTTAAATAAGAACGTCATTTATAGAGCCATTTTGGGAAACACATATTTCATGTACACGTGATT

CGCAAATTTCCAATAACTCTATATATAGCCCTCCTCAGTTTCATGCATTTGCTCACAACATAACCTTCCTTGAATCT

GGAAAACGTCACATTGCTTCCGCATATCGGGTCAGCAACGGCTAAAATCCGCTTGAATATGTTCACACAAGCCGCTC

AAAACATGATTGACGCCGTATACGGAAGAACGCCGAAAAACCTTACTAAGGAATTTCAATAAGAAGAAAAATCCCGG

TTGGTTCAGCCGGGGTTTATTTTTCGCTAGATAAAAAGTACTATTTTTAAATTCTTTCTATTCCTTTCTTTCGTTGC

TGATACAATGAAAAGGAATCAGCTTCACATGATGAAAATGGGAGGTATTGCTTTGAAAAAACGATTATCGTGGATTT

CCGTTTGTTTACTGGTGCTTGTCTCCGCGGCGGGGATGCTGTTTTCAACAGCTGCCAAAACGGAAACATCTTCTCAC

AAGGCACACACAGAAGCACAGGTTATCAACACGTTTGACGGGGTTGCGGATTATCTTCAGACATATCATAAGCTACC

TGATAATTACATTACAAAATCAGAAGCACAAGCCCTCGGCTGGGTGGCATCAAAAGGGAACCTTGCAGACGTCGCTC

CGGGGAAAAGCATCGGCGGAGACATCTTCTCAAACAGGGAAGGCAAACTCCCGGGCAAAAGCGGACGAACATGGCGT

GAAGCGGATATTAACTATACATCAGGCTTCAGAAATTCAGACCGGATTCTTTACTCAAGCGACTGGCTGATTTACAA

AACAACGGACCATTATCAGACCTTTACAAAAATCAGATAACGAAAAAAACGGCTTCCCTGCGGAGGCCGTTTTTTTC

AGCTTTACATAAAGTGTGTAATAAATTTTTCTTCAAACTCTGATCGGTCAATTTCACTTTGCTAGCCACCACCACCA

CCACCACGTGTGAGATCGTTCAAACATTTGGCAATAAAGTTTCTTAAGATTGAATCCTGTTGCCGGTCTTGCGATGA

TTATCATATAATTTCTGTTGAATTACGTTAAGCATGTAATAATTAACATGTAATGCATGACGTTATTTATGAGATGG

GTTTTTATGATTAGAGTCCCGCAATTATACATTTAATACGCGATAGAAAACAAAATATAGCGCGCAAACTAGGATAA

ATTATCGCGCGCGGTGTCATCTATGTTACTAGATCCCGGGTACGCCAACATGGTGGAGCACGACACTCTCGTCTACT

CCAAGAATATCAAAGATACAGTCTCAGAAGACCAAAGGGCTATTGAGACTTTTCAACAAAGGGTAATATCGGGAAAC

CTCCTCGGATTCCATTGCCCAGCTATCTGTCACTTCATCAAAAGGACAGTAGAAAAGGAAGGTGGCACCTACAAATG

CCATCATTGCGATAAAGGAAAGGCTATCGTTCAAGATGCCTCTGCCGACAGTGGTCCCAAAGATGGACCCCCACCCA

CGAGGAGCATCGTGGAAAAAGAAGACGTTCCAACCACGTCTTCAAAGCAAGTGGATTGATGTGAACATGGTGGAGCA

CGACACTCTCGTCTACTCCAAGAATATCAAAGATACAGTCTCAGAAGACCAAAGGGCTATTGAGACTTTTCAACAAA

GGGTAATATCGGGAAACCTCCTCGGATTCCATTGCCCAGCTATCTGTCACTTCATCAAAAGGACAGTAGAAAAGGAA

GGTGGCACCTACAAATGCCATCATTGCGATAAAGGAAAGGCTATCGTTCAAGATGCCTCTGCCGACAGTGGTCCCAA

AGATGGACCCCCACCCACGAGGAGCATCGTGGAAAAAGAAGACGTTCCAACCACGTCTTCAAAGCAAGTGGATTGAT

GTGATATCTCCACTGACGTAAGGGATGACGCACAATCCCACTATCCTTCGCAAGACCCTTCCTCTATATAAGGAAGT

TCATTTCATTTGGAGAGGACACGCTGAAATCACCAGTCTCTCTCTACAAATCTATCTCTCTCGAGCTTTCGCAGATC

CGGGGGGCAATGAGATATGAAAAAGCCTGAACTCACCGCGACGTCTGTCGAGAAGTTTCTGATCGAAAAGTTCGACA

GCGTCTCCGACCTGATGCAGCTCTCGGAGGGCGAAGAATCTCGTGCTTTCAGCTTCGATGTAGGAGGGCGTGGATAT

GTCCTGCGGGTAAATAGCTGCGCCGATGGTTTCTACAAAGATCGTTATGTTTATCGGCACTTTGCATCGGCCGCGCT

CCCGATTCCGGAAGTGCTTGACATTGGGGAGTTTAGCGAGAGCCTGACCTATTGCATCTCCCGCCGTTCACAGGGTG

TCACGTTGCAAGACCTGCCTGAAACCGAACTGCCCGCTGTTCTACAACCGGTCGCGGAGGCTATGGATGCGATCGCT

GCGGCCGATCTTAGCCAGACGAGCGGGTTCGGCCCATTCGGACCGCAAGGAATCGGTCAATACACTACATGGCGTGA

TTTCATATGCGCGATTGCTGATCCCCATGTGTATCACTGGCAAACTGTGATGGACGACACCGTCAGTGCGTCCGTCG

CGCAGGCTCTCGATGAGCTGATGCTTTGGGCCGAGGACTGCCCCGAAGTCCGGCACCTCGTGCACGCGGATTTCGGC

TCCAACAATGTCCTGACGGACAATGGCCGCATAACAGCGGTCATTGACTGGAGCGAGGCGATGTTCGGGGATTCCCA
```

-continued

```
ATACGAGGTCGCCAACATCTTCTTCTGGAGGCCGTGGTTGGCTTGTATGGAGCAGCAGACGCGCTACTTCGAGCGGA

GGCATCCGGAGCTTGCAGGATCGCCACGACTCCGGGCGTATATGCTCCGCATTGGTCTTGACCAACTCTATCAGAGC

TTGGTTGACGGCAATTTCGATGATGCAGCTTGGGCGCAGGGTCGATGCGACGCAATCGTCCGATCCGGAGCCGGGAC

TGTCGGGCGTACACAAATCGCCCGCAGAAGCGCGGCCGTCTGGACCGATGGCTGTGTAGAAGTACTCGCCGATAGTG

GAAACCGACGCCCCAGCACTCGTCCGAGGGCAAAGAAATAGAGTAGATGCCGACCGGGATCTGTCGATCGACAAGCT

CGAGTTTCTCCATAATAATGTGTGAGTAGTTCCCAGATAAGGGAATTAGGGTTCCTATAGGGTTTCGCTCATGTGTT

GAGCATATAAGAAACCCTTAGTATGTATTTGTATTTGTAAAATACTTCTATCAATAAAATTTCTAATTCCTAAAACC

AAAATCCAGTACTAAAATCCAGATCCCCCGGTACCGAGCTCGAATTCAATTCGGCGTTAATTCAGTACATTAAAAAC

GTCCGCAATGTGTTATTAAGTTGTCTAAGCGTCAATTTGTTTACACCACAATATATCCTGCCACCAGCCAGCCAACA

GCTCCCCGACCGGCAGCTCGGCACAAAATCACCACTCGATACAGGCAGCCCATCAGTCCGGGACGGCGTCAGCGGGA

GAGCCGTTGTAAGGCGGCAGACTTTGCTCATGTTACCGATGCTATTCGGAAGAACGGCAACTAAGCTGCCGGGTTTG

AAACACGGATGATCTCGCGGAGGGTAGCATGTTGATTGTAACGATGACAGAGCGTTGCTGCCTGTGATCACCGCGGT

TTCAAAATCGGCTCCGTCGATACTATGTTATACGCCAACTTTGAAAACAACTTTGAAAAAGCTGTTTTCTGGTATTT

AAGGTTTTAGAATGCAAGGAACAGTGAATTGGAGTTCGTCTTGTTATAATTAGCTTCTTGGGGTATCTTTAAATACT

GTAGAAAAGAGGAAGGAAATAATAAATGGCTAAAATGAGAATATCACCGGAATTGAAAAAACTGATCGAAAAATACC

GCTGCGTAAAAGATACGGAAGGAATGTCTCCTGCTAAGGTATATAAGCTGGTGGGAGAAAATGAAAACCTATATTTA

AAAATGACGGACAGCCGGTATAAAGGGACCACCTATGATGTGGAACGGGAAAAGGACATGATGCTATGGCTGGAAGG

AAAGCTGCCTGTTCCAAAGGTCCTGCACTTTGAACGGCATGATGGCTGGAGCAATCTGCTCATGAGTGAGGCCGATG

GCGTCCTTTGCTCGGAAGAGTATGAAGATGAACAAAGCCCTGAAAAGATTATCGAGCTGTATGCGGAGTGCATCAGG

CTCTTTCACTCCATCGACATATCGGATTGTCCCTATACGAATAGCTTAGACAGCCGCTTAGCCGAATTGGATTACTT

ACTGAATAACGATCTGGCCGATGTGGATTGCGAAAACTGGGAAGAAGACACTCCATTTAAAGATCCGCGCGAGCTGT

ATGATTTTTTAAAGACGGAAAAGCCCGAAGAGGAACTTGTCTTTTCCCACGGCGACCTGGGAGACAGCAACATCTTT

GTGAAAGATGGCAAAGTAAGTGGCTTTATTGATCTTGGGAGAAGCGGCAGGGCGGACAAGTGGTATGACATTGCCTT

CTGCGTCCGGTCGATCAGGGAGGATATCGGGGAAGAACAGTATGTCGAGCTATTTTTTGACTTACTGGGGATCAAGC

CTGATTGGGAGAAAATAAAATATTATATTTTACTGGATGAATTGTTTTAGTACCTAGAATGCATGACCAAAATCCCT

TAACGTGAGTTTTCGTTCCACTGAGCGTCAGACCCCGTAGAAAAGATCAAAGGATCTTCTTGAGATCCTTTTTTTCT

GCGCGTAATCTGCTGCTTGCAAACAAAAAAACCACCGCTACCAGCGGTGGTTTGTTTGCCGGATCAAGAGCTACCAA

CTCTTTTTCCGAAGGTAACTGGCTTCAGCAGAGCGCAGATACCAAATACTGTCCTTCTAGTGTAGCCGTAGTTAGGC

CACCACTTCAAGAACTCTGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCGGTCGGGCTGAACGGGGG

GTTCGTGCACACAGCCCAGCTTGGAGCGAACGACCTACACCGAACTGAGATACCTACAGCGTGAGCTATGAGAAAGC

GCCACGCTTCCCGAAGGGAGAAAGGCGGACAGGTATCCGGTAAGCGGCAGGGTCGGAACAGGAGAGCGCACGAGGGA

GCTTCCAGGGGGAAACGCCTGGTATCTTTATAGTCCTGTCGGGTTTCGCCACCTCTGACTTGAGCGTCGATTTTTGT

GATGCTCGTCAGGGGGGCGGAGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTACCGCCTTTGAGTGAGCTGA

TACCGCTCGCCGCAGCCGAACGACCGAGCGCAGCGAGTCAGTGAGCGAGGAAGCGGAAGAGCGCCTGATGCGGTATT

TTCTCCTTACGCATCTGTGCGGTATTTCACACCGCATATGGTGCACTCTCAGTACAATCTGCTCTGATGCCGCATAG

TTAAGCCAGTATACACTCCGCTATCGCTACGTGACTGGGTCATGGCTGCGCCCCGACACCCGCCAACACCCGCTGAC

GCGCCCTGACGGGCTTGTCTGCTCCCGGCATCCGCTTACAGACAAGCTGTGACCGTCTCCGGGAGCTGCATGTGTCA

GAGGTTTTCACCGTCATCACCGAAACGCGCGAGGCAGGGTGCCTTGATGTGGGCGCCGGCGGTCGAGTGGCGACGGC

GCGGCTTGTCCGCGCCCTGGTAGATTGCCTGGCCGTAGGCCAGCCATTTTTTGAGCGGCCAGCGGCCGCGATAGGCCG
```

-continued

```
ACGCGAAGCGGCGGGGCGTAGGGAGCGCAGCGACCGAAGGGTAGGCGCTTTTTGCAGCTCTTCGGCTGTGCGCTGGC

CAGACAGTTATGCACAGGCCAGGCGGGTTTTAAGAGTTTTAATAAGTTTTAAAGAGTTTTAGGCGGAAAAATCGCCT

TTTTTCTCTTTTATATCAGTCACTTACATGTGTGACCGGTTCCCAATGTACGGCTTTGGGTTCCCAATGTACGGGTT

CCGGTTCCCAATGTACGGCTTTGGGTTCCCAATGTACGTGCTATCCACAGGAAAGAGACCTTTTCGACCTTTTTCCC

CTGCTAGGGCAATTTGCCCTAGCATCTGCTCCGTACATTAGGAACCGGCGGATGCTTCGCCCTCGATCAGGTTGCGG

TAGCGCATGACTAGGATCGGGCCAGCCTGCCCCGCCTCCTCCTTCAAATCGTACTCCGGCAGGTCATTTGACCCGAT

CAGCTTGCGCACGGTGAAACAGAACTTCTTGAACTCTCCGGCGCTGCCACTGCGTTCGTAGATCGTCTTGAACAACC

ATCTGGCTTCTGCCTTGCCTGCGGCGCGGCGTGCCAGGCGGTAGAGAAAACGGCCGATGCCGGGATCGATCAAAAAG

TAATCGGGGTGAACCGTCAGCACGTCCGGGTTCTTGCCTTCTGTGATCTCGCGGTACATCCAATCAGCTAGCTCGAT

CTCGATGTACTCCGGCCGCCCGGTTTCGCTCTTTACGATCTTGTAGCGGCTAATCAAGGCTTCACCCTCGGATACCG

TCACCAGGCGGCCGTTCTTGGCCTTCTTCGTACGCTGCATGGCAACGTGCGTGGTGTTTAACCGAATGCAGGTTTCT

ACCAGGTCGTCTTTCTGCTTTCCGCCATCGGCTCGCCGGCAGAACTTGAGTACGTCCGCAACGTGTGGACGGAACAC

GCGGCCGGGCTTGTCTCCCTTCCCTTCCCGGTATCGGTTCATGGATTCGGTTAGATGGGAAACCGCCATCAGTACCA

GGTCGTAATCCCACACACTGGCCATGCCGGCCGGCCCTGCGGAAACCTCTACGTGCCCGTCTGGAAGCTCGTAGCGG

ATCACCTCGCCAGCTCGTCGGTCACGCTTCGACAGACGGAAAACGGCCACGTCCATGATGCTGCGACTATCGCGGGT

GCCCACGTCATAGAGCATCGGAACGAAAAAATCTGGTTGCTCGTCGCCCTTGGGCGGCTTCCTAATCGACGGCGCAC

CGGCTGCCGGCGGTTGCCGGGATTCTTTGCGGATTCGATCAGCGGCCGCTTGCCACGATTCACCGGGGCGTGCTTCT

GCCTCGATGCGTTGCCGCTGGGCGGCCTGCGCGGCCTTCAACTTCTCCACCAGGTCATCACCCAGCGCCGCGCCGAT

TTGTACCGGGCCGGATGGTTTGCGACCGCTCACGCCGATTCCTCGGGCTTGGGGGTTCCAGTGCCATTGCAGGGCCG

GCAGGCAACCCAGCCGCTTACGCCTGGCCAACCGCCCGTTCCTCCACACATGGGGCATTCCACGGCGTCGGTGCCTG

GTTGTTCTTGATTTTCCATGCCGCCTCCTTTAGCCGCTAAAATTCATCTACTCATTTATTCATTTGCTCATTTACTC

TGGTAGCTGCGCGATGTATTCAGATAGCAGCTCGGTAATGGTCTTGCCTTGGCGTACCGCGTACATCTTCAGCTTGG

TGTGATCCTCCGCCGGCAACTGAAAGTTGACCCGCTTCATGGCTGGCGTGTCTGCCAGGCTGGCCAACGTTGCAGCC

TTGCTGCTGCGTGCGCTCGGACGGCCGGCACTTAGCGTGTTTGTGCTTTTGCTCATTTTCTCTTTACCTCATTAACT

CAAATGAGTTTTGATTTAATTTCAGCGGCCAGCGCCTGGACCTCGCGGGCAGCGTCGCCCTCGGGTTCTGATTCAAG

AACGGTTGTGCCGGCGGCGGCAGTGCCTGGGTAGCTCACGCGCTGCGTGATACGGGACTCAAGAATGGGCAGCTCGT

ACCCGGCCAGCGCCTCGGCAACCTCACCGCCGATGCGCGTGCCTTTGATCGCCCGCGACACGACAAAGGCCGCTTGT

AGCCTTCCATCCGTGACCTCAATGCGCTGCTTAACCAGCTCCACCAGGTCGGCGGTGGCCCATATGTCGTAAGGGCT

TGGCTGCACCGGAATCAGCACGAAGTCGGCTGCCTTGATCGCGGACACAGCCAAGTCCGCCGCCTGGGGCGCTCCGT

CGATCACTACGAAGTCGCGCCGGCCGATGGCCTTCACGTCGCGGTCAATCGTCGGGCGGTCGATGCCGACAACGGTT

AGCGGTTGATCTTCCCGCACGGCCGCCCAATCGCGGGCACTGCCCTGGGGATCGGAATCGACTAACAGAACATCGGC

CCCGGCGAGTTGCAGGGCGCGGGCTAGATGGGTTGCGATGGTCGTCTTGCCTGACCCGCCTTTCTGGTTAAGTACAG

CGATAACCTTCATGCGTTCCCCTTGCGTATTTGTTTATTTACTCATCGCATCATATACGCAGCGACCGCATGACGCA

AGCTGTTTTACTCAAATACACATCACCTTTTTAGACGGCGGCGCTCGGTTTCTTCAGCGGCCAAGCTGGCCGGCCAG

GCCGCCAGCTTGGCATCAGACAAACCGGCCAGGATTTCATGCAGCCGCACGGTTGAGACGTGCGCGGCGGCTCGAA

CACGTACCCGGCCGCGATCATCTCCGCCTCGATCTCTTCGGTAATGAAAAACGGTTCGTCCTGGCCGTCCTGGTGCG

GTTTCATGCTTGTTCCTCTTGGCGTTCATTCTCGGCGGCCGCCAGGGCGTCGGCCTCGGTCAATGCGTCCTCACGGA

AGGCACCGCGCCGCCTGGCCTCGGTGGGCGTCACTTCCTCGCTGCGCTCAAGTGCGCGGTACAGGGTCGAGCGATGC

ACGCCAAGCAGTGCAGCCGCCTCTTTCACGGTGCGGCCTTCCTGGTCGATCAGCTCGCGGGCGTGCGCGATCTGTGC

CGGGGTGAGGGTAGGGCGGGGGCCAAACTTCACGCCTCGGGCCTTGGCGGCCTCGCGCCCGCTCCGGGTGCGGTCGA
```

-continued

```
TGATTAGGGAACGCTCGAACTCGGCAATGCCGGCGAACACGGTCAACACCATGCGGCCGGCCGGCGTGGTGGTGTCG

GCCCACGGCTCTGCCAGGCTACGCAGGCCCGCGCCGGCCTCCTGGATGCGCTCGGCAATGTCCAGTAGGTCGCGGGT

GCTGCGGGCCAGGCGGTCTAGCCTGGTCACTGTCACAACGTCGCCAGGGCGTAGGTGGTCAAGCATCCTGGCCAGCT

CCGGGCGGTCGCGCCTGGTGCCGGTGATCTTCTCGGAAAACAGCTTGGTGCAGCCGGCCGCGTGCAGTTCGGCCCGT

TGGTTGGTCAAGTCCTGGTCGTCGGTGCTGACGCGGGCATAGCCCAGCAGGCCAGCGGCGGCGCTCTTGTTCATGGC

GTAATGTCTCCGGTTCTAGTCGCAAGTATTCTACTTTATGCGACTAAAACACGCGACAAGAAAACGCCAGGAAAAGG

GCAGGGCGGCAGCCTGTCGCGTAACTTAGGACTTGTGCGACATGTCGTTTTCAGAAGACGGCTGCACTGAACGTCAG

AAGCCGACTGCACTATAGCAGCGGAGGGGTTGGATCAAAGTACTTTGATCCCGAGGGGAACCCTGTGGTTGGCATGC

ACATACAAATGGACGAACGGATAAACCTTTTCACGCCCTTTTAAATATCCGATTATTCTAATAAACGCTCTTTTCTC

TTAGGTTTACCCGCCAATATATCCTGTCAAACACTGATAGTTTAAAAGCTTTCCCGATCTAGTAACATAGATGACAC

CGCGCGCGATAATTTATCCTAGTTTGCGCGCTATATTTTGTTTTCTATCGCGTATTAAATGTATAATTGCGGGACTC

TAATCATAAAAACCCATCTCATAAATAACGTCATGCATTACATGTTAATTATTACATGCTTAACGTAATTCAACAGA

AATTATATGATAATCATCGCAAGACCGGCAACAGGATTCAATCTTAAGAAACTTTATTGCCAAATGTTTGAACGATC

GGGGAAATTCGAGCTACCACTTTGTACAAGAAAGCTGGGTTTAAGCCTTCTTGATAGCAGCAGCGAGTTCATCGTAA

GCAACTTCCCAAGCCCTAGACAATTCATCTGACCATTTATCACCAACAGCAGCTTTAATAGTTTTAAGCAAAGCTTC

TTTCACAACAACGAACTGAGGATCTGTAACAGCCTTTTGAGCATGAACTGAACCCAAAGCAGCATCAGCAACAACTG

TCCCAGAAGCTTTAAGCTGACCAGCTGAATCTCTCACCAGAGCAAAAAGCTTTTCTGCATGTCCAGTCAACTTAGGA

TTTGTTGGATCAACACCGTTAGCCAAAAATGAAAACAAATCCTTAGCAGCAGGAGCTTTTTCCAAAATTGATGTGTA

GAAAACCACAGAATATTGTGGAATATTTGCCTTGAAAGCTTCAAATGATGATGAAACAAGAGCATCTTGCTTTTCAG

TAAAAGCAACCATGGTGGCGGATCCCTTCTTTTGCACTGTGAATGATTAGAATAATTTCTAAAAATCTCAATATGAG

GATGCCATATTTATAATAGAATAAAATAAAATGTGAACAAAGAAAGAGATAAAGTAGTTCACTTTTTGAAATCTAAG

AGAGAAATGGGAACAAGAAAGAGACAAAGTAGTTTCAAACAAACTTCTCTTCTAAGTTTAGTCCCTTTTTAAAATA

TGAAACCCAATACGTCTGATTAAGAATAGAAAAATATCAAATTTTCAATATAATTTATACTAATCGTTTTGAATTTT

TCATACTGATATAGTGTACGTTTCATCATAACAACCAAAACGTTGTTGTTTCACAACAATAATATAGTAGTAGTTAA

TTTATTATTTAGTAATAAGTGGTCCTAAAAATTAGATAAATATTACTATGATAATATAAAAATATTTGAGTCAGTCC

TAAAAAATTATTTAGTATTCATACATGAATCAAACTAATTAGTTAAGTGTCAACAATTGGACAAGTGGCATGGAGGT

TGTAAAAGAATGACATAAGCCAACTGCTATTTTTATCCAAAAAAAAGAAGACAACTTGACAACTACATTTCTTTTAT

TTTTATAAATTTACTAATATCTTCTATGCAAAATTATTCGGTGCCTTTCTAAACTTTAAGGTTTTTATTTGATGTAC

ACCTAAATTATATTTTATTTTAATCACTTCACTGAACTTGTTTATTCCTTCATCATATACACCTACTCCTATTATGA

CTACAAGTTGGCAAAAGTAATGATATGAATTTCTACTTAAATAAATAATAGTCACCTAGATAAATTAATTTAACAAA

AGATAAATATCAAACCTTCTCACCTAAAATTTTGAGCAAAACTTCTCACTAAAACTTGTGGACTAAACCCGAAAATC

TTCAGAAAATTAATATTTAGTACTGGAAAAGTCAGATTAAATGTCTGCACAAGACTTTCTATTGTTGGGAATAAACA

AATTAATATTGGATTAAAAATAGTTGAAATATTTAGGTAAAATGCTACATGTCATTTATTCATTGGAAATTATTTCTT

AAAATTTAAAATTCATTATTTAAAAGTTATTTTTGAAAAAGGGCCGATTTCTGAAATTCCTTCTAAGATAGGGTCTT

TCTAGACGTAAAGTTGATCTATTAAATTTTAAATTTATCTTAAATTCTTACAAAGTAAGTATTAATCTTTGTTTCCT

TTACTATTCATTTACATTTTGTCCTATATTTCGTTTAAAATATGTCATATATTAAAAAAAAATTAAAAATTTTACTTT

CTTTTTTTACGTTATAGCTATATGACGTGACAAAAAATCAACTTTCACATGCGCCTAGTAGACTTCAAGTTAAAAGG

GGATAATGGATACTTTGCCTATCTTTTACCATATATTTTAAAATCCTTAATTATTAAGTTTTCCAATATCTCTCACC

ATTCATTTTCTCCTATCATATATTTTAGGAGTCCTTAATAATTAAGTTTACTAATAAACTTTATTATATATTATAGG

ACTCCTCAATTATTAGTTCTCTTTATGTCTCTCATCGTACATTTTCCTCTTGTCTTATTTGTTAGGACACTTGAAAT

TTTCAAAATATATTTTGCTTTTAATATATGAAGTTGTGTTTGATTGTAGTTTTTGTAAATATATTTAATTTTTTGAA
```

-continued

TTTTTATTTTCTAAAAGAAACATAAAATTTAAAAGATTTAAAAGTATCATTAAACTATTAGAAATAATATATCTATG

TTGTTAAAAATGATGGTTCTTAATTAACTGTTTTATTATAAAATATCAGATAATTCGTTTTATTTACGCAAAAGTTA

AGTGAAGTAACGAAATTATAAATCCCATAGAATATTGTGTATATACTTGGCACATGATGATTGTAACATCCTTAATT

ATTATTAATTCATCGAACCTATTATTTCTTCATTGTCTATGTACATTTATCCTTAATAATTCCACTTCAGGATTTAT

TAGTTCTTTGGTTATTGGTTTAAGTTTATTTTACAACCAAGTGAATTGAATTTGTCCTCCATTAATATTTATTGGAT

TAAAAAATAAATAAATTTGCTCTTATTTGTAGAAAGATTTAGACTTTTAAAATATTACGTTTTCTGACTCTTTTCTT

ATCAAAATTGGACTCTCTCACTTCCACAAAACTTAATTACATGAACAATATCATTAGGGAAAGCTT

Figure 7:
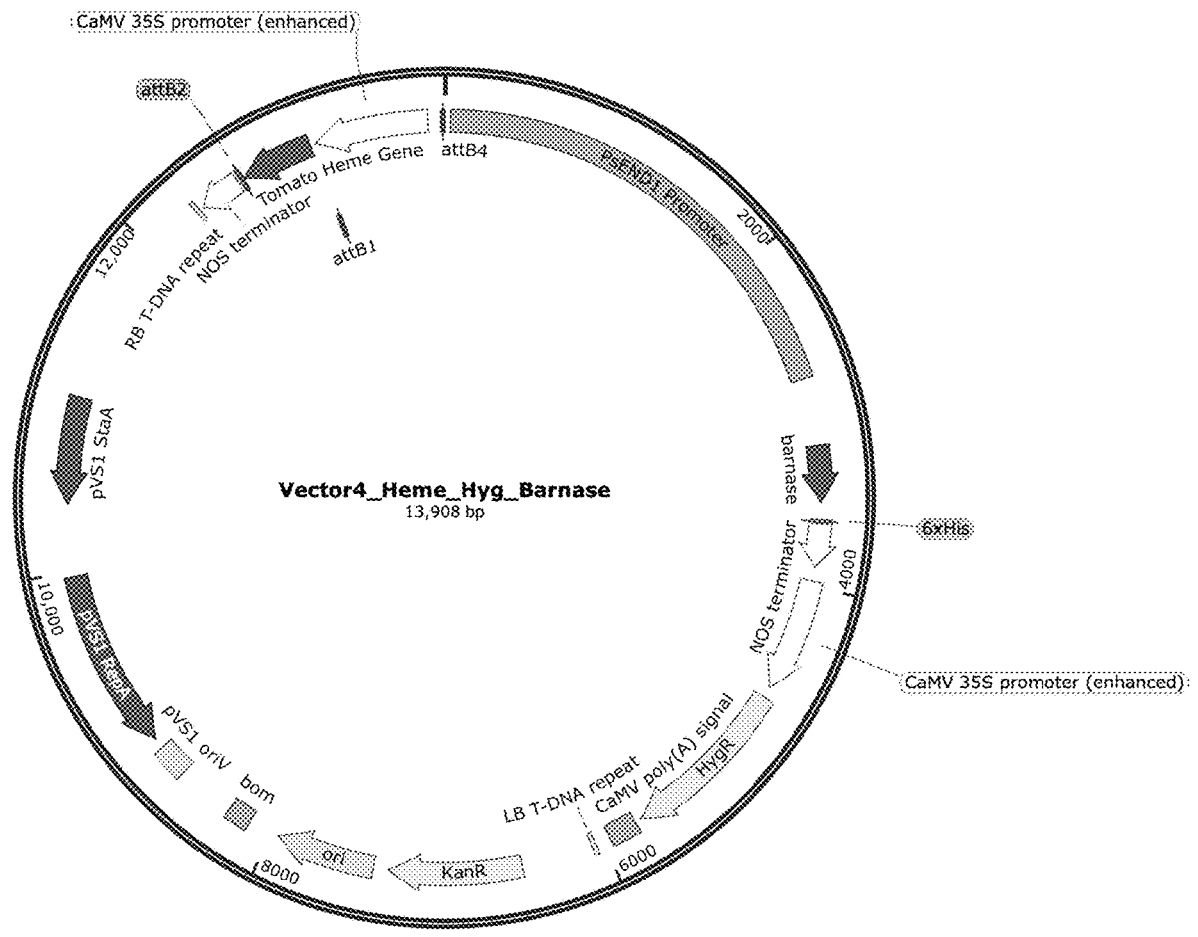
FIG. 7 is a plasmid map depicting a codon-optimized leghemoglobin gene under control of a CaMV 35S promoter and a NOS terminator, a barnase gene under control of a PSEND1 promoter and a NOS terminator, and a hygromycin resistance gene under control of a CaMV 35S promoter and a CaMV polyA termination signal.

A non-limiting example of a vector comprising a codon-optimized heme-producing gene flanked by a CaMV 35S promoter and a NOS terminator, a male-sterility gene (e.g., a barnase gene) flanked by a *Pisum sativum* Endothecium 1 (PSEND1) promoter and a NOS terminator, a hygromycin resistance gene under control of a CaMV 35S promoter and a CaMV polyA termination signal, and a left border (LB) T-DNA repeat and a right border (RB) T-DNA repeat is shown in FIG. 7 and provided as SEQ ID NO: 4:

(SEQ ID NO: 4)

AGCTTGCATGCCTGCAGGTCGACTCTAGAGGATCGACTTCAACCTTATTAGTGAATGGACAATAAAGGTTATAAGCT

CCTTTACTGTGAAAGCCCACCAGTAACATCACCTTGCTTATATCATTCAGCTTCTTTCTAGTAACATTTGGAACGTG

TTTATAACAGAAAAAAACCCAAAAACTCTGAAAAGACTCACACTTTTCTTATCTCCAGTCCACCTCTCAAAAGGAAC

AATTTCCTTCAGCTTCTTGGTTGGACACCTGTTGAGCACATATGCTGCAGTGGCAACAGTTTCTCCCCACAAAGTGT

TAGGAAGCTTCTTCTCCTTCAGCATGTTCCTTGTCATATCAAGCAAAGTTCGGTTTTCAACAAGACCATTATGTTGA

GGAGTATATGGATCAGTCACTTCATGCTCAATTCCATTCTCTTTACAGAACTTCTTGAACTCTGTAGAGTTATACTC

ACCTCCACCATCAGTTCTGAGAATCTTCAGAAGTCTGACCACTTTATTTCTCAGCCTTGATTATGAATTTCTTAAAT

TCAGCAAACACCTCGTGTTTGAATTTTATAAGGGATACCCATGTCATCCTTGTGAACTCATCCATAAATGACATAAA

GTATTATTCCCTCCTAGTGAAAGGTTTGTAATGGGCCACACACATAAGAATGCACTACTCCTAAAGCATGTTTTGCT

CTTTGAGCTACTTTTGATGAAAATGGCAGTCTTGGTTGCTTCCCTTTCATGCACACATTACATGACTTTTTTGGTTT

CTTAATTGTAGGAATTCCACGTACCAGTTTCTTTGAATTCAAATTCCCTAAGCTCCTAAAGTTCAAATGACCAAATC

TTTTGTTCCACAACTCACTTTCCTTCACAACACTTGTTGCGCTAAGGCATTCAGAGTCTGCAGTTTTAACATTCGCC

TTGAATGTTTTACTCCTTCCATGTTCTGACTCCATAATCAACTTCTGATAACAGTCATACAGCTTCAAAAGAATGTC

ATTCATGGTAACTGGAAATCCCTTTTCAATTAATTGACCTACACTCATCAGATTGCTCTTCATGCCAAGAACGTACC

AAGACGTTCTGAATTAATGCAGATTTTCTATTATTCATAATCACTCTAACATTCCCCATTCCTTTAGCATTTAGTTA

CTTATCATCAGCACATCTAATCTTGGTTTTCTTCCTAGAGTCAAAATCAACCAGCCATTTCTTATTTCCAGTATGAT

GGTTTGAACAACCAGTGTCCATATATCACCAGTCTTCTATAGACGCACTATCATAACTAGAAGCCATTAATAGCACA

TGTTCATCATGGTGCTCAGATCCTTAGAATGTTCAATTGCTACAACGATGTAATCAAACTGATGAGTAAGAGATCTA

AGTACCTTCTCAATGATACTTTCCTCATAAAGAGTTTCTCCATGCGACTTCATCTCATTTGTGATCAGAATCACTCT

AGAGATGTAGTCAGATAACTTCTCATTGTTCTTCATGCTTAGATTCTCATACTGCTCACGTAGAGACTGAAGTTTCA

CCTTCTACACTGATGCATCACTATCGTAGCACCACACCAGTCGTCTCACACAACCTTTTCCGTCATTGAATCAACG

ATTTTCTTAAACACGTTCACATCCACACACTGATGGATGTAGAACAACGCATTCTGATCCTTCTTCCTCATATCACA

CTGAGCATTTCTTTGCGCATCCGTTGCATTTTCTAGAAGTGAAGCATAAACTTCGTTGATGAGATCAAGAACATCTT

GAGCACCAAATAACACACATCTGAATCATCCAACGATTCCAGTTGTTGTCGTCGAACAATGGNAGCNTGGTGCAC

AGATTCACAACGATATATTATAANTTTTGTTTTATGAAATTTAAGAACAAATTTCCATTATTCTTAAAATGTTTACA

CACTGATGTAGACTGCAAAAGGAATAAAGATACAATTTGTTCACACCACTCACTTGCGTAAATATAAGTGAGAGTTA

ATGAGAAATACTAAAATACCCTCTAAAATTATGAATTAATTCTAACAATCTCTAATGTTAGTATAATCCATTAAACA

CTTTGATGGCAGGTATAACAAGGGTGTAAGTTAGTGTATACATATTAGGCTCTTATTATTTTTATATTATCTCTGCT

-continued

```
TTTCTTCTTCATGTTCTCACTAATATGATATTATCTCCCTTCCCTAAATTATTTATATTTATTAGAAAAAGAGTTTC

ATTTTTTAAAAATATATTACCGTAATTTTTCAAAAAATAAAATTTAAATATATTTTATAAAAAAATTATTTAATAAT

TTATTTACATTAATGCATAAATATAAATAAATACTGTCATTTAATATTTAACCTTTTAACAATAAATTATATTTATT

TAATTCAACTAATATAAGCTAAGTTATCTCATCCAACCAATTAAAAAGATCATTTGAAAATACCTTTTTATTTAGTT

TGTGGCGGTTTCAACTGTCAAAAAAAAGGAATTTTTACGACGATATAAATTTAAACCAGCAAAAAATTGAAGCAGTT

AAGCGAACCAACTCATGGTATGTGGATATATTTATCTTTGTCGTTTATATCGGATTCGAATCTCTATAATGATGAAA

AATTAATATCAAACTTTAAATAAGAACGTCATTTATAGAGCCATTTTGGGAAACACATATTTCATGTACACGTGATT

CGCAAATTTCCAATAACTCTATATATAGCCCTCCTCAGTTTCATGCATTTGCTCACAACATAACCTTCCTTGAATCT

GGAAAACGTCACATTGCTTCCGCATATCGGGTCAGCAACGGCTAAAATCCGCTTGAATATGTTCACACAAGCCGCTC

AAAACATGATTGACGCCGTATACGGAAGAACGCCGAAAAACCTTACTAAGGAATTTCAATAAGAAGAAAAATCCCGG

TTGGTTCAGCCGGGGTTTATTTTTCGCTAGATAAAAAGTACTATTTTTAAATTCTTTCTATTCCTTTCTTTCGTTGC

TGATACAATGAAAAGGAATCAGCTTCACATGATGAAAATGGGAGGTATTGCTTTGAAAAAACGATTATCGTGGATTT

CCGTTTGTTTACTGGTGCTTGTCTCCGCGGCGGGGATGCTGTTTTCAACAGCTGCCAAAACGGAAACATCTTCTCAC

AAGGCACACACAGAAGCACAGGTTATCAACACGTTTGACGGGGTTGCGGATTATCTTCAGACATATCATAAGCTACC

TGATAATTACATTACAAAATCAGAAGCACAAGCCCTCGGCTGGGTGGCATCAAAAGGGAACCTTGCAGACGTCGCTC

CGGGGAAAAGCATCGGCGGAGACATCTTCTCAAACAGGGAAGGCAAACTCCCGGGCAAAAGCGGACGAACATGGCGT

GAAGCGGATATTAACTATACATCAGGCTTCAGAAATTCAGACCGGATTCTTTACTCAAGCGACTGGCTGATTTACAA

AACAACGGACCATTATCAGACCTTTACAAAAATCAGATAACGAAAAAAACGGCTTCCCTGCGGAGGCCGTTTTTTTC

AGCTTTACATAAAGTGTGTAATAAATTTTTCTTCAAACTCTGATCGGTCAATTTCACTTTGCTAGCCACCACCACCA

CCACCACGTGTGAGATCGTTCAAACATTTGGCAATAAAGTTTCTTAAGATTGAATCCTGTTGCCGGTCTTGCGATGA

TTATCATATAATTTCTGTTGAATTACGTTAAGCATGTAATAATTAACATGTAATGCATGACGTTATTTATGAGATGG

GTTTTTATGATTAGAGTCCCGCAATTATACATTTAATACGCGATAGAAAACAAAATATAGCGCGCAAACTAGGATAA

ATTATCGCGCGCGGTGTCATCTATGTTACTAGATCCCGGGTACGCCAACATGGTGGAGCACGACACTCTCGTCTACT

CCAAGAATATCAAAGATACAGTCTCAGAAGACCAAAGGGCTATTGAGACTTTTCAACAAAGGGTAATATCGGGAAAC

CTCCTCGGATTCCATTGCCCAGCTATCTGTCACTTCATCAAAAGGACAGTAGAAAAGGAAGGTGGCACCTACAAATG

CCATCATTGCGATAAAGGAAAGGCTATCGTTCAAGATGCCTCTGCCGACAGTGGTCCCAAAGATGGACCCCCACCCA

CGAGGAGCATCGTGGAAAAAGAAGACGTTCCAACCACGTCTTCAAAGCAAGTGGATTGATGTGAACATGGTGGAGCA

CGACACTCTCGTCTACTCCAAGAATATCAAAGATACAGTCTCAGAAGACCAAAGGGCTATTGAGACTTTTCAACAAA

GGGTAATATCGGGAAACCTCCTCGGATTCCATTGCCCAGCTATCTGTCACTTCATCAAAAGGACAGTAGAAAAGGAA

GGTGGCACCTACAAATGCCATCATTGCGATAAAGGAAAGGCTATCGTTCAAGATGCCTCTGCCGACAGTGGTCCCAA

AGATGGACCCCCACCCACGAGGAGCATCGTGGAAAAAGAAGACGTTCCAACCACGTCTTCAAAGCAAGTGGATTGAT

GTGATATCTCCACTGACGTAAGGGATGACGCACAATCCCACTATCCTTCGCAAGACCCTTCCTCTATATAAGGAAGT

TCATTTCATTTGGAGAGGACACGCTGAAATCACCAGTCTCTCTCTACAAATCTATCTCTCTCGAGCTTTCGCAGATC

CGGGGGGCAATGAGATATGAAAAAGCCTGAACTCACCGCGACGTCTGTCGAGAAGTTTCTGATCGAAAAGTTCGACA

GCGTCTCCGACCTGATGCAGCTCTCGGAGGGCGAAGAATCTCGTGCTTTCAGCTTCGATGTAGGAGGGCGTGGATAT

GTCCTGCGGGTAAATAGCTGCGCCGATGGTTTCTACAAAGATCGTTATGTTTATCGGCACTTTGCATCGGCCGCGCT

CCCGATTCCGGAAGTGCTTGACATTGGGGAGTTTAGCGAGAGCCTGACCTATTGCATCTCCCGCCGTTCACAGGGTG

TCACGTTGCAAGACCTGCCTGAAACCGAACTGCCCGCTGTTCTACAACCGGTCGCGGAGGCTATGGATGCGATCGCT

GCGGCCGATCTTAGCCAGACGAGCGGGTTCGGCCCATTCGGACCGCAAGGAATCGGTCAATACACTACATGGCGTGA

TTTCATATGCGCGATTGCTGATCCCCATGTGTATCACTGGCAAACTGTGATGGACGACACCGTCAGTGCGTCCGTCG

CGCAGGCTCTCGATGAGCTGATGCTTTGGGCCGAGGACTGCCCCGAAGTCCGGCACCTCGTGCACGCGGATTTCGGC
```

-continued

```
TCCAACAATGTCCTGACGGACAATGGCCGCATAACAGCGGTCATTGACTGGAGCGAGGCGATGTTCGGGGATTCCCA

ATACGAGGTCGCCAACATCTTCTTCTGGAGGCCGTGGTTGGCTTGTATGGAGCAGCAGACGCGCTACTTCGAGCGGA

GGCATCCGGAGCTTGCAGGATCGCCACGACTCCGGGCGTATATGCTCCGCATTGGTCTTGACCAACTCTATCAGAGC

TTGGTTGACGGCAATTTCGATGATGCAGCTTGGGCGCAGGGTCGATGCGACGCAATCGTCCGATCCGGAGCCGGGAC

TGTCGGGCGTACACAAATCGCCCGCAGAAGCGCGGCCGTCTGGACCGATGGCTGTGTAGAAGTACTCGCCGATAGTG

GAAACCGACGCCCCAGCACTCGTCCGAGGGCAAAGAAATAGAGTAGATGCCGACCGGGATCTGTCGATCGACAAGCT

CGAGTTTCTCCATAATAATGTGTGAGTAGTTCCCAGATAAGGGAATTAGGGTTCCTATAGGGTTTCGCTCATGTGTT

GAGCATATAAGAAACCCTTAGTATGTATTTGTATTTGTAAAATACTTCTATCAATAAAATTTCTAATTCCTAAAACC

AAAATCCAGTACTAAAATCCAGATCCCCCGGTACCGAGCTCGAATTCAATTCGGCGTTAATTCAGTACATTAAAAAC

GTCCGCAATGTGTTATTAAGTTGTCTAAGCGTCAATTTGTTTACACCACAATATATCCTGCCACCAGCCAGCCAACA

GCTCCCCGACCGGCAGCTCGGCACAAAATCACCACTCGATACAGGCAGCCCATCAGTCCGGGACGGCGTCAGCGGGA

GAGCCGTTGTAAGGCGGCAGACTTTGCTCATGTTACCGATGCTATTCGGAAGAACGGCAACTAAGCTGCCGGGTTTG

AAACACGGATGATCTCGCGGAGGGTAGCATGTTGATTGTAACGATGACAGAGCGTTGCTGCCTGTGATCACCGCGGT

TTCAAAATCGGCTCCGTCGATACTATGTTATACGCCAACTTTGAAAACAACTTTGAAAAAGCTGTTTTCTGGTATTT

AAGGTTTTAGAATGCAAGGAACAGTGAATTGGAGTTCGTCTTGTTATAATTAGCTTCTTGGGGTATCTTTAAATACT

GTAGAAAAGAGGAAGGAAATAATAAATGGCTAAAATGAGAATATCACCGGAATTGAAAAAACTGATCGAAAAATACC

GCTGCGTAAAAGATACGGAAGGAATGTCTCCTGCTAAGGTATATAAGCTGGTGGGAGAAAATGAAAACCTATATTTA

AAAATGACGGACAGCCGGTATAAAGGGACCACCTATGATGTGGAACGGGAAAAGGACATGATGCTATGGCTGGAAGG

AAAGCTGCCTGTTCCAAAGGTCCTGCACTTTGAACGGCATGATGGCTGGAGCAATCTGCTCATGAGTGAGGCCGATG

GCGTCCTTTGCTCGGAAGAGTATGAAGATGAACAAAGCCCTGAAAAGATTATCGAGCTGTATGCGGAGTGCATCAGG

CTCTTTCACTCCATCGACATATCGGATTGTCCCTATACGAATAGCTTAGACAGCCGCTTAGCCGAATTGGATTACTT

ACTGAATAACGATCTGGCCGATGTGGATTGCGAAAACTGGGAAGAAGACACTCCATTTAAAGATCCGCGCGAGCTGT

ATGATTTTTTAAAGACGGAAAAGCCCGAAGAGGAACTTGTCTTTTCCCACGGCGACCTGGGAGACAGCAACATCTTT

GTGAAAGATGGCAAAGTAAGTGGCTTTATTGATCTTGGGAGAAGCGGCAGGGCGGACAAGTGGTATGACATTGCCTT

CTGCGTCCGGTCGATCAGGGAGGATATCGGGGAAGAACAGTATGTCGAGCTATTTTTTGACTTACTGGGGATCAAGC

CTGATTGGGAGAAAATAAAATATTATATTTTACTGGATGAATTGTTTTAGTACCTAGAATGCATGACCAAAATCCCT

TAACGTGAGTTTTCGTTCCACTGAGCGTCAGACCCCGTAGAAAAGATCAAAGGATCTTCTTGAGATCCTTTTTTTCT

GCGCGTAATCTGCTGCTTGCAAACAAAAAAACCACCGCTACCAGCGGTGGTTTGTTTGCCGGATCAAGAGCTACCAA

CTCTTTTTCCGAAGGTAACTGGCTTCAGCAGAGCGCAGATACCAAATACTGTCCTTCTAGTGTAGCCGTAGTTAGGC

CACCACTTCAAGAACTCTGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCGGTCGGGCTGAACGGGGG

GTTCGTGCACACAGCCCAGCTTGGAGCGAACGACCTACACCGAACTGAGATACCTACAGCGTGAGCTATGAGAAAGC

GCCACGCTTCCCGAAGGGAGAAAGGCGGACAGGTATCCGGTAAGCGGCAGGGTCGGAACAGGAGAGCGCACGAGGGA

GCTTCCAGGGGGAAACGCCTGGTATCTTTATAGTCCTGTCGGGTTTCGCCACCTCTGACTTGAGCGTCGATTTTTGT

GATGCTCGTCAGGGGGGCGGAGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTACCGCCTTTGAGTGAGCTGA

TACCGCTCGCCGCAGCCGAACGACCGAGCGCAGCGAGTCAGTGAGCGAGGAAGCGGAAGAGCGCCTGATGCGGTATT

TTCTCCTTACGCATCTGTGCGGTATTTCACACCGCATATGGTGCACTCTCAGTACAATCTGCTCTGATGCCGCATAG

TTAAGCCAGTATACACTCCGCTATCGCTACGTGACTGGGTCATGGCTGCGCCCCGACACCCGCCAACACCCGCTGAC

GCGCCCTGACGGGCTTGTCTGCTCCCGGCATCCGCTTACAGACAAGCTGTGACCGTCTCCGGGAGCTGCATGTGTCA
```

-continued

```
GAGGTTTTCACCGTCATCACCGAAACGCGCGAGGCAGGGTGCCTTGATGTGGGCGCCGGCGGTCGAGTGGCGACGGC

GCGGCTTGTCCGCGCCCTGGTAGATTGCCTGGCCGTAGGCCAGCCATTTTTGAGCGGCCAGCGGCCGCGATAGGCCG

ACGCGAAGCGGCGGGGCGTAGGGAGCGCAGCGACCGAAGGGTAGGCGCTTTTTGCAGCTCTTCGGCTGTGCGCTGGC

CAGACAGTTATGCACAGGCCAGGCGGGTTTTAAGAGTTTTAATAAGTTTTAAAGAGTTTTAGGCGGAAAAATCGCCT

TTTTTCTCTTTTATATCAGTCACTTACATGTGTGACCGGTTCCCAATGTACGGCTTTGGGTTCCCAATGTACGGGTT

CCGGTTCCCAATGTACGGCTTTGGGTTCCCAATGTACGTGCTATCCACAGGAAAGAGACCTTTTCGACCTTTTTCCC

CTGCTAGGGCAATTTGCCCTAGCATCTGCTCCGTACATTAGGAACCGGCGGATGCTTCGCCCTCGATCAGGTTGCGG

TAGCGCATGACTAGGATCGGGCCAGCCTGCCCCGCCTCCTCCTTCAAATCGTACTCCGGCAGGTCATTTGACCCGAT

CAGCTTGCGCACGGTGAAACAGAACTTCTTGAACTCTCCGGCGCTGCCACTGCGTTCGTAGATCGTCTTGAACAACC

ATCTGGCTTCTGCCTTGCCTGCGGCGCGGCGTGCCAGGCGGTAGAGAAAACGGCCGATGCCGGGATCGATCAAAAAG

TAATCGGGGTGAACCGTCAGCACGTCCGGGTTCTTGCCTTCTGTGATCTCGCGGTACATCCAATCAGCTAGCTCGAT

CTCGATGTACTCCGGCCGCCCGGTTTCGCTCTTTACGATCTTGTAGCGGCTAATCAAGGCTTCACCCTCGGATACCG

TCACCAGGCGGCCGTTCTTGGCCTTCTTCGTACGCTGCATGGCAACGTGCGTGGTGTTTAACCGAATGCAGGTTTCT

ACCAGGTCGTCTTTCTGCTTTCCGCCATCGGCTCGCCGGCAGAACTTGAGTACGTCCGCAACGTGTGGACGGAACAC

GCGGCCGGGCTTGTCTCCCTTCCCTTCCCGGTATCGGTTCATGGATTCGGTTAGATGGGAAACCGCCATCAGTACCA

GGTCGTAATCCCACACACTGGCCATGCCGGCCGGCCCTGCGGAAACCTCTACGTGCCCGTCTGGAAGCTCGTAGCGG

ATCACCTCGCCAGCTCGTCGGTCACGCTTCGACAGACGGAAAACGGCCACGTCCATGATGCTGCGACTATCGCGGGT

GCCCACGTCATAGAGCATCGGAACGAAAAAATCTGGTTGCTCGTCGCCCTTGGGCGGCTTCCTAATCGACGGCGCAC

CGGCTGCCGGCGGTTGCCGGGATTCTTTGCGGATTCGATCAGCGGCCGCTTGCCACGATTCACCGGGGCGTGCTTCT

GCCTCGATGCGTTGCCGCTGGGCGGCCTGCGCGGCCTTCAACTTCTCCACCAGGTCATCACCCAGCGCCGCGCCGAT

TTGTACCGGGCCGGATGGTTTGCGACCGCTCACGCCGATTCCTCGGGCTTGGGGGTTCCAGTGCCATTGCAGGGCCG

GCAGGCAACCCAGCCGCTTACGCCTGGCCAACCGCCCGTTCCTCCACACATGGGGCATTCCACGGCGTCGGTGCCTG

GTTGTTCTTGATTTTCCATGCCGCCTCCTTTAGCCGCTAAAATTCATCTACTCATTTATTCATTTGCTCATTTACTC

TGGTAGCTGCGCGATGTATTCAGATAGCAGCTCGGTAATGGTCTTGCCTTGGCGTACCGCGTACATCTTCAGCTTGG

TGTGATCCTCCGCCGGCAACTGAAAGTTGACCCGCTTCATGGCTGGCGTGTCTGCCAGGCTGGCCAACGTTGCAGCC

TTGCTGCTGCGTGCGCTCGGACGGCCGGCACTTAGCGTGTTTGTGCTTTTGCTCATTTTCTCTTTACCTCATTAACT

CAAATGAGTTTTGATTTAATTTCAGCGGCCAGCGCCTGGACCTCGCGGGCAGCGTCGCCCTCGGGTTCTGATTCAAG

AACGGTTGTGCCGGCGGCGGCAGTGCCTGGGTAGCTCACGCGCTGCGTGATACGGGACTCAAGAATGGGCAGCTCGT

ACCCGGCCAGCGCCTCGGCAACCTCACCGCCGATGCGCGTGCCTTTGATCGCCCGCGACACGACAAAGGCCGCTTGT

AGCCTTCCATCCGTGACCTCAATGCGCTGCTTAACCAGCTCCACCAGGTCGGCGGTGGCCCATATGTCGTAAGGGCT

TGGCTGCACCGGAATCAGCACGAAGTCGGCTGCCTTGATCGCGGACACAGCCAAGTCCGCCGCCTGGGGCGCTCCGT

CGATCACTACGAAGTCGCGCCGGCCGATGGCCTTCACGTCGCGGTCAATCGTCGGGCGGTCGATGCCGACAACGGTT

AGCGGTTGATCTTCCCGCACGGCCGCCCAATCGCGGGCACTGCCCTGGGGATCGGAATCGACTAACAGAACATCGGC

CCCGGCGAGTTGCAGGGCGCGGGCTAGATGGGTTGCGATGGTCGTCTTGCCTGACCCGCCTTTCTGGTTAAGTACAG

CGATAACCTTCATGCGTTCCCCTTGCGTATTTGTTTATTTACTCATCGCATCATATACGCAGCGACCGCATGACGCA

AGCTGTTTTACTCAAATACACATCACCTTTTTAGACGGCGGCGCTCGGTTTCTTCAGCGGCCAAGCTGGCCGGCCAG

GCCGCCAGCTTGGCATCAGACAAACCGGCCAGGATTTCATGCAGCCGCACGGTTGAGACGTGCGCGGGCGGCTCGAA

CACGTACCCGGCCGCGATCATCTCCGCCTCGATCTCTTCGGTAATGAAAAACGGTTCGTCCTGGCCGTCCTGGTGCG

GTTTCATGCTTGTTCCTCTTGGCGTTCATTCTCGGCGGCCGCCAGGGCGTCGGCCTCGGTCAATGCGTCCTCACGGA

AGGCACCGCGCCGCCTGGCCTCGGTGGGCGTCACTTCCTCGCTGCGCTCAAGTGCGCGGTACAGGGTCGAGCGATGC

ACGCCAAGCAGTGCAGCCGCCTCTTTCACGGTGCGGCCTTCCTGGTCGATCAGCTCGCGGGCGTGCGCGATCTGTGC
```

-continued

```
CGGGGTGAGGGTAGGGCGGGGGCCAAACTTCACGCCTCGGGCCTTGGCGGCCTCGCGCCCGCTCCGGGTGCGGTCGA

TGATTAGGGAACGCTCGAACTCGGCAATGCCGGCGAACACGGTCAACACCATGCGGCCGGCCGGCGTGGTGGTGTCG

GCCCACGGCTCTGCCAGGCTACGCAGGCCCGCGCCGGCCTCCTGGATGCGCTCGGCAATGTCCAGTAGGTCGCGGGT

GCTGCGGGCCAGGCGGTCTAGCCTGGTCACTGTCACAACGTCGCCAGGGCGTAGGTGGTCAAGCATCCTGGCCAGCT

CCGGGCGGTCGCGCCTGGTGCCGGTGATCTTCTCGGAAAACAGCTTGGTGCAGCCGGCCGCGTGCAGTTCGGCCCGT

TGGTTGGTCAAGTCCTGGTCGTCGGTGCTGACGCGGGCATAGCCCAGCAGGCCAGCGGCGGCGCTCTTGTTCATGGC

GTAATGTCTCCGGTTCTAGTCGCAAGTATTCTACTTTATGCGACTAAAACACGCGACAAGAAAACGCCAGGAAAGG

GCAGGGCGGCAGCCTGTCGCGTAACTTAGGACTTGTGCGACATGTCGTTTTCAGAAGACGGCTGCACTGAACGTCAG

AAGCCGACTGCACTATAGCAGCGGAGGGGTTGGATCAAAGTACTTTGATCCCGAGGGGAACCCTGTGGTTGGCATGC

ACATACAAATGGACGAACGGATAAACCTTTTCACGCCCTTTTAAATATCCGATTATTCTAATAAACGCTCTTTTCTC

TTAGGTTTACCCGCCAATATATCCTGTCAAACACTGATAGTTTAAAAGCTTTCCCGATCTAGTAACATAGATGACAC

CGCGCGCGATAATTTATCCTAGTTTGCGCGCTATATTTTGTTTTCTATCGCGTATTAAATGTATAATTGCGGGACTC

TAATCATAAAAACCCATCTCATAAATAACGTCATGCATTACATGTTAATTATTACATGCTTAACGTAATTCAACAGA

AATTATATGATAATCATCGCAAGACCGGCAACAGGATTCAATCTTAAGAAACTTTATTGCCAAATGTTTGAACGATC

GGGGAAATTCGAGCTACCACTTTGTACAAGAAAGCTGGGTTTAAGCCTTCTTGATAGCAGCAGCGAGTTCATCGTAA

GCAACTTCCCAAGCCCTAGACAATTCATCTGACCATTTATCACCAACAGCAGCTTTAATAGTTTTAAGCAAAGCTTC

TTTCACAACAACGAACTGAGGATCTGTAACAGCCTTTTGAGCATGAACTGAACCCAAAGCAGCATCAGCAACAACTG

TCCCAGAAGCTTTAAGCTGACCAGCTGAATCTCTCACCAGAGCAAAAAGCTTTTCTGCATGTCCAGTCAACTTAGGA

TTTGTTGGATCAACACCGTTAGCCAAAAATGAAAACAAATCCTTAGCAGCAGGAGCTTTTTCCAAAATTGATGTGTA

GAAAACCACAGAATATTGTGGAATATTTGCCTTGAAAGCTTCAAATGATGATGAAACAAGAGCATCTTGCTTTTCAG

TAAAAGCAACCATGGTGGCAGCCTGCTTTTTTGTACAAACTTGTCAGCGTGTCCTCTCCAAATGAAATGAACTTCCT

TATATAGAGGAAGGGTCTTGCGAAGGATAGTGGGATTGTGCGTCATCCCTTACGTCAGTGGAGATATCACATCAATC

CACTTGCTTTGAAGACGTGGTTGGAACGTCTTCTTTTTCCACGATGCTCCTCGTGGGTGGGGGTCCATCTTTGGGAC

CACTGTCGGCAGAGGCATCTTGAACGATAGCCTTTCCTTTATCGCAATGATGGCATTTGTAGGTGCCCACCTTCCTTT

TCTACTGTCCTTTTGATGAAGTGACAGATAGCTGGGCAATGGAATCCGAGGAGGTTTCCCGATATTACCCTTTGTTG

AAAAGTCTCAATAGCCCTTTGGTCTTCTGAGACTGTATCTTTGATATTCTTGGAGTAGACGAGAGTGTCGTGCTCCA

CCATGTTCACATCAATCCACTTGCTTTGAAGACGTGGTTGGAACGTCTTCTTTTTCCACGATGCTCCTCGTGGGTGG

GGGTCCATCTTTGGGACCACTGTCGGCAGAGGCATCTTGAACGATAGCCTTTCCTTTATCGCAATGATGGCATTTGT

AGGTGCCACCTTCCTTTTCTACTGTCCTTTTGATGAAGTGACAGATAGCTGGGCAATGGAATCCGAGGAGGTTTCCC

GATATTACCCTTTGTTGAAAAGTCTCAATAGCCCTTTGGTCTTCTGAGACTGTATCTTTGATATTCTTGGAGTAGAC

GAGAGTGTCGTGCTCCACCATGTTGGCCAACTTTTCTATACAAAGTTG
```

Genes

Aspects of the present disclosure relate to the expression of one or more genes (coding sequences) into a plant cell (e.g., a tomato plant cell or an eggplant plant cell).

In some embodiments, a gene of the present disclosure is a heme-producing gene. In some embodiments, a heme-producing gene is derived from *Glycine max* (soybean). In some embodiments, a heme-producing gene derived from *Glycine max* is a leghemoglobin gene. Leghemoglobin (also known as leghaemoglobin or legoglobin) is an oxygen-carrying phytoglobin found in the nitrogen-fixing root nodules of leguminous plants. It is produced by these plants in response to the roots being colonized by nitrogen-fixing bacteria, termed *rhizobia*, as part of the symbiotic interaction between plant and bacterium. Leghemoglobin has close chemical and structural similarities to hemoglobin, and, like hemoglobin, is red in color. Leghemoglobins are monomeric proteins with a mass of around 16 kDa, and are structurally similar to myoglobin. In some embodiments, leghemoglobin is expressed in a plant (e.g., tomato plant or eggplant plant) to mimic the color, taste, and/or texture of meat.

In some embodiments, a heme-producing gene is a functional homolog of leghemoglobin. The term "functional homolog," as used herein, includes genes or proteins that share a common ancestor and perform the same or similar functions, even if they have different underlying structures. Non-limiting examples of functional homologs of leghemoglobin include myoglobin and hemoglobin.

In some embodiments, a gene of the present disclosure is codon-optimized. In some embodiments, a gene of the present disclosure is codon-optimized for expression in a tomato or eggplant. The term "codon-optimized," as used herein, includes altering the DNA sequence of a gene without changing the amino acid sequence of the protein encoded by the gene. This is done to improve the efficiency of translation and improve protein yield in a specific host organism (e.g., a tomato plant or eggplant plant).

A non-limiting example of a codon-optimized leghemo-globin gene derived from *Glycine max* is provided as SEQ ID NO: 5:

```
(SEQ ID NO: 5)
ATGGTTGCTTTTACTGAAAAGCAAGATGCTCTTGTTTCATCATCATTTGAAGCTTTCAAGGCAAATATTCCACAATA

TTCTGTGGTTTTCTACACATCAATTTTGGAAAAAGCTCCTGCTGCTAAGGATTTGTTTTCATTTTTGGCTAACGGTG

TTGATCCAACAAATCCTAAGTTGACTGGACATGCAGAAAAGCTTTTTGCTCTGGTGAGAGATTCAGCTGGTCAGCTT

AAAGCTTCTGGGACAGTTGTTGCTGATGCTGCTTTGGGTTCAGTTCATGCTCAAAAGGCTGTTACAGATCCTCAGTT

CGTTGTTGTGAAAGAAGCTTTGCTTAAAACTATTAAAGCTGCTGTTGGTGATAAATGGTCAGATGAATTGTCTAGGG

CTTGGGAAGTTGCTTACGATGAACTCGCTGCTGCTATCAAGAAGGCTTAA
```

In some embodiments, a gene of the present disclosure is a male-sterility gene. The term "male-sterility gene," as used herein, includes a gene that improves seed purity. In some embodiments, a male-sterility gene is derived from *Bacillus amyloliquefaciens*. In some embodiments, a male-sterility gene derived from *Bacillus amyloliquefaciens* is a barnase gene. A barnase gene (a portmanteau of "BActerial" "Ribo-NucleASE") is a bacterial protein that consists of about 110 amino acids and has ribonuclease activity. In some embodiments, a barnase gene is codon-optimized.

A non-limiting example of a barnase gene derived from *Bacillus amyloliquefaciens* is provided as SEQ ID NO: 6:

```
(SEQ ID NO: 6)
GCACAGGTTATCAACACGTTTGACGGGGTTGCGGATTATCTTCAGACATATCATAAGCTACCTGATAATTACATTAC

AAAATCAGAAGCACAAGCCCTCGGCTGGGTGGCATCAAAAGGGAACCTTGCAGACGTCGCTCCGGGGAAAAGCATCG

GCGGAGACATCTTCTCAAACAGGGAAGGCAAACTCCCGGGCAAAGCGGACGAACATGGCGTGAAGCGGATATTAAC

TATACATCAGGCTTCAGAAATTCAGACCGGATTCTTTACTCAAGCGACTGGCTGATTTACAAAACAACGGACCATTA

TCAGACCTTTACAAAAATCAGATAA
```

In some embodiments, a gene of the present disclosure is a selectable marker. The term "selectable marker," as used herein, includes a gene that is introduced into a cell or organism to identify which cells or organisms have been genetically transformed or transfected (i.e., with a genetic construct or set of genetic constructs). In some embodiments, a selectable marker is a positive selectable marker that confers selective advantage to the cell or organism. In some embodiments, a positive selectable marker is an antibiotic resistance gene. Non-limiting examples of positive selectable markers include a hygromycin resistance gene, an nptII gene, a kanamycin resistance gene, a chloramphenicol resistance gene, and an ampicillin resistance gene. In some embodiments, a selectable marker is a negative selectable marker that eliminates or inhibits growth of the cell or organism upon selection. A non-limiting example of a nega-tive selective marker includes the thymidine kinase gene. In some embodiments, a selectable marker of the present disclosure is an antibiotic resistance gene. In some embodi-ments, a gene of the present disclosure is an antibiotic resistance gene. The term "antibiotic resistance gene," as used herein, includes genes that confer resistance to an antibiotic, often enabling the cell expressing the gene to modify the antibiotic, alter its target, or pump it out of the cell. Antibiotic resistance genes are often used in research to select for cells that express a genetic construct containing the antibiotic resistance gene. In some embodiments, a selectable marker of the present disclosure is a hygromycin resistance gene. In some embodiments, an antibiotic resis-tance gene is a hygromycin resistance gene. The term "hygromycin resistance gene," also known as the "hph gene," as used herein, includes a DNA sequence that encodes an enzyme called hygromycin phosphotransferase (HPT). HPT modifies the antibiotic hygromycin B, render-ing it inactive and thus conferring resistance to the organism (e.g. plant) carrying the gene.

A non-limiting example of a hygromycin resistance gene is provided as SEQ ID NO: 7:

(SEQ ID NO: 7)
```
ATGAAAAAGCCTGAACTCACCGCGACGTCTGTCGAGAAGTTTCTGATCGAAAAGTTCGACAGCGTCTCCGACCTGAT

GCAGCTCTCGGAGGGCGAAGAATCTCGTGCTTTCAGCTTCGATGTAGGAGGGCGTGGATATGTCCTGCGGGTAAATA

GCTGCGCCGATGGTTTCTACAAAGATCGTTATGTTTATCGGCACTTTGCATCGGCCGCGCTCCCGATTCCGGAAGTG

CTTGACATTGGGGAGTTTAGCGAGAGCCTGACCTATTGCATCTCCCGCCGTTCACAGGGTGTCACGTTGCAAGACCT

GCCTGAAACCGAACTGCCCGCTGTTCTACAACCGGTCGCGGAGGCTATGGATGCGATCGCTGCGGCCGATCTTAGCC

AGACGAGCGGGTTCGGCCCATTCGGACCGCAAGGAATCGGTCAATACACTACATGGCGTGATTTCATATGCGCGATT

GCTGATCCCCATGTGTATCACTGGCAAACTGTGATGGACGACACCGTCAGTGCGTCCGTCGCGCAGGCTCTCGATGA

GCTGATGCTTTGGGCCGAGGACTGCCCCGAAGTCCGGCACCTCGTGCACGCGGATTTCGGCTCCAACAATGTCCTGA

CGGACAATGGCCGCATAACAGCGGTCATTGACTGGAGCGAGGCGATGTTCGGGGATTCCCAATACGAGGTCGCCAAC

ATCTTCTTCTGGAGGCCGTGGTTGGCTTGTATGGAGCAGCAGACGCGCTACTTCGAGCGGAGGCATCCGGAGCTTGC

AGGATCGCCACGACTCCGGGCGTATATGCTCCGCATTGGTCTTGACCAACTCTATCAGAGCTTGGTTGACGGCAATT

TCGATGATGCAGCTTGGGCGCAGGGTCGATGCGACGCAATCGTCCGATCCGGAGCCGGGACTGTCGGGCGTACACAA

ATCGCCCGCAGAAGCGCGGCCGTCTGGACCGATGGCTGTGTAGAAGTACTCGCCGATAGTGGAAACCGACGCCCCAG

CACTCGTCCGAGGGCAAAGAAATAG
```

In some embodiments, a gene of the present disclosure is a reporter gene such as β-glucuronidase (GUS) reporter gene. The term "reporter gene," as used herein, includes a gene whose expression can be measured and is used to study other genes, understand gene regulation, or screen for successful transformations.

A non-limiting example of a GUS reporter gene is provided as SEQ ID NO: 8:

(SEQ ID NO: 8)
```
ATGGTAGATCTGAGGGTAAATTTCTAGTTTTTCTCCTTCATTTTCTTGGTTAGGACCCTTTTCTCTTTTTATTTTTT

TGAGCTTTGATCTTTCTTTAAACTGATCTATTTTTTAATTGATTGGTTATGGTGTAAATATTACATAGCTTTAACTG

ATAATCTGATTACTTTATTTCGTGTGTCTATGATGATGATGATAGTTACAGAACCGACGACTCGTCCGTCCTGTAGA

AACCCCAACCCGTGAAATCAAAAAACTCGACGGCCTGTGGGCATTCAGTCTGGATCGCGAAAACTGTGGAATTGATC

AGCGTTGGTGGGAAAGCGCGTTACAAGAAAGCCGGGCAATTGCTGTGCCAGGCAGTTTTAACGATCAGTTCGCCGAT

GCAGATATTCGTAATTATGCGGGCAACGTCTGGTATCAGCGCGAAGTCTTTATACCGAAAGGTTGGGCAGGCCAGCG

TATCGTGCTGCGTTTCGATGCGGTCACTCATTACGGCAAAGTGTGGGTCAATAATCAGGAAGTGATGGAGCATCAGG

GCGGCTATACGCCATTTGAAGCCGATGTCACGCCGTATGTTATTGCCGGGAAAAGTGTACGTATCACCGTTTGTGTG

AACAACGAACTGAACTGGCAGACTATCCCGCCGGGAATGGTGATTACCGACGAAAACGGCAAGAAAAAGCAGTCTTA

CTTCCATGATTTCTTTAACTATGCCGGAATCCATCGCAGCGTAATGCTCTACACCACGCCGAACACCTGGGTGGACG

ATATCACCGTGGTGACGCATGTCGCGCAAGACTGTAACCACGCGTCTGTTGACTGGCAGGTGGTGGCCAATGGTGAT

GTCAGCGTTGAACTGCGTGATGCGGATCAACAGGTGGTTGCAACTGGACAAGGCACTAGCGGGACTTTGCAAGTGGT

GAATCCGCACCTCTGGCAACCGGGTGAAGGTTATCTCTATGAACTCGAAGTCACAGCCAAAAGCCAGACAGAGTCTG

ATATCTACCCGCTTCGCGTCGGCATCCGGTCAGTGGCAGTGAAGGGCCAACAGTTCCTGATTAACCACAAACCGTTC

TACTTTACTGGCTTTGGTCGTCATGAAGATGCGGACTTACGTGGCAAAGGATTCGATAACGTGCTGATGGTGCACGA

CCACGCATTAATGGACTGGATTGGGGCCAACTCCTACCGTACCTCGCATTACCCTTACGCTGAAGAGATGCTCGACT

GGGCAGATGAACATGGCATCGTGGTGATTGATGAAACTGCTGCTGTCGGCTTTCAGCTGTCTTTAGGCATTGGTTTC

GAAGCGGGCAACAAGCCGAAAGAACTGTACAGCGAAGAGGCAGTCAACGGGGAAACTCAGCAAGCGCACTTACAGGC
```

-continued

```
GATTAAAGAGCTGATAGCGCGTGACAAAAACCACCCAAGCGTGGTGATGTGGAGTATTGCCAACGAACCGGATACCC

GTCCGCAAGGTGCACGGGAATATTTCGCGCCACTGGCGGAAGCAACGCGTAAACTCGACCCGACGCGTCCGATCACC

TGCGTCAATGTAATGTTCTGCGACGCTCACACCGATACCATCAGCGATCTCTTTGATGTGCTGTGCCTGAACCGTTA

TTACGGATGGTATGTCCAAAGCGGCGATTTGGAAACGGCAGAGAAGGTACTGGAAAAAGAACTTCTGGCCTGGCAGG

AGAAACTGCATCAGCCGATTATCATCACCGAATACGGCGTGGATACGTTAGCCGGGCTGCACTCAATGTACACCGAC

ATGTGGAGTGAAGAGTATCAGTGTGCATGGCTGGATATGTATCACCGCGTCTTTGATCGCGTCAGCGCCGTCGTCGG

TGAACAGGTATGGAATTTCGCCGATTTTGCGACCTCGCAAGGCATATTGCGCGTTGGCGGTAACAAGAAAGGGATCT

TCACTCGCGACCGCAAACCGAAGTCGGCGGCTTTTCTGCTGCAAAAACGCTGGACTGGCATGAACTTCGGTGAAAAA

CCGCAGCAGGGAGGCAAACAA
```

Promoters

Aspects of the present disclosure relate to the use of a promoter to drive expression of a gene described elsewhere herein. The term "promoter," as used herein includes a region of DNA located upstream of a gene where proteins, such as ribonucleic acid (RNA) polymerase and transcription factors, bind to initiate transcription of the gene. This process results in the production of RNA molecules, such as messenger RNA (mRNA), which are essential for gene expression. Promoters are specific sequences that serve as landing pads for the transcription machinery, playing an important role in regulating gene activity. In some embodiments, a promoter (e.g., a first promoter and/or a second promoter) is a eukaryotic promoter. Non-limiting examples of eukaryotic promoters include E8, E8S, PSEND1, TDH3, PGK1, PKC1, PDC1, TEF1, TEF2, RPL18B. SSA1, TDH2, PYK1, TPI1 GAL1, GAL10, GAL7, GAL3, GAL2, MET3, MET25, HXT3, HXT7, ACT1, ADH1, ADH2, CUP1-1, ENO2, and SOD1, as would be known to one of ordinary skill in the art (see, e.g., Addgene website: blog.addgene-.org/plasmids-101-the-promoter-region). In some embodiments, a promoter (e.g., a first promoter and/or a second promoter) is a prokaryotic promoter (e.g., bacteriophage or bacterial promoter). Non-limiting examples of bacterio- phage promoters include Pls1con, T3, T7, SP6, and PL. Non-limiting examples of bacterial promoters include PmgrB, Ptrc2, PCI857, Pbad, Plac/ara, Plac/fnr, Ptac, Ptet, Pcmt, and Pm. In some embodiments, any promoter known in the art and suitable for a selected host cell (e.g., tomato plant cell or eggplant plant cell) can be used.

In some embodiments, a promoter is operably linked to a gene. The term "operably linked." as used herein, includes a functional relationship between nucleic acids, indicating that they are placed in a way that allows one nucleic acid sequence to control the expression of another.

In some embodiments, a genetic construct or set of genetic constructs of the present disclosure comprises one or more promoters. In some embodiments, a genetic construct or set of genetic constructs of the present disclosure com- prises a first promoter and a second promoter. In some embodiments, the first promoter and the second promoter are different. In some embodiments, the first promoter and the second promoter are the same. In some embodiments, one promoter drives the expression of one or more genes. The first and second promoter may be the same type of promoter or may be the same, single promoter that effects the expression of both coding sequences, in an embodiment of any one of the compositions or methods provided herein.

In some embodiments, a promoter (e.g., a first promoter and/or a second promoter) is a constitutive promoter. The term "constitutive promoter," includes an unregulated pro- moter that allows continuous transcription of a gene. Non- limiting examples of a constitutive promoter include CaMV 35S, TDH3, PGK1, PKC1, PDC1, TEF1, TEF2, RPL18B, SSA1, TDH2, PYK1, TPI1, HXT3, HXT7, ACT1, ADH1, ADH2, ENO2, CMV, and SOD1. In some embodiments, a constitutive promoter is a Cauliflower Mosaic Virus (CaMV 35S). Other constitutive promoters known to one of ordinary skill in the art are also contemplated in this application.

A non-limiting examples of a Cauliflower Mosaic Virus (CaMV 35S) promoter is provided as SEQ ID NO: 9:

(SEQ ID NO: 9)
```
TGAGACTTTTCAACAAAGGGTAATATCGGGAAACCTCCTCGGATTCCATTGCCCAGCTATCTGTCACTTCATCAAAA

GGACAGTAGAAAAGGAAGGTGGCACCTACAAATGCCATCATTGCGATAAAGGAAAGGCTATCGTTCAAGATGCCTCT

GCCGACAGTGGTCCCAAAGATGGACCCCCACCCACGAGGAGCATCGTGGAAAAAGAAGACGTTCCAACCACGTCTTC

AAAGCAAGTGGATTGATGTGAACATGGTGGAGCACGACACTCTCGTCTACTCCAAGAATATCAAAGATACAGTCTCA

GAAGACCAAAGGGCTATTGAGACTTTTCAACAAAGGGTAATATCGGGAAACCTCCTCGGATTCCATTGCCCAGCTAT

CTGTCACTTCATCAAAAGGACAGTAGAAAAGGAAGGTGGCACCTACAAATGCCATCATTGCGATAAAGGAAAGGCTA

TCGTTCAAGATGCCTCTGCCGACAGTGGTCCCAAAGATGGACCCCCACCCACGAGGAGCATCGTGGAAAAAGAAGAC

GTTCCAACCACGTCTTCAAAGCAAGTGGATTGATGTGATATCTCCACTGACGTAAGGGATGACGCACAATCCCACTA

TCCTTCGCAAGACCCTTCCTCTATATAAGGAAGTTCATTTCATTTGGAGAGGACACGCTGA
```

In some embodiments, a promoter is a tissue-specific promoter. The term "tissue-specific promoter," as used herein, includes a DNA sequence that regulates gene expression in a particular tissue or cell type, ensuring that genes are activated only in the appropriate locations within an organism. In some embodiments, a tissue-specific promoter is a plant-specific promoter, a plant promoter, or a fruit-specific promoter. In some embodiments, a plant promoter is an anther-specific promoter. The term "anther-specific," as used herein, includes a regulatory element used in plant genetic engineering to control gene expression specifically in the anthers. Non-limiting examples of plant promoters include an E8 promoter, *Pisum sativum* Endothecium 1 (PSEND1) promoter, and a TA29 promoter.

A non-limiting examples of an E8 promoter is provided as SEQ ID NO: 10:

```
                                                          (SEQ ID NO: 10)
AAGCTTTCCCTAATGATATTGTTCATGTAATTAAGTTTTGTGGAAGTGAGAGAGTCCAATTTTGATAAGAAAAGAGT

CAGAAAACGTAATATTTTAAAAGTCTAAATCTTTCTACAAATAAGAGCAAATTTATTTATTTTTAATCCAATAAAT

ATTAATGGAGGACAAATTCAATTCACTTGGTTGTAAAATAAACTTAAACCAATAACCAAAGAACTAATAAATCCTGA

AGTGGAATTATTAAGGATAAATGTACATAGACAATGAAGAAATAATAGGTTCGATGAATTAATAATAATTAAGGATG

TTACAATCATCATGTGCCAAGTATATACACAATATTCTATGGGATTTATAATTTCGTTACTTCACTTAACTTTTGCG

TAAATAAAACGAATTATCTGATATTTTATAATAAAACAGTTAATTAAGAACCATCATTTTTAACAACATAGATATAT

TATTTCTAATAGTTTAATGATACTTTTAAATCTTTTAAATTTTATGTTTCTTTTAGAAAATAAAAATTCAAAAAATT

AAATATATTTACAAAAACTACAATCAAACACAACTTCATATATTAAAAGCAAAATATATTTTGAAAATTTCAAGTGT

CCTAACAAATAAGACAAGAGGAAAATGTACGATGAGAGACATAAAGAGAACTAATAATTGAGGAGTCCTATAATATA

TAATAAAGTTTATTAGTAAACTTAATTATTAAGGACTCCTAAAATATATGATAGGAGAAAATGAATGGTGAGAGATA

TTGGAAAACTTAATAATTAAGGATTTTAAAATATATGGTAAAAGATAGGCAAAGTATCCATTATCCCCTTTTAACTT

GAAGTCTACTAGGCGCATGTGAAAGTTGATTTTTTGTCACGTCATATAGCTATAACGTAAAAAAAGAAAGTAAAATT

TTTAATTTTTTTTAATATATGACATATTTTAAACGAAATATAGGACAAAATGTAAATGAATAGTAAAGGAAACAAAG

ATTAATACTTACTTTGTAAGAATTTAAGATAAATTTAAAATTTAATAGATCAACTTTACGTCTAGAAAGACCCTATC

TTAGAAGGAATTTCAGAAATCGGCCCTTTTTCAAAAATAACTTTTAAATAATGAATTTTAAATTTTAAGAAATAATT

TCCAATGAATAAATGACATGTAGCATTTTACCTAAATATTTCAACTATTTTAATCCAATATTAATTTGTTTATTCCC

AACAATAGAAAGTCTTGTGCAGACATTTAATCTGACTTTTCCAGTACTAAATATTAATTTTCTGAAGATTTTCGGGT

TTAGTCCACAAGTTTTAGTGAGAAGTTTTGCTCAAAATTTTAGGTGAGAAGGTTTGATATTTATCTTTTGTTAAATT

AATTTATCTAGGTGACTATTATTTATTTAAGTAGAAATTCATATCATTACTTTTGCCAACTTGTAGTCATAATAGGA

GTAGGTGTATATGATGAAGGAATAAACAAGTTCAGTGAAGTGATTAAAATAAAATATAATTTAGGTGTACATCAAAT

AAAAACCTTAAAGTTTAGAAAGGCACCGAATAATTTTGCATAGAAGATATTAGTAAATTTATAAAAATAAAAGAAAT

GTAGTTGTCAAGTTGTCTTCTTTTTTTTGGATAAAAATAGCAGTTGGCTTATGTCATTCTTTTACAACCTCCATGCC

ACTTGTCCAATTGTTGACACTTAACTAATTAGTTTGATTCATGTATGAATACTAAATAATTTTTTAGGACTGACTCA

AATATTTTTATATTATCATAGTAATATTTATCTAATTTTTAGGACCACTTATTACTAAATAATAAATTAACTACTAC

TATATTATTGTTGTGAAACAACAACGTTTTGGTTGTTATGATGAAACGTACACTATATCAGTATGAAAAATTCAAAA

CGATTAGTATAAATTATATTGAAAATTTGATATTTTTCTATTCTTAATCAGACGTATTGGGTTTCATATTTTAAAAA

GGGACTAAACTTAGAAGAGAAGTTTGTTTGAAACTACTTTTGTCTCTTTCTTGTTCCCATTTCTCTCTTAGATTTCA

AAAAGTGAACTACTTTATCTCTTTCTTTGTTCACATTTTATTTTATTCTATTATAAATATGGCATCCTCATATTGAG

ATTTTTAGAAATTATTCTAATCATTCACAGTGCAAAAGAAGGGATCC
```

A non-limiting examples of a PSEND1 promoter is provided as SEQ ID NO: 11:

```
                                                          (SEQ ID NO: 11)
GACTTCAACCTTATTAGTGAATGGACAATAAAGGTTATAAGCTCCTTTACTGTGAAAGCCCACCAGTAACATCACCT

TGCTTATATCATTCAGCTTCTTTCTAGTAACATTTGGAACGTGTTTATAACAGAAAAAAACCCAAAAACTCTGAAAA

GACTCACACTTTTCTTATCTCCAGTCCACCTCTCAAAAGGAACAATTTCCTTCAGCTTCTTGGTTGGACACCTGTTG
```

-continued

```
AGCACATATGCTGCAGTGGCAACAGTTTCTCCCCACAAAGTGTTAGGAAGCTTCTTCTCCTTCAGCATGTTCCTTGT

CATATCAAGCAAAGTTCGGTTTTCAACAAGACCATTATGTTGAGGAGTATATGGATCAGTCACTTCATGCTCAATTC

CATTCTCTTTACAGAACTTCTTGAACTCTGTAGAGTTATACTCACCTCCACCATCAGTTCTGAGAATCTTCAGAAGT

CTGACCACTTTATTTCTCAGCCTTGATTATGAATTTCTTAAATTCAGCAAACACCTCGTGTTTGAATTTTATAAGGG

ATACCCATGTCATCCTTGTGAACTCATCCATAAATGACATAAAGTATTATTCCCTCCTAGTGAAAGGTTTGTAATGG

GCCACACACATAAGAATGCACTACTCCTAAAGCATGTTTTGCTCTTTGAGCTACTTTTGATGAAAATGGCAGTCTTG

GTTGCTTCCCTTTCATGCACACATTACATGACTTTTTTGGTTTCTTAATTGTAGGAATTCCACGTACCAGTTTCTTT

GAATTCAAATTCCCTAAGCTCCTAAAGTTCAAATGACCAAATCTTTTGTTCCACAACTCACTTTCCTTCACAACACT

TGTTGCGCTAAGGCATTCAGAGTCTGCAGTTTTAACATTCGCCTTGAATGTTTTACTCCTTCCATGTTCTGACTCCA

TAATCAACTTCTGATAACAGTCATACAGCTTCAAAAGAATGTCATTCATGGTAACTGGAAATCCCTTTTCAATTAAT

TGACCTACACTCATCAGATTGCTCTTCATGCCAAGAACGTACCAAGACGTTCTGAATTAATGCAGATTTTCTATTAT

TCATAATCACTCTAACATTCCCCATTCCTTTAGCATTTAGTTACTTATCATCAGCACATCTAATCTTGGTTTTCTTC

CTAGAGTCAAAATCAACCAGCCATTTCTTATTTCCAGTATGATGGTTTGAACAACCAGTGTCCATATATCACCAGTC

TTCTATAGACGCACTATCATAACTAGAAGCCATTAATAGCACATGTTCATCATGGTGCTCAGATCCTTAGAATGTTC

AATTGCTACAACGATGTAATCAAACTGATGAGTAAGAGATCTAAGTACCTTCTCAATGATACTTTCCTCATAAAGAG

TTTCTCCATGCGACTTCATCTCATTTGTGATCAGAATCACTCTAGAGATGTAGTCAGATAACTTCTCATTGTTCTTC

ATGCTTAGATTCTCATACTGCTCACGTAGAGACTGAAGTTTCACCTTCTACACTGATGCATCACTATCGTAGCACCA

CACCAGTCTGTCTCACACAACCTTTTCCGTCATTGAATCAACGATTTTCTTAAACACGTTCACATCCACACACTGAT

GGATGTAGAACAACGCATTCTGATCCTTCTTCCTCATATCACACTGAGCATTTCTTTGCGCATCCGTTGCATTTTCT

AGAAGTGAAGCATAAACTTCGTTGATGAGATCAAGAACATCTTGAGCACCAAATAACACACACATCTGAATCATCCA

ACGATTCCAGTTGTTGTCGTCGAACAATGGNAGCNTGGTGCACAGATTCACAACGATATATTATAANTTTTGTTTTA

TGAAATTTAAGAACAAATTTCCATTATTCTTAAAATGTTTACACACTGATGTAGACTGCAAAAGGAATAAAGATACA

ATTTGTTCACACCACTCACTTGCGTAAATATAAGTGAGAGTTAATGAGAAATACTAAAATACCCTCTAAAATTATGA

ATTAATTCTAACAATCTCTAATGTTAGTATAATCCATTAAACACTTTGATGGCAGGTATAACAAGGGTGTAAGTTAG

TGTATACATATTAGGCTCTTATTATTTTTATATTATCTCTGCTTTTCTTCTTCATGTTCTCACTAATATGATATTAT

CTCCCTTCCCTAAATTATTTATATTTATTAGAAAAAGAGTTTCATTTTTTAAAAATATATTACCGTAATTTTTCAAA

AAATAAAATTTAAATATATTTTATAAAAAAATTATTTAATAATTTATTTACATTAATGCATAAATATAAATAAATAC

TGTCATTTAATATTTAACCTTTTTAACAATAAATTATATTTATTTAATTCAACTAATATAAGCTAAGTTATCTCATCC

AACCAATTAAAAAGATCATTTGAAAATACCTTTTTATTTAGTTTGTGGCGGTTTCAACTGTCAAAAAAAAGGAATTT

TTACGACGATATAAATTTAAACCAGCAAAAAATTGAAGCAGTTAAGCGAACCAACTCATGGTATGTGGATATATTTA

TCTTTGTCGTTTATATCGGATTCGAATCTCTATAATGATGAAAAATTAATATCAAACTTTAAATAAGAACGTCATTT

ATAGAGCCATTTTGGGAAACACATATTTCATGTACACGTGATTCGCAAATTTCCAATAACTCTATATATAGCCCTCC

TCAGTTTCATGCATTTGCTCACAACATAACCTTCCTTGAAT
```

55

A non-limiting examples of a TA29 promoter is provided as SEQ ID NO: 12:

(SEQ ID NO: 12)

```
CTTTTTGGTTAGCGAATGCAATTAATTTAGACATTGTGTTATGTTCCAGTTAACCGCTTCCCTGCACTTCTTTCAAT

CTATCTCTCGATAGAAAATTGTGATACTTTGCGACTTCTATCAGAGGACTTTTTGTTTTCCATGTAACAATCTGTCA

TTTTCGATGGGGAGATTTGCACAAATAGGCTATTTATGTGTCCCAATTTAAATTTTAACCCCATGTCGATCAGAACT

TAGCCACGAGCACCAGAAGTTTGATGGATATGTGACTTTGTCACTATCCGGTTTACTAATCAAGAGCTATTTTTATT
```

-continued

```
CAAAATTGGATATCTAGCTAAGTATAACTGGATAATTTGCATTAACAGATTGAATATAGTGCCAAACAAGAAGGGAC

AATTGACTTGTCACTTTATGAAAGATGATTCAAACATGATTTTTTATGTACTAATATATACATCCTACTCGAATTAA

AGCGACATAGGCTCGAAGTATGCACATTTAGCAATGTAAATTAAATCAGTTTTTGAATCAAGCTAAAAGCAGACTTG

CATAAGGTGGGTGGCTGGACTAGAATAAACATCTTCTCTAGCACAGCTTCATAATGTAATTTCCATAACTGAAATCA

GGGTGAGACAAAATTTTGGTACTTTTTCCTCACACTAAGTCCATGTTTGCAACAAATTAATACATGAAACCTTAATG

TTACCCTCAGATTAGCCTGCTACTCCCCATTTTCCTCGAAATGCTCCAACAAAAGTTAGTTTTGCAAGTTGTTGTGT

ATGTCTTGTGCTCTATATATGCCCTTGTGGTGCAAGTGTAACAGTACAACATCATCACTCAAATCAAAGTTTTTACT

TAAAGAAATTAGCTAAA
```

Terminators

Aspects of the present disclosure relate to the use of a terminator within genetic constructs to terminate gene expression. The term "terminator," as used herein, includes a section of nucleic acid sequence that marks the end of a gene or operon in DNA during transcription. A terminator sequence mediates transcriptional termination by providing signals in the newly synthesized transcript RNA that trigger processes which release the transcript RNA from the transcriptional complex. Non-limiting examples of terminators include a Noplaine Synthase (NOS) terminator and a Cauliflower Mosaic Virus (CaMV) polyadenylation (polyA) terminator.

A non-limiting example of a Noplaine Synthase (NOS) terminator is provided as SEQ ID NO: 13:

```
                                                          (SEQ ID NO: 13)
GATCGTTCAAACATTTGGCAATAAAGTTTCTTAAGATTGAATCCTGTTGCCGGTCTTGCGATGATTATCATATAATT

TCTGTTGAATTACGTTAAGCATGTAATAATTAACATGTAATGCATGACGTTATTTATGAGATGGGTTTTTATGATTA

GAGTCCCGCAATTATACATTTAATACGCGATAGAAAACAAAATATAGCGCGCAAACTAGGATAAATTATCGCGCGCG

GTGTCATCTATGTTACTAGATC
```

A non-limiting example of a CaMV PolyA terminator is provided as SEQ ID NO: 14:

```
                                                          (SEQ ID NO: 14)
TTTCTCCATAATAATGTGTGAGTAGTTCCCAGATAAGGGAATTAGGGTTCCTATAGGGTTTCGCTCATGTGTTGAGC

ATATAAGAAACCCTTAGTATGTATTTGTATTTGTAAAATACTTCTATCAATAAAATTTCTAATTCCTAAAACCAAAA

TCCAGTACTAAAATCCAGATC
```

Flanking Sequences

Aspects of the present disclosure relate to genetic constructs comprising a left and/or right flanking sequence. The left flanking sequence may be a left border (LB) T-DNA repeat flanking the genetic information in the genetic construct. A right flanking sequence may be a right border (RB) T-DNA repeat flanking the genetic information in the genetic constructs. LB and RB T-DNA repeats are short DNA sequences on a Ti plasmid in *Agrobacterium tumefaciens* that mark the beginning of the transferable DNA (T-DNA) region. LB and RB T-DNA repeats are used by the *Agrobacterium* to recognize the T-DNA for transfer into a plant cell.

A non-limiting example of a left border (LB) T-DNA repeat is provided as SEQ ID NO: 15:

```
                                          (SEQ ID NO: 15)
GTTTACACCACAATATATCCTGCCA
```

A non-limiting example of a right border (RB) T-DNA repeat is provided as SEQ ID NO:

```
                                          (SEQ ID NO: 16)
GTTTACCCGCCAATATATCCTGTCA
```

Sequence Identity

In some embodiments, a sequence of the present disclosure is a nucleotide sequence that is at least 70%, at least 75%, at least 80%, at least 85%, at least 90%, at least 95%, or at least 98% identical to any one of SEQ ID NOs: 1-16. In some embodiments, a sequence of the present disclosure is a nucleotide sequence that is 100% identical to any one of SEQ ID NOs: 1-16.

In some embodiments, a genetic construct of the present disclosure comprises a nucleotide sequence that is at least 70%, at least 75%, at least 80%, at least 85%, at least 90%, at least 95%, or at least 98% identical to any one of SEQ ID NOs: 1-4. In some embodiments, a genetic construct of the present disclosure comprises the nucleotide sequence of any one of SEQ ID NOs: 1-4.

In some embodiments, a gene of the present disclosure (e.g., heme-producing gene, barnase gene, antibiotic resistance gene, reporter gene) comprises a nucleotide sequence that is at least 70%, at least 75%, at least 80%, at least 85%, at least 90%, at least 95%, or at least 98% identical to any one of SEQ ID NOs: 5-8. In some embodiments, a gene of the present disclosure (e.g., heme-producing gene, barnase gene, antibiotic resistance gene, reporter gene) comprises the nucleotide sequence of any one of SEQ ID NOs: 5-8.

In some embodiments, a promoter of the present disclosure comprises a nucleotide sequence that is at least 70%, at least 75%, at least 80%, at least 85%, at least 90%, at least 95%, or at least 98% identical to any one of SEQ ID NOs: 9-12. In some embodiments, a promoter of the present disclosure comprises the nucleotide sequence of any one of SEQ ID NOs: 9-12.

In some embodiments, a terminator of the present disclosure comprises a nucleotide sequence that is at least 70%, at least 75%, at least 80%, at least 85%, at least 90%, at least 95%, or at least 98% identical to SEQ ID NO: 13 or SEQ ID NO: 14. In some embodiments, a terminator of the present disclosure comprises the nucleotide sequence of SEQ ID NO: 13 or SEQ ID NO: 14.

In some embodiments, a T-DNA repeat sequence of the present disclosure comprises a nucleotide sequence that is at least 70%, at least 75%, at least 80%, at least 85%, at least 90%, at least 95%, or at least 98% identical to SEQ ID NO: 15 or SEQ ID NO: 16. In some embodiments, a T-DNA repeat of the present disclosure comprises the nucleotide sequence of SEQ ID NO: 15 or SEQ ID NO: 16.

As a person having ordinary skill in the art will appreciate that any gene described herein encodes a corresponding mRNA, amino acid sequence, and polypeptide or protein.

The term "sequence identity," as used herein, includes the relatedness of the sequences of two nucleotides when the sequences are aligned, and the term "percent identity" refers to the percentage of residues (nucleotides) that are identical when two or more nucleotide sequences are aligned. In some embodiments, sequence identity and/or percent identity is determined across the entire length of a sequence. In some embodiments, sequence identity is determined over a region (e.g., a stretch of nucleotides).

Percent identity of nucleotide sequences can be calculated by any of the methods known to one of ordinary skill in the art. For example, percent identity can be determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST® and XBLAST® programs (version 2.0) of Altschul et al., *J. Mol. Biol.* 215:403-10, 1990. BLAST® protein searches can be performed, for example, with the XBLAST program, score=50, wordlength=3. Where gaps exist between two sequences, Gapped BLAST® can be utilized, for example, as described in Altschul et al., *Nucleic Acids Res.* 25 (17):

3389-3402, 1997. When utilizing BLAST® and Gapped BLAST® programs, the default parameters of the respective programs (e.g., XBLAST®) and NBLAST®) can be used, or the parameters can be adjusted appropriately as would be understood by one of ordinary skill in the art.

A second example of a local alignment technique is based on the Smith-Waterman algorithm (Smith, T. F. & Waterman, M. S. (1981) *J. Mol. Biol.* 147:195-197). An example of a global alignment technique is the Needleman-Wunsch algorithm (Needleman, S. B. & Wunsch, C. D. (1970) *J. Mol. Biol.* 48:443-453), which is based on dynamic programming. A further example of a global alignment technique is the Fast Optimal Global Sequence Alignment Algorithm (FOGSAA).

In some embodiments, the identity of two nucleotide sequences is determined by aligning the two nucleotide sequences of the polynucleotides, calculating the number of identical nucleotides and dividing by the length of one of the nucleotide sequences.

For multiple sequence alignments, computer programs including Clustal Omega (Sievers et al., *Mol Syst Biol.* 2011 Oct. 11:7:539) may be used.

In preferred embodiments, a sequence, including a nucleotide sequence, is found to have a specified percent identity to a reference sequence, such as a sequence disclosed in this application and/or recited in the claims when sequence identity is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993 (e.g., BLAST®), NBLAST®, XBLAST® or Gapped BLAST® programs, using default parameters of the respective programs).

In some embodiments, a sequence, including a nucleotide sequence, is found to have a specified percent identity to a reference sequence, such as a sequence disclosed in this application and/or recited in the claims when sequence identity is determined using the Smith-Waterman algorithm (Smith, T. F. & Waterman, M. S. (1981) *J. Mol. Biol.* 147:195-197) or the Needleman-Wunsch algorithm (Needleman, S. B. & Wunsch, C. D. (1970) *J. Mol. Biol.* 48:443-453) using default parameters.

In some embodiments, a sequence, including a nucleotide sequence, is found to have a specified percent identity to a reference sequence, such as a sequence disclosed in this application and/or recited in the claims when sequence identity is determined using a Fast Optimal Global Sequence Alignment Algorithm (FOGSAA) using default parameters.

In some embodiments, a sequence, including a nucleotide sequence, is found to have a specified percent identity to a reference sequence, such as a sequence disclosed in this application and/or recited in the claims when sequence identity is determined using Clustal Omega (Sievers et al., *Mol Syst Biol.* 2011 Oct. 11; 7:539) using default parameters.

In some embodiments, a nucleotide sequence of the present disclosure is a degenerate nucleotide sequence (e.g., a degenerate of any one of the nucleotide sequences provided herein such as degenerate of any one of SEQ ID NOs: 1-16). The term "degenerate nucleotide sequence," as used herein, includes nucleotide sequences in which one or more positions have multiple possible bases. In some embodiments, two degenerate nucleotide sequences that are at least about 90% identical to each other encode the same amino acid sequence. In some embodiments, two degenerate nucleotide sequences that are at least about 95% identical to each other encode the same amino acid sequence. In some embodiments, two degenerate nucleotide sequences that are at least about 98% identical to each other encode the same amino acid sequence. In some embodiments, a base within a degenerate nucleotide sequence is represented by an "N." In some embodiments, an "N" in a degenerate nucleotide sequence represents an adenine (A), a thymine (T), a guanine (G), or a cytosine (C). In some embodiments, a base within a degenerate nucleotide sequence is represented by an "R." In some embodiments, an "R" in a degenerate nucleotide sequence represents an adenine (A) or a guanine (G). In some embodiments, a base within a degenerate nucleotide sequence is represented by a "Y." In some embodiments, a "Y" in a degenerate nucleotide sequence represents a thymine (T) or a cytosine (C)

Genetically Engineered Plants and Plant Cells

Aspects of the present disclosure relate to genetically engineered plants and plant cells. The term "genetically engineered," as used herein, includes the modification of an organisms genetic makeup. Accordingly, a genetically engineered plant or plant cell is a plant or plant cell whose genetic makeup has been modified using techniques that allow for the direct transfer or removal of genes (e.g., transformation of any genetic construct(s) described herein into a plant or plant cell).

In some embodiments, a plant of the present disclosure is genetically engineered to express any genetic construct or set of genetic constructs described herein. In some embodiments, a plant is genetically engineered to express a vector comprising the nucleotide sequence of any one of SEQ ID NOs: 1-4. In some embodiments, a plant is genetically engineered to express a heme-producing gene comprising the nucleotide sequence of SEQ ID NO: 5. In some embodiments, a plant is genetically engineered to express a male-sterility gene comprising the nucleotide sequence of SEQ ID NO: 6. In some embodiments, a plant is genetically engineered to express an antibiotic resistance gene comprising the nucleotide sequence of SEQ ID NO: 5.

In some embodiments, a plant cell of the present disclosure is genetically engineered to express any genetic construct or set of genetic constructs described herein. In some embodiments, a plant cell is genetically engineered to express a vector comprising the nucleotide sequence of any one of SEQ ID NOs: 1-4. In some embodiments, a plant cell is genetically engineered to express a heme-producing gene comprising the nucleotide sequence of SEQ ID NO: 5. In some embodiments, a plant cell is genetically engineered to express a male-sterility gene comprising the nucleotide sequence of SEQ ID NO: 6. In some embodiments, a plant cell is genetically engineered to express an antibiotic resistance gene comprising the nucleotide sequence of SEQ ID NO: 5.

In some embodiments, a plant is a tomato plant. In some embodiments, a plant cell is a tomato plant cell. In some embodiments, a tomato of the present disclosure is of the genus *Solanum*. In some embodiments, a tomato of the present disclosure is *Solanum lycopersicum*. In some embodiments, a plant is an eggplant. In some embodiments, a plant cell is an eggplant cell. In some embodiments, an eggplant of the present disclosure is of the genus *Solanum*. In some embodiments, an eggplant of the present disclosure is *Solanum melongena*.

Methods of Expressing Heme in a Plant

Aspects of the present disclosure relate to a method of transforming a plant cell with any genetic construct (e.g., vector or plasmid) described herein. Aspects of the present disclosure also relate to a method of producing a genetically engineered plant comprising introducing into a plant any genetic construct (e.g., vector or plasmid) described herein.

In some embodiments, the method of transforming or introducing is accomplished via *Agrobacterium*-mediated transformation. The term "transformation," as used herein, includes the genetic alteration of a cell resulting from the direct uptake and incorporation of exogenous genetic material from its surroundings. The term "exogenous," as used herein, includes DNA sequences originating from outside an organism that are introduced into the organism to confer new traits.

*Agrobacterium*-mediated transformation (AMT) is a technique used in plant biotechnology to introduce foreign DNA into plant cells and generate genetically engineered plants. AMT utilizes the natural ability of the bacterium *Agrobacterium tumefaciens* to transfer transfer DNA (T-DNA) into plant cells. The process involves five steps: (i) preparation of *Agrobacterium*, (ii) infection of plant cells, (iii) T-DNA transfer, (iv) integration into plant genome, and (v) plant regeneration. During step (i), the bacterium is transformed with a genetic construct (e.g., SEQ ID NOs: 1-4) containing the desired gene (T-DNA) and a set of genes (vir genes) that encode the machinery for T-DNA transfer. During step (ii), the transformed *Agrobacterium* is incubated with plant cells (e.g., tomato or eggplant), typically from seedlings, leaves, or embryos (e.g., cotyledon). In some embodiments, the transformed *Agrobacterium* is incubated with a cotyledon. The term "cotyledon." as used herein, includes an embryonic leaf in seed-bearing plants, one or more of which are the first leaves to appear from a germinating seed. In some embodiments, a cotyledon is a tomato cotyledon. In some embodiments, a cotyledon is an eggplant cotyledon. In step (iii), the vir genes activate the transfer of the T-DNA from the bacterium into the plant cells. In step (iv), in some embodiments, the T-DNA integrates into the plant's genome, where it is expressed as a new gene. Finally, in step (v), the transformed plant cells are selected (e.g., using a selectable marker, e.g., a hygromycin resistance gene) and regenerated into whole plants carrying the introduced gene.

Accordingly, as described herein, aspects of the present disclosure relate to the use of *Agrobacterium*-mediated transformation to introduce a gene such as a heme-producing gene and/or a male-sterility gene into a plant (e.g., a tomato or eggplant).

Further aspects of the present disclosure relate to a method of producing an F1 hybrid plant (e.g., tomato or eggplant plant). The term "F1 hybrid," as used herein, includes a first generation of offspring from two different parent plants that have been intentionally cross-pollinated to create a new, uniform variety with improved traits. In some embodiments, the method of producing an F1 hybrid plant includes crossing a genetically engineered plant of the present disclosure (e.g., a tomato plant containing SEQ ID NO: 3 or SEQ ID NO: 4) with a male-fertile plant. The term "male-fertile plant." as used herein, includes a plant that is able to produce functional pollen and is therefore capable of self-pollination or fertilizing other plants. Unlike male-sterile plants, which are incapable of producing pollen, male-fertile plants have the necessary genes and mechanisms to complete the male reproductive process, such as the formation of functional anthers and pollen grains. In some embodiments, crossing a genetically engineered tomato plant of the present disclosure with a male-fertile plant produces a crossed plant. The term "crossed plant." as used herein, includes a hybrid plant created by cross-pollinating two different varieties or species. In some embodiments, the method further comprises growing the crossed plant. In some embodiments, the method further comprises harvesting seeds from the crossed plant. In some embodiments, the method further comprises growing an F1 hybrid plant from the seeds harvested from the crossed plant.

In some embodiments, an F1 hybrid tomato plant of the present disclosure exhibits heme production and male sterility. In some embodiments, the F1 hybrid tomato plant exhibits increased heme production relative to a tomato plant that is not genetically engineered. Other transformation techniques used in plant biotechnology to introduce foreign DNA into plant cells and generate genetically engineered plants are contemplated herein. Non-limiting examples of transformation techniques include biolistic transformation, microinjection, electroporation, and CRISPR/Cas technology (described elsewhere herein).

The term "biolistic transformation," as used herein, includes a method involving shooting microscopic gold or tungsten particles coated with DNA into plant cells using high-velocity gas. In some embodiments, biolistic transformation involves three steps: (i) preparation of microprojectiles, (ii) delivery mechanism, and (iii) integration of DNA. In step (i) particles, typically made of gold or tungsten, are coated with a DNA of interest. These particles serve as carriers for the genetic material. In step (ii), the coated microprojectiles are propelled into plant cells using a burst of gas, often helium. The high-velocity impact allows the particles to penetrate the rigid cell wall and membrane, delivering the DNA directly into the plant cytoplasm or nucleus. In step (iii), one inside the cell, the DNA can integrate into the plant cell genome, allowing for stable expression of the introduced genes. This integration can occur through various mechanisms, enabling the expression of new traits in the transformed plant cell.

The term "microinjection," as used herein, includes a technique in which DNA is directly injected into the plant cell nucleus using a fine needle. In some embodiments, microinjection transformation involves four steps: (i) preparation, (ii) micromanipulation, (iii) injection, and (iv) post-injection monitoring. In step (i), the genetic material (e.g., DNA) to be injected is prepared in a solution and loaded into a micropipette, which has a fine tip to minimize damage to the plant cell during insertion. In step (ii), the plant cells are positioned under a microscope using a micromanipulator, which allows for controlled movements of the micropipette. In step (iii), the micropipette penetrates the cell membrane, and the genetic material is delivered into the cell by applying hydrostatic pressure. In step (iv), after injection, the plant cells are monitored for recovery and expression of the introduced genetic material.

The term "electroporation," as used herein, include a method that uses an electric field to increase the permeability of a plant cell membrane, allowing DNA to enter the cell. When an electric field is applied to a plant cell, it induces temporary destabilization of the plant cell membrane, leading to the formation of hydrophilic channels or pores. The pores allow DNA to enter the cell. Once the electric field is removed, the membrane reseals, keeping the introduced DNA inside the plant cell. In some embodiments, electroporation transformation involves five steps: (i) cell preparation, (ii) DNA preparation, (iii) electroporation, (iv) recovery, and (v) culturing. In step (i), plant cells are cultured and harvested, then resuspended in an electroporation buffer to enhance conductivity and protect the cells. In step (ii), the DNA of interest is prepared in a suitable buffer. In step (iii), the plant cell-DNA mixture is placed in an electroporation cuvette, and an electric pulse is applied using an electroporator. In step (iv), after electroporation, plant cells are allowed to recover in a suitable growth medium, during which the cell membrane reseals. In step (v), the transformed plant cells are cultured to promote growth and expression of the introduced genetic material.

As a person having ordinary skill in the art will appreciate, any transformation method described herein or otherwise known in the art can be used to transform a genetic construct or set of genetic constructs described herein into a plant or plant cell (e.g., tomato plant or eggplant plant).

Methods of Overexpressing Lycopene in a Plant

Aspects of the present disclosure relate to overexpression of lycopene in a plant (e.g., a tomato plant). Lycopene is a red carotenoid pigment found in plants, particularly tomatoes and tomato products. Lycopene has been identified as a powerful antioxidant that may provide various health benefits. Accordingly, aspects of the present disclosure relate to the overexpression of lycopene in a plant (e.g., a tomato plant) as a means to increase available lycopene in tomatoes and increase accessibility of lycopene to the public.

Lycopene is a key intermediate in the biosynthesis of many carotenoids. Within the larger biosynthetic pathway, geranylgeranyl diphosphate is converted to phytoene via the enzymatic action of phytoene synthase (Psy). Phytoene is then converted to lycopene via the enzymatic action of phytoene dehydrogenase, which is then converted to $\gamma$-carotene and then $\beta$-carotene via the enzymatic action of lycopene cyclase.

Accordingly, aspects of the present disclosure relate to method of enhancing lycopene biosynthesis in a plant (e.g. a tomato plant) by overexpressing enzymes involved in lycopene biosynthesis. In some embodiments, aspects of the present disclosure relate to overexpression of Psy. In some embodiments, a genetic construct expressing Psy is transformed into a plant (e.g., a tomato plant). In some embodiments, a genetic construct expressing Psy is transformed into a plant (e.g., a tomato plant) via *Agrobacterium*-mediated transformation.

Aspects of the present disclosure further relate to methods of downregulating expression of enzymes in a plant (e.g., a tomato plant) that convert lycopene to other products. In some embodiments, lycopene cyclase is downregulated. In some embodiments, gene editing system is used to downregulate expression of enzymes that convert lycopene to other products. In some embodiments, a gene editing system is used to knockdown expression of enzymes that convert lycopene to other products. In some embodiments, a gene editing system is used to knockout expression of enzymes that convert lycopene to other products.

In some embodiments, a gene editing system is a CRISPR/Cas system. In some embodiments, a gene editing system is a CRISPR/Cas9 system. In some embodiments, a gene editing system is a base editing system. In some embodiments, a gene editing system is a prime editing system.

Gene Editing Systems

Aspects of the present disclosure relate to the use of gene editing systems to genetically engineer plants and plant cells (e.g., tomato and eggplant). In some embodiments, gene editing systems are used to integrate any genetic construct or set of genetic constructs of the present disclosure into a plant or plant cell. In some embodiments, gene editing systems are used to upregulate expression of genes that encode enzymes in the lycopene biosynthesis pathway. In some embodiments, gene editing systems are used to upregulate expression of phytoene synthase (Psy) in a plant or plant cell. In some embodiments, gene editing systems are used to downregulate (e.g., knockdown or knockout) genes that encode enzymes within pathways that compete with lycopene biosynthesis.

The term "gene editing systems," as used herein, includes sets of gene editing molecules used for gene editing. Gene editing molecules include molecules that can precisely locate and cut nucleic acids (i.e., DNA) within a cell's genome, enabling modifications to the genome for research and agricultural applications. Non-limiting examples of gene editing molecules include programmable nucleases, guide RNAs (gRNAs), prime editing guide RNAs (pegR-NAs), reverse transcriptases, DNA binding domains, DNA cleavage domains, and effector domains.

In some embodiments, plants or plant cells of the present disclosure further comprise gene editing molecules. In some embodiments, the gene editing molecules are selected from programmable nucleases. In some embodiments, the pro-grammable nucleases are selected from Clustered Regularly Interspaced Short Palindromic Repeats (CRISPR)-Cas nucleases, Transcription Activator-Like Effector Nucleases (TALENs), Zinc Finger Nucleases (ZFNs), and meganucle-ases.

In some embodiments, a gene editing molecule is a programmable nuclease. A "programmable nuclease" includes engineered enzymes that can be used to cut DNA sequences. Non-limiting examples of programmable nucle-ases include Cas nucleases, TALENs, ZFNs, and mega-nucleases.

In some embodiments, a gene editing molecule is a guide RNA (gRNA). A "guide RNA (gRNA)" is a short RNA sequence that directs a Cas nuclease to a specific DNA location for genome editing. In some embodiments, a gene editing molecule is a prime editing guide RNA (pegRNA). A "prime editing guide RNA (pegRNA)" is a specific type of gRNA that directs a Cas nickase to a specific DNA location for genome editing. In some embodiments, a gene editing molecule is a reverse transcriptase. A "reverse tran-scriptase (RT)" is an enzyme that catalyzes the process of reverse transcription, converting RNA into DNA. In some embodiments, a gene editing molecule comprises a DNA binding domain. A "DNA binding domain" is a protein region that specifically recognizes and binds to DNA, often acting as a part of a transcription factor or other DNA-interacting protein. In some embodiments, a gene editing molecule comprises a DNA cleavage domain. A "DNA cleavage domain" is a specific region within a protein (e.g., FokI restriction enzyme or a Cas nuclease) that is respon-sible for cutting or cleaving DNA strands. DNA cleavage domains, often part of larger multi-domain proteins, mediate the enzymatic activity of cutting DNA. In some embodi-ments, a gene editing molecule comprises an effector domain. An "effector domain" is a protein region that mediates the activity of a transcription factor by interacting with other proteins and/or DNA to regulate gene expression, either activating or repressing transcription.

Gene editing molecules are typically part of a larger gene editing system in which two or more components (i.e., gene editing molecules) function in tandem to edit a cell's genome. Non-limiting examples of gene editing examples include a CRISPR-Cas system, a base editing system, a prime editing system, a Transcription Activator-Like Effec-tor Nuclease (TALEN) system, a Zinc Finger Nuclease (ZFN) system, and a Meganuclease system.

CRISPR-Cas Systems

In some embodiments, gene editing molecules comprise a CRISPR-Cas nuclease and a guide RNA (gRNA). In some embodiments the CRISPR-Cas nuclease is a Cas9 nuclease. In some embodiments, the CRISPR-Cas nuclease is a Cas12 nuclease. In some embodiments, the CRISPR-Cas nuclease is a dead Cas9 (dCas9) nuclease.

Aspects of the present disclosure relate to the use of a CRISPR-Cas (Clustered Regularly Interspaced Short Palin-dromic Repeats-CRISPR-associated nuclease) system as a gene editing system. A CRISPR-Cas system is a gene editing system derived from a bacterial immune system, which allows for precise editing of DNA by cutting and/or modi-fying sequences. In some embodiments, a CRISPR-Cas system comprises a Cas nuclease (e.g., Cas9 nuclease), a CRISPR RNA (crRNA), and a trans-activating CRISPR RNA (tracrRNA). In other embodiments, a CRISPR-Cas system comprises a Cas nuclease (e.g., Cas9 nuclease) and an sgRNA, which is an engineered fusion of a crRNA and a tracrRNA. A crRNA includes an RNA sequence comple-mentary to a target DNA and guides the Cas nuclease to the correct genomic target location. A tracrRNA binds to crRNA to stabilize and guide a Cas-crRNA complex. An sgRNA simplifies a CRISPR-Cas system by combining the crRNA and tracrRNA components. The term "gRNA" encompasses any one or more RNA that includes an RNA sequence complementary to a target DNA and is capable of guiding a Cas nuclease to a genomic target location, such as a sgRNA or the combination of a crRNA and a tracrRNA.

A CRISPR-Cas system, in some embodiments, includes a gRNA that recruits a Cas nuclease to a specific site in a cell's genome to generate a double-stranded break (DSB), which can be repaired by two endogenous self-repair mechanisms, the error-prone non-homologous end joining (NHEJ) path-way or the homology-directed repair (HDR) pathway. NHEJ can introduce random insertions or deletions (indels) into the cleavage sites, leading to the generation of frameshift muta-tions or premature stop codons within the open reading frame (ORF) of the target genes, finally inactivating the target gene. Alternatively, HDR can introduce precise genomic modifications at the target site by using a homolo-gous DNA repair template. CRISPR-Cas systems are well-known in the art.

In some embodiments, a CRISPR-Cas system comprises a Cas nuclease. Cas nucleases are enzymes that cut DNA at specific locations. Non-limiting examples of Cas nucleases include Cas9 nucleases, Cas12 nucleases, and CasX and CasY nucleases. In some embodiments, a Cas nuclease is a Cas9 nuclease. Cas9 nucleases include enzymes originally derived from *Streptococcus pyogenes*. In some embodi-ments, a Cas nuclease is a Cas12 nuclease, for example, a Cas12a, Cas12b, Cas12c, Cas12d, Cas12e, Cas12f, or Cas12g nuclease. Cas12a nucleases include enzymes origi-nally derived from *Francisella novicida*. A CRISPR-Cas system that includes a Cas12a nuclease, in some embodi-ments, involves a crRNA for delivery of the Cas12a nuclease to a target sequence. In some embodiments, a Cas nuclease is a dead Cas nuclease (dCas) (e.g., a dead Cas9 (dCas9) nuclease). A "dCas" nuclease is a variant of a Cas nuclease that lacks the DNA-cleaving activity of the Cas nuclease, allowing for targeted gene regulation without causing DNA mutations. In some embodiments, a dCas is a dCas9. Other "dead" Cas nucleases may be used in accordance with the methods and compositions described herein.

Base Editing Systems

Aspects of the present disclosure relate to the use of a base editing system as a gene editing system. A base editing system includes a gene editing system that was developed to improve the efficiency of site-directed mutagenesis. Base editing systems contain a modified Cas nuclease (e.g., a dCas9) coupled with a deaminase, such as a cytosine deami-nase (cytidine base editor; CBE) or adenosine deaminase (adenine base editor; ABE) and can introduce C·G to T·A or A·T to G·C point mutations into an editing window of a gRNA target site without double-stranded DNA cleavage. The term "editing window" includes the specific region on the DNA where Cas-based base editors modify DNA bases. Base editing systems are well-known in the art. For example, see Rees H A, Liu D R. *Nat Rev Genet.* 2018 December; 19 (12): 770-788; Erratum in: *Nat Rev Genet.* 2018 December; 19 (12): 801.

Aspects of the present disclosure relate to the use of a base editing system. A base editing system can include, for example, gene editing molecules that enable precise, single-nucleotide changes in DNA without making double-strand breaks or requiring a donor DNA template. In some embodiments, a base editing system comprises a binding protein, a gRNA (described elsewhere herein), and a deaminase. "Binding protein" includes proteins that selectively binds to another molecule, such as DNA. In some embodiments, a binding protein is a modified Cas protein, for example, a dCas nuclease or a Cas nickase (nCas). In some embodiments, a binding protein is dCas9 nuclease. "Deaminases" include enzymes that remove an amino group from a molecule, typically a nucleotide base. Non-limiting examples of deaminases include cytidine deaminases and adenosine deaminases. In some embodiments, a deaminase includes a cytosine deaminase. In other embodiments, a deaminase includes an adenosine deaminase.

In some embodiments, a cytosine deaminase comprises a cytidine base editor. A cytidine base editor is capable of modifying a single base in DNA without cutting the DNA. In some embodiments, a cytosine deaminase introduces C·G to T·A point mutations into an editing window of a gRNA target site without double-stranded DNA cleavage. In some embodiments a deaminase is an adenosine deaminase. In some embodiments, an adenosine deaminase comprises an adenine base editor. In some embodiments, an adenosine deaminase induces A T to G·C point mutations into an editing window of a gRNA target site without double-stranded DNA cleavage.

Prime Editing Systems

Aspects of the present disclosure relate to the use of a prime editing system as a gene editing system. A prime editing system includes a gene editing system that can mediate targeted insertions, deletions, and all 12 types of base substitutions without double-strand breaks or donor DNA templates. A prime editing system contains a modified Cas nuclease (e.g., a Cas nickase (nCas) that cuts only one DNA strand) fused to a reverse transcriptase and a prime editing gRNA (pegRNA) with functions of specifying a target site and encoding a desired edit. Typically, after a Cas nuclease (e.g., Cas9) cleaves a target site, the reverse transcriptase uses pegRNA as a template for reverse transcription and new genetic information can be written into the target site. Prime editing systems are well-known in the art. For example, see Anzalone, A. V., et al. Nature 576, 149-157 (2019).

In some embodiments, a prime editing system comprises a binding protein, a pegRNA, and a reverse transcriptase. Unlike a standard gRNA, a pegRNA also carries a primer binding site (PBS) and a reverse transcriptase template (RTT), which are necessary for prime editing to occur. A "reverse transcriptase" is an enzyme that copies RNA into DNA, a process called reverse transcription.

In some embodiments, a binding protein is a Cas9 nickase (nCas9). An "nCas9" is a modified version of the Cas9 enzyme that, instead of cutting both strands of DNA, creates a single strand break (a "nick") at the target site. Use of an nCas9 reduces off-target effects and enhances genome editing precision.

TALEN Systems

Aspects of the present disclosure relate to the use of a TALEN (Transcription Activator-Like Effector Nuclease) system as a gene editing system. A TALEN system is a gene editing system that utilizes a TALEN, a type of engineered nuclease derived from bacterial TALE proteins, for precise gene editing. TALE proteins can be designed to target specific DNA sequences for modification. TALENs consist of two parts: a DNA-binding domain derived from bacterial TALE proteins and a DNA-cleaving domain. In some embodiments, a DNA-cleaving domain is a FokI nuclease. The TALE protein domain allows TALENs to bind to specific DNA sequences, while the FokI nuclease creates a double-strand break at that location. TALEN systems are well-known in the art. For example, see Joung J K, Sander J D. TALENs: a widely applicable technology for targeted genome editing. *Nat Rev Mol Cell Biol.* 2013 January; 14 (1): 49-55, the contents of which are herein incorporated by reference in their entirety.

In some embodiments, a TALEN system comprises a designed TALE protein fused to a DNA-cleaving domain. In some embodiments, a DNA-cleaving domain is the cleavage domain of the FokI nuclease.

Zinc Finger Nuclease Systems

Aspects of the present disclosure relate to the use of a zinc finger nuclease system as a gene editing system. A zing finger nuclease system is a gene editing system that utilizes Zinc Finger Nuclease (ZFN) technology. A ZFN is an artificial endonuclease that consists of a designed zinc finger protein (ZFP) fused to the cleavage domain of the FokI restriction enzyme. A ZFN can be redesigned to cleave new targets by developing ZFPs with new sequence specificities. ZFN systems are well-known in the art. For example, see Urnov, F., Rebar, E., Holmes, M. et al. Genome editing with engineered zinc finger nucleases. *Nat Rev Genet* 11, 636-646 (2010), the contents of which are herein incorporated by reference in their entirety.

In some embodiments, a ZFN system comprises a ZFP fused to a DNA-cleaving domain. In some embodiments, a DNA-cleaving domain is the cleavage domain of the FokI nuclease.

Meganuclease Systems

Aspects of the present disclosure relate to the use of a meganuclease system as a gene editing system. A meganuclease system is a gene editing system that utilizes meganucleases. Meganucleases, also known as homing endonucleases, are sequence-specific endonucleases that recognize and cleave long DNA sequences (e.g. about 12 to about 40 base pairs in length). Meganucleases induce double-strand breaks, facilitating homologous recombination for gene targeting and modification. Meganuclease systems are well-known in the art. For example, see Silva G, Poirot L, Galetto R. Smith J, Montoya G, Duchateau P. Pâques F. Meganucleases and other tools for targeted genome engineering: perspectives and challenges for gene therapy. *Curr Gene Ther.* 2011 February; 11 (1): 11-27, the contents of which are herein incorporated by reference in their entirety. In some embodiments, a meganuclease system comprises a meganuclease.

Kits

The genetic constructs described herein may, in some embodiments, be assembled into kits to facilitate their use in research and agricultural applications. A kit may include one or more containers housing the components (e.g., a genetic construct or set of genetic constructs) of the disclosure and instructions for use. Specifically, such kits may include one or more agents described herein, along with instructions describing the intended application and the proper use of these agents. Kits for research purposes may contain the components in appropriate concentrations or quantities for performing various experiments.

The kit may be designed to facilitate use of the methods described herein by researchers and can take many different forms. Each of the compositions of the kit, where applicable, may be provided in liquid form (e.g., in solution), or in solid form (e.g., a dry powder). In certain cases, some of the compositions may be constitutable or otherwise processable (e.g., to an active form), for example, by the addition of a suitable solvent or other medium (for example, water or a cell culture medium), which may or may not be provided in the kit. As used herein, "instructions" can include a component of instruction and/or promotion, and typically involve written instructions on or associated with the packaging. Instructions also can include any oral or electronic instructions provided in any manner such that a user will clearly recognize that the instructions are to be associated with the kit, for example, audiovisual (e.g., videotape, DVD, CD-ROM, website links for downloadable file), internet, and/or web-based communications, etc. The written instructions may be in a form prescribed by a governmental agency regulating the manufacture, use, or sale of biological products, which instructions can also reflect approval by the agency of manufacture, use, or sale for plant administration.

The kit may contain any one or more of the components described herein in one or more containers. As an example, in one embodiment, the kit may include instructions for mixing one or more components of the kit and/or isolating and mixing a sample and applying it to a plant. The kit may include a container housing the compounds described herein. The compounds may be in the form of a liquid, gel, or solid (powder). The compounds may be prepared sterilely, packaged in a syringe, and shipped refrigerated. Alternatively, the compounds may be housed in a vial or other container for storage. A second container may have other agents prepared sterilely. Alternatively, the kit may include the compounds premixed and shipped in a syringe, vial, tube, or other container.

EXAMPLES

In order that the disclosure described in the present application may be more fully understood, the following examples are set forth. The examples described in this application are offered to illustrate the systems and methods provided in this disclosure and are not to be construed in any way as limiting their scope.

Example 1. Genetic Construct Design

This Example relates to a dual-gene construct designed to simultaneously express a heme-producing protein and a male-sterility gene within a single transformation event. A non-limiting example of the dual-gene construct described in this Example is provided by FIG. 3. Genetic constructions used throughout this Examples section are shown in FIGS. 4-7.

The genetic construct described in this Example comprises a heme gene expression cassette, a male sterility expression cassette, and a selectable marker expression cassette.

Heme Gene Expression Cassette

The Heme Gene Expression Cassette described herein includes a promoter, a gene, and a terminator. The promoter is a Cauliflower Mosaic Virus 35S (CaMV 35S) promoter, a strong promoter used to drive constitutive expression of the heme gene in a tomato or eggplant. The gene is the leghemoglobin gene, derived from *Glycine max* (soybean), or functional homolog thereof, for efficient heme production, to introduce desirable meat-like flavor and enhance iron content. The terminator is a Noplaine Synthase (NOS) terminator to ensure proper transcription termination and mRNA stability of the heme gene.

Male Sterility Expression Cassette

The Male Sterility Expression Cassette described herein includes a promoter, a gene, and a terminator. The promoter is an anther-specific promoter, such as TA29 promoter from tobacco, to drive expression of male sterility gene within the anther tissue of the flower. The gene is the barnase gene from *Bacillus amyloliquefaciens* to introduce male sterility by disrupting pollen development. The terminator is a NOS terminator to ensure proper transcription termination and mRNA stability of the barnase gene.

Selectable Marker Cassette

The Selectable Marker Cassette described herein includes the hygromycin phosphotransferase (hpt) gene to confer hygromycin resistance is included within the T-DNA region of the expression cassette to enable selection of successfully transformed plant cells. This gene is regulated by CaMV 35S promoter and utilizes a CaMV 35S polyadenylation (polyA) signal to ensure proper transcript termination and stability. This selectable marker allows for efficient identification and regeneration of transgenic plants on media containing hygromycin.

Example 2. Transformation and Regeneration of Tomato Plants

Transformation of the desired tomato varieties, (including Rutgers, Brandywine, and Marglobe), and/or eggplant varieties (including Black Beauty, Rosa Bianca, and Nadia), may be achieved through *Agrobacterium*-mediated gene transfer. Sterile explants such as cotyledons from young seedlings are co-cultivated with *Agrobacterium tumefaciens* containing the dual-gene construct described in the present disclosure under optimized culture conditions. Following co-cultivation, explants are transferred to selection media containing (i) cefotaxime to eliminate *Agrobacterium* and (ii) hygromycin to allow regeneration of successfully transformed plant tissue. Callus formation is induced used cytokinin-enriched medium, followed by shoot regeneration and root induction. Successfully regenerated transgenic plants are acclimatized under controlled environments before being transferred to the necessary soil or hydroponic systems.

Methods

Seed Germination (0-10 Days);

Tomato seeds were prepared for germination by sterilizing in 20% (v/v) bleach, <0.01% Tween-20, and agitating for 20 min at 250 rpm. Seeds were then rinsed 5 times in distilled water (dH$_2$O), lightly dried, and sown into Murashige and Skoog (MS) medium (2.15 g/L MS Salts, 0.1 g/L myoinositol, 29.2 mM sucrose, 5.93 uM Thiamine-HCl, 4.86 uM Pyridoxine-HCl, 8.12 uM Nicotinic Acid, 8 g/L Agar, pH=5.8). Seeds were incubated for 48-72 hr in dark, and then transferred to photoperiod incubation at 25° C., 16 hr light/8 hr dark.

Cotyledon Explant Preparation (1-3 Days);

Cotyledons that formed 8-day-old seedlings were excised at the petiole, using a sterile blade to cut ~5-10 mm explants. Cotyledons were placed adaxial side down on Preculture Medium, (4.3 g/L MS Salts, 0.1 g/L myoinositol, 1 mL/L Nitsch Vitamins, 20 g/L Sucrose, 5.2 g/L Gelzan-Agar, pH=5.8, 2 mg/L Trans-Zeatin), and incubated for 48 hr in the dark at 19° C.

Agrobacterium-Mediated Transformation

Figure 8:
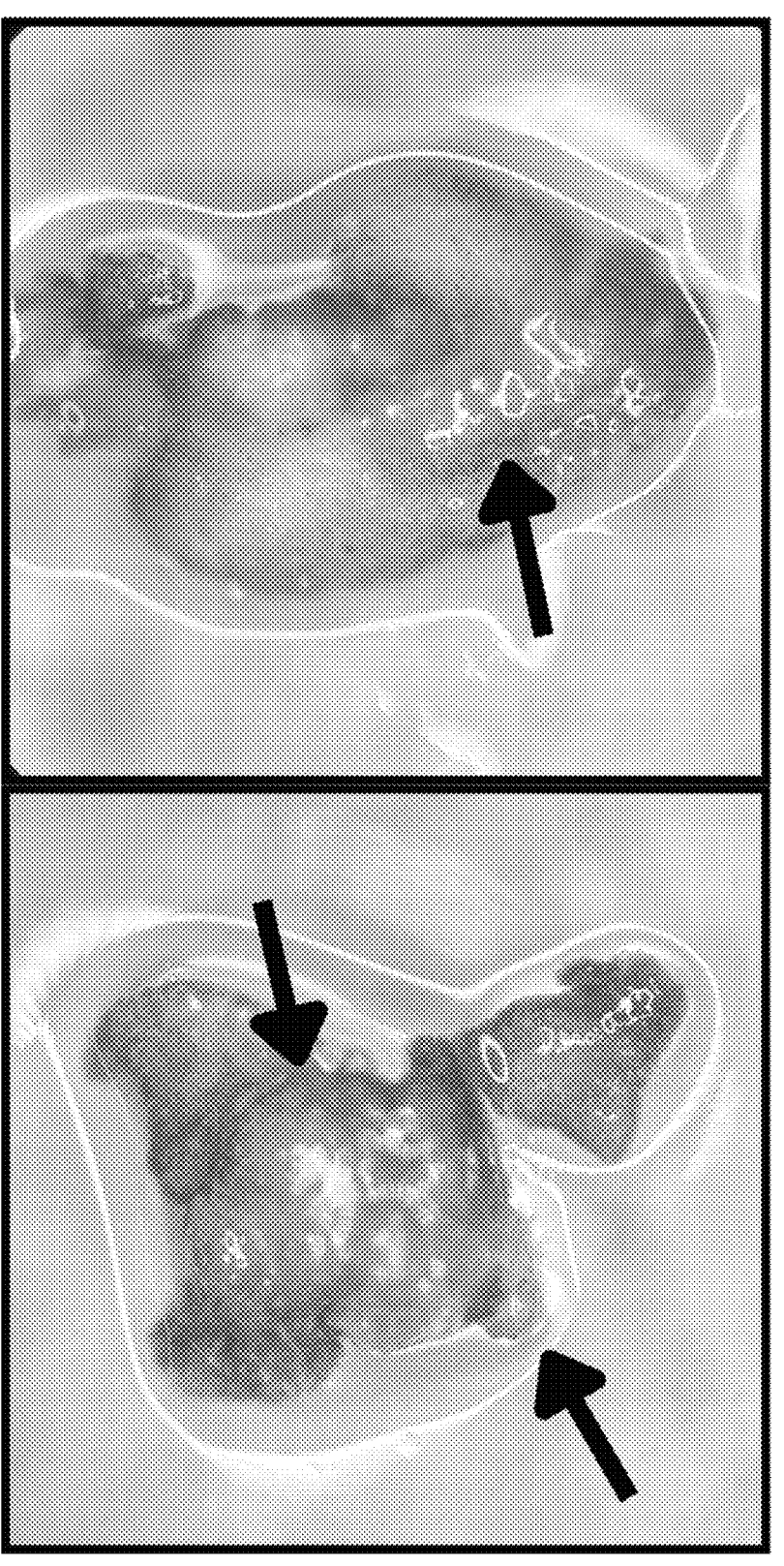
FIG. 8 shows microscope images depicting optimized conditions for tomato regeneration in control cotyledons with callus formation in 4 week cotyledon explants. Arrows point at early callus, characterized by translucent tissue that accumulates on the adaxial side of leaf.

Agrobacterium colonies were inoculated in 50 mL of YEP medium with antibiotic selection according to the plasmid vector used. Cultures were grown to an OD600=0.6-0.8 in 50 mL media, and then pelleted and resuspended into liquid Preculture Medium. Prepared cotyledon explants were incubated with Agrobacterium co-culture for ~20 min with gentle agitation. Explants were then blotted on sterile filter paper and returned to Preculture Medium agar plates, adaxial side down, and incubated for 72 hr in dark conditions at 19° C. Cotyledons were then transferred to fresh Regeneration Media agar plates (Preculture Medium, supplemented with Hygromycin), adaxial side up, and incubated in photoperiod incubator for 10 days. Plates were refreshed every 10-14 days until callus formation and shoot induction. FIG. 8 shows microscope images depicting optimized conditions for tomato regeneration in control cotyledons with callus formation in 4 week cotyledon explants. Arrows point at early callus, characterized by translucent tissue that accumulates on the adaxial side of leaf.

Example 3. Molecular and Phenotype Validation

Transgenic plants are verified at both molecular and phenotypic levels. Genomic DNA is extracted and verified for successful incorporation of both the heme gene and male sterility gene by PCR and amplicon sequencing. Phenotypic outcome is validated by standard chromatography and spectrophotometry techniques to examine increased levels of heme and iron in transgenic plants versus wild-type plants. Male sterility is confirmed by microscopy of anther morphology and pollen viability assays.

Example 4. F1 Hybrid Seed Production

The male-sterile, heme-producing plants (Parental Line A) are used as the female parent in controlled cross-breeding with selected male-fertile plants (Parental Line B). Due to male sterility, Parental Line A cannot self-pollinate, ensuring that all resulting seeds are true F1 hybrids. Seeds are harvested from the crossed plant and used to produce F1 hybrid offspring, and then further characterized by uniform growth, hybrid vigor, and enhanced flavor.

Example 5. Lycopene Enhancement Strategies

This Example relates to approaches for improving lycopene biosynthesis in tomato fruits through genetic or conventional means.

Method 1

Genetic modification can enhance lycopene production by upregulating the expression of major proteins involved in the biosynthesis pathway such as phytoene synthase (Psy), and/or coupled with modification of genes such as phytoene desaturase (Pds) and zeta-catorene desaturase (Zds) to enhance lycopene production. These genes are regulated by the E8 promoter to ensure lycopene overproduction is targeted to the fruit ripening stage. Additionally, competing carotenoid pathway genes may be downregulated to increase metabolic flux toward lycopene accumulation.

Method 2

Crossbreeding high-lycopene public-domain varieties, such as Tangerine or Health Kick tomatoes, with the genetically modified line yields hybrids combining natural lycopene enhancement with high heme content and hybrid vigor.

Example 6. Agronomic Evaluation and Commercial Application

Transgenic and hybrid plants are evaluated under greenhouse and field trials to assess yield, characterize fruit production and quality, and profile the flavor and nutrient content. Data collection and analysis includes wild-type controls to confirm elevated lycopene and iron content.

The genetically engineered male-sterile line simplifies commercial hybrid seed production by eliminating manual emasculation, reducing labor costs, and improving uniformity. Furthermore, the resulting fruit offers a unique flavor profile with nutritional and environmental advantages aligned with the global shift toward plant-based, functional foods.

Additional Embodiments

1. A genetically modified vegetable plant or plant cell comprising:
    a heme gene expression cassette, including a promoter, a
        heme-producing gene, and a first terminator.
2. The plant or cell of Embodiment 1, wherein the vegetable is a tomato or an eggplant.
3. The plant or cell of Embodiment 1 or 2 further including a male sterility gene expression cassette, including an anther-specific promoter, a male sterility gene, and a second terminator.
4. A method of producing a genetically modified vegetable plant or plant cell comprising a step of:
    introducing a genetic construct comprising a heme gene
        and/or a male sterility gene into the plant or cell to
        produce a transformed plant or cell.
5. The method of Embodiment 4, wherein the introducing occurs via Agrobacterium tumefaciens.
6. The method of Embodiment 4 or 5 further comprising selecting and regenerating the transformed plant.
7. The method of any one of Embodiments 4-6 further comprising verifying an expression of both the heme gene and/or the male sterility gene.
8. The method of any one of Embodiments 4-7, wherein the vegetable includes tomato or an eggplant.
9. A method of use of a genetically modified vegetable plant of any one of Embodiments 1-3 as a female parent in the production of F1 hybrid seeds.
10. The method of Embodiment 9, wherein the vegetable includes a tomato or an eggplant.
11. A genetically modified plant (e.g., tomato) wherein a heme gene contained therein includes a leghemoglobin gene from Glycine max and a male sterility gene contained therein includes a barnase gene from Bacillus amyloliquefaciens.
12. The genetically modified plant of Embodiment 11, wherein an anther-specific promoter includes a TA29 promoter from tobacco.
13. A method for producing F1 hybrid seeds comprising steps of:
    (i) crossing a genetically modified plant (e.g., tomato) as
        claimed in claim 2 with a male-fertile plant to produce
        a crossed plant;
    (ii) harvesting seeds from the crossed plant; and
    (iii) planting the seeds to grow F1 hybrid plants.
14. An F1 hybrid plant (e.g., tomato) produced by the method of Embodiment 13, wherein the plant exhibits both heme production and male sterility.

15. A method for enhancing lycopene content in plant fruits (e.g., tomatoes), comprising: introducing a genetic construct that overexpresses the phytoene synthase (Psy) gene under the control of a fruit-specific promoter, thereby increasing lycopene biosynthesis during fruit ripening.

16. A method for increasing lycopene production in plants (e.g., tomatoes), comprising: using CRISPR/Cas9 to knock out genes that compete with the lycopene biosynthesis pathway, ensuring that metabolic precursors are directed towards lycopene production.

17. A method for producing hybrid plants (e.g., tomatoes) with enhanced lycopene content, comprising: crossbreeding public domain high-lycopene varieties to produce hybrids with increased lycopene content and desirable fruit qualities such as large size, flavor, and/or high yield.

18. The method of Embodiment 15, wherein the fruit-specific promoter is the E8 promoter, ensuring lycopene overproduction specifically during the ripening stage.

19. The method of Embodiment 17, wherein the public domain varieties (e.g., tomatoes) are selected from Tangerine, Double Rich, or Health Kick, known for their naturally elevated lycopene content.

EQUIVALENTS

Those skilled in the art will recognize or be able to ascertain using no more than routine experimentation, many equivalents to the specific embodiments of the invention described in the present application. Such equivalents are intended to be encompassed by the following claims. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Such equivalents are intended to be encompassed by the following claims. Also, the phraseology and terminology used in this disclosure is for the purpose of description and should not be regarded as limiting. The use of "including," "comprising," or "having," "containing," "involving," and variations of thereof in this disclosure, is meant to encompass the items listed thereafter and equivalents thereof as well as additional items. As used in this specification and the appended claims, the singular forms "a," "an" and "the" include plural referents unless the content clearly dictates otherwise. All references, including patent documents, are incorporated by reference in their entirety.

What is claimed is:

1. A genetic construct or set of genetic constructs comprising a first promoter operably linked to a first coding sequence and a second promoter operably linked to a second coding sequence, wherein the first coding sequence encodes a heme-producing gene, and wherein the second coding sequence encodes a male-sterility gene, wherein the genetic construct or set of genetic constructs comprises the nucleotide sequence of SEQ ID NO: 3 or SEQ ID NO: 4.

2. A plant cell, comprising the genetic construct or set of genetic constructs of claim 1.

3. The plant cell of claim 2, wherein the plant cell is a tomato plant cell or an eggplant plant cell.

4. A method, the method comprising transforming a plant cell with the genetic construct or set of genetic constructs of claim 1.

5. The method of claim 4, wherein transforming is via *Agrobacterium*-mediated transformation.

6. The method of claim 4, wherein the plant cell is a tomato plant cell or an eggplant plant cell.

7. A method of producing a genetically engineered plant, the method comprising introducing into a plant the genetic construct or set of genetic constructs of claim 1.

8. The method of claim 7, wherein the introducing is via *Agrobacterium*-mediated transformation.

9. The method of claim 7, wherein the genetically engineered plant is a tomato plant or an eggplant plant.

10. A method of producing an F1 hybrid tomato plant, the method comprising:

(i) crossing the genetically engineered plant of claim 7 with a male-fertile tomato plant to produce a crossed plant;

(ii) harvesting seeds from the crossed plant; and (iii) growing the F1 hybrid tomato plant from the seeds.

*    *    *    *    *

SEQUENCE LISTING

```
Sequence total quantity: 16
SEQ ID NO: 1              moltype = DNA   length = 11850
FEATURE                  Location/Qualifiers
source                   1..11850
                         mol_type = other DNA
                         organism = synthetic construct
SEQUENCE: 1
gatctgaggg taaatttcta gtttttctcc ttcattttct tggttaggac ccttttctct   60
ttttattttt ttgagctttg atctttcttt aaactgatct attttttaat tgattggtta   120
tggtgtaaat attacatagc tttaactgat aatctgatta ctttatttcg tgtgtctatg   180
atgatgatga tagttacaga accgacgact cgtccgtcct gtagaaaccc caacccgtga   240
aatcaaaaaa ctcgacggcc tgtgggcatt cagtctggat cgcgaaaact gtggaattga   300
tcagcgttgg tgggaaagcg cgttacaaga aagccgggca attgctgtgc caggcagttt   360
taacgatcag ttcgccgatg cagatattcg taattatgcg ggcaacgtct ggtatcagcg   420
cgaagtcttt ataccgaaag gttgggcagg ccagcgtatc gtgctgcgtt tcgatgcggt   480
cactcattac ggcaaagtgt gggtcaataa tcaggaagtg atggagcatc agggcggcta   540
tacgccattt gaagccgatg tcacgccgta tgttattgcc gggaaaagtg tacgtatcac   600
cgtttgtgtg aacaacgaac tgaactggca gactatcccg ccgggaatgg tgattaccga   660
cgaaaacggc aagaaaaagc agtcttactt ccatgatttc tttaactatg ccggaatcca   720
tcgcagcgta atgctctaca ccacgccgaa cacctgggtg gacgatatca ccgtggtgac   780
gcatgtcgcg caagactgta accacgcgtc tgttgactgg caggtggtgg ccaatggtga   840
tgtcagcgtt gaactgcgtg atgcggatca acaggtggtt gcaactggac aaggcactag   900
cgggactttg caagtggtga atccgcacct ctggcaaccg ggtgaaggtt atctctatga   960
actcgaagtc acagccaaaa gccagacaga gtctgatatc tacccgcttc gcgtcggcat   1020
ccggtcagtg gcagtgaagg gccaacagtt cctgattaac cacaaaccgt tctactttac   1080
tggctttggt cgtcatgaag atgcggactt acgtggcaaa ggattcgata acgtgctgat   1140
ggtgcacgac cacgcattaa tggactggat tggggccaac tcctaccgta cctcgcatta   1200
cccttacgct gaagagatgc tcgactgggc agatgaacat ggcatcgtgg tgattgatga   1260
aactgctgct gtcggctttc agctgtcttt aggcattggt ttcgaagcgc gcaacaagcc   1320
gaaagaactg tacagcgaag aggcagtcaa cggggaaact cagcaagcgc acttacaggc   1380
gattaaagag ctgatagcgc gtgacaaaaa ccacccaagc gtggtgatgt ggagtattgc   1440
caacgaaccg gatacccgtc cgcaaggtgc acgggaatat ttcgcgccac tggcggaagc   1500
aacgcgtaaa ctcgacccga cgcgtccgat cacctgcgtc aatgtaatgt tctgcgacgc   1560
tcacaccgat accatcagcg atctctttga tgtgctgtgc ctgaaccgtt attacggatg   1620
gtatgtccaa agcggcgatt tggaaacggc agagaaggta ctggaaaaag aacttctggc   1680
ctggcaggag aaactgcatc agccgattat catcaccgaa tacggcgtgg atacgttagc   1740
cgggctgcac tcaatgtaca ccgacatgtg gagtgaagag tatcagtgtg catggctgga   1800
tatgtatcac cgcgtctttg atcgcgtcag cgccgtcgtc ggtgaacagg tatggaattt   1860
cgccgatttt gcgacctcgc aaggcatatt gcgcgttggc ggtaacaaga aagggatctt   1920
cactcgcgac cgcaaaccga gtcggcggc ttttctgctg caaaaacgct ggactggcat   1980
gaacttcggt gaaaaaccgc agcagggagg caaacaagct agccaccacc accaccacca   2040
cgtgtgaatt acaggtgacc agctcgaatt tccccgatcg ttcaaacatt tggcaataaa   2100
gtttcttaag attgaatcct gttgccggtc ttgcgatgat tatcatataa tttctgttga   2160
attacgttaa gcatgtaata attaacatgt aatgcatgac gttatttatg agatgggttt   2220
```

-continued

```
ttatgattag agtcccgcaa ttatacattt aatacgcgat agaaaacaaa atatagcgcg  2280
caaactagga taaattatcg cgcgcggtgt catctatgtt actagatcgg gaattaaact  2340
atcagtgttt gacaggatat attggcgggt aaacctaaga gaaaagagcg tttattagaa  2400
taacggatat ttaaaagggc gtgaaaaggt ttatccgttc gtccatttgt atgtgcatgc  2460
caaccacagg gttcccctcg ggatcaaagt actttgatcc aacccctccg ctgctatagt  2520
gcagtcggct tctgacgttc agtgcagccg tcttctgaaa acgacatgtc gcacaagtcc  2580
taagttacgc gacaggctgc cgccctgccc ttttcctggc gttttcttgt cgcgtgtttt  2640
agtcgcataa agtagaatac ttgcgactag aaccggagac attacgccat gaacaagagc  2700
gccgccgctg gcctgctggg ctatgcccgc gtcagcaccg acgaccagga cttgaccagc  2760
caacgggccg aactgcacgc ggccggctgc accaagctgt tttccgagaa gatcaccggc  2820
accaggcgcg accgcccgga gctggccagg atgcttgacc acctacgccc tggcgacgtt  2880
gtgacagtga ccaggctaga ccgcctggcc cgcagcaccc gcgacctact ggacattgcc  2940
gagcgcatcc aggaggccgg cgcgggcctg cgtagcctgg cagagccgtg ggccgacacc  3000
accacgccgg ccggccgcat ggtgttgacc gtgttcgccg gcattgccga gttcgagcgt  3060
tccctaatca tcgaccgcac ccggagcggg cgcgaggccg ccaaggcccg aggcgtgaag  3120
tttggccccc gccctaccct caccccggca cagatcgcgc acgcccgcga gctgatcgac  3180
caggaaggcc gcaccgtgaa agaggcggct gcactgcttg gcgtgcatcg ctcgaccctg  3240
taccgcgcac ttgagcgcag cgaggaagtg acgcccaccg aggccaggcg gcgcggtgcc  3300
ttccgtgagg acgcattgac cgaggccgac gccctggcgg ccgccgagaa tgaacgccaa  3360
gaggaacaag catgaaaccg caccaggacg gccaggacga accgtttttc attaccgaag  3420
agatcgaggc ggagatgatc gcggccgggt acgtgttcga gccgcccgcg cacgtctcaa  3480
ccgtgcggct gcatgaaatc ctggccggtt tgtctgatgc caagctggcg gcctggccgg  3540
ccagcttggc cgctgaagaa accgagcgcc gccgtctaaa aaggtgatgt gtatttgagt  3600
aaaacagctt gcgtcatgcg gtcgctgcgt atatgatgcg atgagtaaat aaacaaatac  3660
gcaagggaa cgcatgaagg ttatcgctgt acttaaccag aaaggcgggt caggcaagac  3720
gaccatcgca acccatctag cccgcgccct gcaactcgcg gggccgatg ttctgttagt  3780
cgattccgat ccccagggca gtgcccgcga ttgggcggcc gtgcgggaag atcaaccgct  3840
aaccgttgtc ggcatcgacc gcccgacgat tgaccgcgac gtgaaggcca tcggccggcg  3900
cgacttcgta gtgatcgacg gagcgcccca ggcggcggac ttggctgtgt ccgcgatcaa  3960
ggcagccgac ttcgtgctga ttccggtgca gccaagccct tacgacatat gggccaccgc  4020
cgacctggtg gagctggtta agcagcgcat tgaggtcacg gatggaaggc tacaagcggc  4080
ctttgtcgtg tcgcgggcga tcaaaggcac gcgcatcggc ggtgaggttg ccgaggcgct  4140
ggccgggtac gagctgccca ttcttgagtc ccgtatcacg cagcgcgtga gctacccagg  4200
cactgccgcc gccggcacaa ccgttcttga atcagaaccc gagggcgacg ctgcccgcga  4260
ggtccaggcg ctggccgctg aaattaaatc aaaactcatt tgagttaatg aggtaaagag  4320
aaaatgagca aaagcacaaa cacgctaagt gccggccgtc cgagcgcacg cagcagcaag  4380
gctgcaacgt tggccagcct ggcagacacg ccagccatga agcgggtcaa ctttcagttg  4440
ccggcggagg atcacaccaa gctgaagatg tacgcggtac gccaaggcaa gaccattacc  4500
gagctgctat ctgaatacat cgcgcagcta ccagagtaaa tgagcaaatg aataaatgag  4560
tagatgaatt ttagcggcta aaggaggcgg catggaaaat caagaacaac caggcaccga  4620
cgccgtggaa tgccccatgt gtggaggaac gggcggttgg ccaggcgtaa gcggctgggt  4680
tgtctgccgg ccctgcaatg gcactggaac ccccaagccc gaggaatcgg cgtgagcggt  4740
cgcaaaccat ccggcccggt acaaatcggc gcggcgctgg gtgatgacct ggtggagaag  4800
ttgaaggccg cgcaggccgc ccagcggcaa cgcatcgagg cagaagcacg ccccggtgaa  4860
tcgtggcaag cggccgctga tcgaatccgc aaagaatccc ggcaaccgcc ggcagccggt  4920
gcgccgtcga ttaggaagcc gcccaagggc gacgagcaac cagatttttt cgttccgatg  4980
ctctatgacg tgggcacccg cgatagtcgc agcatcatgg acgtggccgt tttccgtctg  5040
tcgaagcgtg accgacgagc tggcgaggtg atccgctacg agcttccaga cgggcacgta  5100
gaggtttccg cagggccggc cggcatggcc agtgtgtggg attacgacct ggtactgatg  5160
gcggtttccc atctaaccga atccatgaac cgataccggg aagggaaggg agacaagccc  5220
ggccgcgtgt tccgtccaca cgttgcggac gtactcaagt tctgccggcg agccgatggc  5280
ggaaagcaga aagacgacct ggtagaaacc tgcattcggt taaacaccac gcacgttgcc  5340
atgcagcgta cgaagaaggc caagaacggc cgcctggtga cggtatccga gggtgaagcc  5400
ttgattagcc gctacaagat cgtaaagagc gaaaccgggc ggccggagta catcgagatc  5460
gagctagctg attggatgta ccgcgagatc acagaaggca agaacccgga cgtgctgacg  5520
gttcaccccg attactttt gatcgatccc ggcatcggcc gttttctcta ccgcctggca  5580
cgccgcgccg caggcaaggc agaagccaga tggttgttca agacgatcta cgaacgcagt  5640
ggcagcgccg gagagttcaa gaagttctgt ttcaccgtgc gcaagctgat cgggtcaaat  5700
gacctgccgg agtacgattt gaaggaggag gcggggcagg ctggcccgat cctagtcatg  5760
cgctaccgca acctgatcga gggcgaagca tccgccggtt cctaatgtac ggagcagatg  5820
ctagggcaaa ttgccctagc aggggaaaaa ggtcgaaaag gtctctttcc tgtggatagc  5880
acgtacattg ggaacccaaa gccgtacatt gggaaccgga acccgtacat gggaaccca  5940
aagccgtaca ttgggaaccg gtcacacatg taagtgactg atataaaaga gaaaaaaggc  6000
gattttcg cctaaaactc tttaaaactt attaaaactc cttaaaacg cctgtcctga  6060
gcataactgt ctggccagcg cacagccgaa gagctgcaaa aagcgcctac ccttcggtcg  6120
ctgcgctccc tacgcccgc cgcttcgcgt cggcctatcg cggccgctgg ccgctcaaaa  6180
atggctggcc tacggccagg caatctacca gggcgcggac aagccgcgcc gtcgccactc  6240
gaccgccggc gcccacatca aggcaccctg cctcgcgcgt ttcggtgatg acggtgaaaa  6300
cctctgacac atgcagctcc cggagacggt cacagcttgt ctgtaagcgg atgccgggag  6360
cagacaagcc cgtcagggcg cgtcagcggg tgttggcggg tgtcggggcg cagccatgac  6420
ccagtcacgt agcgatagcg gagtgtatac tggcttaact atgcggcatc agagcagatt  6480
gtactgagag tgcaccatat gcggtgtgaa ataccgcaca gatgcgtaag gagaaaatac  6540
cgcatcaggc gctcttccgc ttcctcgctc actgactcgc tgcgctcggt cgttcggctg  6600
cggcgagcgg tatcagctca ctcaaaggcg gtaatacggt tatccacaga atcaggggat  6660
aacgcaggaa agaacatgtg agcaaaaggc cagcaaaagg ccaggaaccg taaaaaggcc  6720
gcgttgctgg cgtttttcca taggctccgc ccccctgacg agcatcacaa aaatcgacgc  6780
tcaagtcaga ggtggcgaaa cccgacagga ctataaagat accaggcgtt ccccctgga  6840
agctccctcg tgcgctctcc tgttccgacc ctgccgctta ccggatacct gtccgccttt  6900
ctcccttcgg gaagcgtggc gctttctcat agctcacgct gtaggtatct cagttcggtg  6960
```

-continued

```
taggtcgttc gctccaagct gggctgtgtg cacgaacccc ccgttcagcc cgaccgctgc  7020
gccttatccg gtaactatcg tcttgagtcc aacccggtaa gacacgactt atcgccactg  7080
gcagcagcca ctggtaacag gattagcaga gcgaggtatg taggcggtgc tacagagttc  7140
ttgaagtggt ggcctaacta cggctacact agaaggacag tatttggtat ctgcgctctg  7200
ctgaagccag ttaccttcgg aaaaagagtt ggtagctctt gatccggcaa acaaaccacc  7260
gctggtagcg gtggtttttt tgtttgcaag cagcagatta cgcgcagaaa aaaaggatct  7320
caagaagatc ctttgatctt ttctacgggg tctgacgctc agtggaacga aaactcacgt  7380
taagggattt tggtcatgca ttctaggtac taaaacaatt catccagtaa aatataatat  7440
tttattttct cccaatcagg cttgatcccc agtaagtcaa aaaatagctc gacatactgt  7500
tcttccccga tatcctccct gatcgaccgg acgcagaagg caatgtcata ccacttgtcc  7560
gccctgccgc ttctcccaag atcaataaag ccacttactt tgccatcttt cacaaagatg  7620
ttgctgtctc ccaggtcgcc gtgggaaaag acaagttcct cttcgggctt ttccgtcttt  7680
aaaaaatcat acagctcgcg cggatcttta aatggagtgt cttcttccca gtttttcgcaa  7740
tccacatcgg ccagatcgtt attcagtaag taatccaatt cggctaagcg gctgtctaag  7800
ctattcgtat agggacaatc cgatatgtcg atggagtgaa agagcctgat cgcactccgca  7860
tacagctcga taatcttttc agggctttgt tcatcttcat actcttccga gcaaaggacg  7920
ccatcggcct cactcatgag cagattgctc cagccatcat gccgttcaaa gtgcaggacc  7980
tttggaacag gcagctttcc ttccagccat agcatcatgt cctttttcccg ttccacatca  8040
taggtggtcc ctttataccg gctgtccgtc attttttaaat ataggtttttc attttctccc  8100
accagcttat ataccttagc aggagacatt ccttccgtat cttttacgca gcggtatttt  8160
tcgatcagtt ttttcaattc cggtgatatt ctcattttag ccatttatta tttccttcct  8220
cttttctaca gtatttaaag atacccaag aagctaatta taacaagacg aactccaatt  8280
cactgttcct tgcattctaa aaccttaaat accagaaaac agcttttttca aagttgtttt  8340
caaagttggc gtataacata gtatcgacgg agccgatttt gaaaccgcgg tgatcacagg  8400
cagcaacgct ctgtcatcgt tacaatcaac atgctaccct ccgcgagatc atccgtgttt  8460
caaacccggc agcttagttg ccgttcttcc gaatagcatc ggtaacatga gcaaagtctg  8520
ccgccttaca acggctctcc cgctgacgcc gtcccggact gatgggctgc ctgtatcgag  8580
tggtgatttt gtgccgagct gccggtcggg gagctgttgg ctggctggtg gcaggatata  8640
ttgtggtgta aacaaattga cgcttagaca acttaataac acattgcgga cgtttttaat  8700
gtactgaatt aacgccgaat taattcgggg gatctggatt ttagtactgg attttggttt  8760
taggaattag aaattttatt gatagaagta ttttacaaat acaaatacat actaaggggt  8820
tcttatatgc tcaacacatg agcgaaaccc tataggaacc ctaattccct tatctgggaa  8880
ctactcacac attattatgg agaaactcga gcttgtcgat cgacagatcc ggtcggcatc  8940
tactctattt ctttgccctc ggacgagtgc tggggcgtcg gtttccacta tcggcgagta  9000
cttctcacaca gccatcggtc cagacggccg cgcttctgcg ggcgatttgt gtacgcccga  9060
cagtcccggc tccggatcgg acgattgcgt cgcatcgacc ctgcgcccaa gctgcatcat  9120
cgaaattgcc gtcaaccaag ctctgataga gttggtcaag accaatgcgg agcatatacg  9180
cccggagtcg tggcgatcct gcaagctccg gatgcctccg ctcgaagtag cgcgtctgct  9240
gctccataca agccaaccac ggcctccaga agaagatgtt cctttcgacc tattgggaat  9300
ccccgaacat cgcctcgctc cagtcaatga ccgctgttat gcggccattg tccgtcagga  9360
cattgttgga gccgaaatcc gcgtgcacga ggtgccggac ttcggggcag tcctcggccc  9420
aaagcatcag ctcatcgaga gcctgcgcga cggacgcact gacggtgtcg tccatcacag  9480
tttgccagtg atacacatgg ggatcagcaa tcgcgcatat gaaatcacgc catgtagtgt  9540
attgaccgat tccttgcggt ccgaatgggc cgaacccgct cgtctggcta agatcggccg  9600
cagcgatcgc atccatagcc tccgcgaccg gttgtagaac agcgggcagt tcggtttcag  9660
gcaggtcttg caacgtgaca ccctgtgcac ggcgggagat gcaataggtc aggctctcgc  9720
taaactcccc aatgtcaagc acttccggaa tcgggagcgc ggccgatgca aagtgccgat  9780
aaacataacg atctttgtag aaaccatcgg cgcagctatt tacccgcagg acatatccac  9840
gccctcctac atcgaagctg aaagcacgag attcttcgcc ctccgagagc tgcatcaggt  9900
cggagacgct gtcgaacttt tcgatcagaa acttctcgac agacgtcgcg gtgagttcag  9960
gctttttcat atctcattgc cccccgggat ctgcgaaagc tcgagagaga tagatttgta  10020
gagagagact ggtgatttca gcgtgtcctc tccaaatgaa atgaacttcc ttatatagag  10080
gaaggtcttg cgaaggatag tgggattgtg cgtcatccct tacgtcagtg gagatatcac  10140
atcaatccac ttgctttgaa gacgtggttg gaacgtcttc tttttccacg atgctcctcg  10200
tgggtggggg tccatctttg ggaccactgt cggcagagac atcttgaacg atagcctttc  10260
ctttatcgca atgatggcat ttgtaggtgc caccttcctt ttctactgtc cttttgatga  10320
agtgacagat agctgggcaa tggaatccga ggaggtttcc cgatattacc ctttgttgaa  10380
aagtctcaat agccctttgg tcttctgaga ctgtatcttt gatattcttg gagtagacga  10440
gagtgtcgtg ctccaccatg ttatcacatc aatccacttg ctttgaagac gtgggttgaa  10500
cgtcttcttt ttccacgatg ctcctcgtgg gtggggtcc atctttggga ccactgtcgg  10560
cagaggcatc ttgaacgata gcctttcctt tatcgcaatg atggcatttg taggtgccac  10620
cttccttttc tactgtcctt ttgatgaagt gacagatagc tgggcaatgg aatccgagga  10680
ggtttcccga tattaccctt tgttgaaaag tctcaatagc cctttggtct ctgagactg  10740
tatctttgat attcttggag tagacgagag tgtcgtgctc caccatgtta gcaagtgcct  10800
ctagccaata cgcaaaccgc ctctccccgc gcgttggccg attcattaat gcagctggca  10860
cgacaggttt cccgactgga aagcgggcag tgagcgcaac gcaattaatg tgagttagct  10920
cactcattag gcaccccagg ctttacactt tatgcttccg gctcgtatgt tgtgtggaat  10980
tgtgagcgga taacaatttc acacaggaaa cagctatgac catgattacg aattcgagct  11040
cggtacccgg ggatcctcta gagtcgacct gcaggcatgc aagcttggca ctggccgtcg  11100
ttttacaacg tcgtgactgg gaaaaccctg gcgttaccca acttaatcgc cttgcagcac  11160
atccccctt cgccagctgg cgtaatagcg aagaggcccg caccgatcgc ccttcccaac  11220
agttgcgcag cctgaatggc gaatgctaga gcagcttgag cttggatcag attgtcgttt  11280
cccgccttca gtttagcttc atggagtcaa agattcaaat agaggaccta acagaactcg  11340
ccgtaaagac tggcgaacag ttcatacaga tctcttacg actcaatgac aagaagaaaa  11400
tcttcgtcaa catggtggag cacgacacac ttgtctactc caaaaatatc aaagatacag  11460
tctcagaaga ccaaagggca attgagactt ttcaacaaag ggtaatatcc ggaaacctcc  11520
tcggattcca ttgcccagct atctgtcact ttattgtgaa gatagtggaa aaggaaggtg  11580
gctcctacaa atgccatcat tgcgataaag gaaaggccat cgttgaagat gcctctgccg  11640
acagtggtcc caaagatgga cccccaccca cgaggagcat cgtggaaaaa gaagacgttc  11700
```

-continued

```
caaccacgtc ttcaaagcaa gtggattgat gtgatatctc cactgacgta agggatgacg   11760
cacaatccca ctatccttcg caagaccctt cctctatata aggaagttca tttcatttgg   11820
agagaacacg ggggactctt gaccatggta                                     11850

SEQ ID NO: 2              moltype = DNA   length = 10058
FEATURE                   Location/Qualifiers
source                    1..10058
                          mol_type = other DNA
                          organism = synthetic construct
SEQUENCE: 2
agcttgcatg cctgcaggtc gactctagag gatccccggg tacgccaaca tggtggagca   60
cgacactctc gtctactcca agaatatcaa agatacagtc tcagaagacc aaagggctat   120
tgagactttt caacaaaggg taatatcggg aaacctcctc ggattccatt gcccagctat   180
ctgtcacttc atcaaaagga cagtagaaaa ggaaggtggc acctacaaat gccatcattg   240
cgataaagga aaggctatcg ttcaagatgc ctctgccgac agtggtccca aagatggacc   300
cccacccacg aggagcatcg tggaaaaaga agacgttcca accacgtctt caaagcaagt   360
ggattgatgt gaacatggtg gagcacgaca ctctcgtcta ctccaagaat atcaaagata   420
cagtctcaga agaccaaagg gctattgaga cttttcaaca aaggtaata tcgggaaacc   480
tcctcggatt ccattgccca gctatctgtc acttcatcaa aaggacagta gaaaaggaag   540
gtggcaccta caaatgccat cattgcgata aaggaaaggc tatcgttcaa gatgcctctg   600
ccgacagtgg tcccaaagat ggacccccac ccacgaggag catcgtggaa aaagaagacg   660
ttccaaccac gtcttcaaag caagtggatt gatgtgatat ctccactgac gtaagggatg   720
acgcacaatc ccactatcct tcgcaagacc cttcctctat ataaggaagt tcatttcatt   780
tggagaggac acgctgaaat caccagtctc tctctacaaa tctatctctc tcgagctttc   840
gcagatccgg gggcaatga gatatgaaaa agcctgaact caccgcgacg tctgtcgaga   900
agtttctgat cgaaaagttc gacagcgtct ccgacctgac cgagctctcg gagggcgaag   960
aatctcgtgc tttcagcttc gatgtaggag ggcgtggata tgtcctgcgg gtaaatagct   1020
gcgccgatgt tttctacaaa gatcgttatg tttatcggca ctttgcatcg gccgcgctcc   1080
cgattccgga agtgcttgac attggggagt ttagcgagag cctgacctat tgcatctccc   1140
gccgttcaca gggtgtcacg ttgcaagacc tgcctgaaac cgaactgccc gctgttctac   1200
aaccggtcgc ggaggctatg gatgcgatcg ctgcggccga tcttagccag acgagcgggt   1260
tcggcccatt cggaccgcaa ggaatcggtc aatacactac atggcgtgat ttcatatgcg   1320
cgattgctga tccccatgtg tatcactggc aaactgtgat ggacgacacc gtcagtgcgt   1380
ccgtcgcgca ggctctcgat gagctgatgc tttgggccga ggactgcccc gaagtccggc   1440
acctcgtgca cgcggatttc ggctccaaca atgtcctgac ggacaatggc cgcataacag   1500
cggtcattga ctggagcgag gcgatgttcg gggattccca atacgaggtc gccaacatct   1560
tcttctggag gccgtggttg gcttgtatgg agcagcagac gcgctacttc gagcggaggc   1620
atccggagct tgcaggatcg ccacgactcc gggcgtatat gctccgcatt ggtcttgacc   1680
aactctatca gagcttggtt gacggcaatt tcgatgatgc agcttgggcg cagggtcgat   1740
gcgacgcaat cgtccgatcc ggagccggga ctgtcgggcg tacacaaatc gcccgcagaa   1800
gcgcggccgt ctggaccgat ggctgtgtag aagtactcgc cgatagtgga aaccgacgcc   1860
ccagcactcg tccgagggca agaaatagag tagatgccg accgggatct gtcgatcgac   1920
aagctcgagt ttctccataa taatgtgtga gtagttccca gataagggaa ttagggttcc   1980
tatagggttt cgctcatgtg ttgagcatat aagaaaccct tagtatgtat ttgtatttgt   2040
aaaatacttc tatcaataaa atttctaatt cctaaaacca aaatccagta ctaaaatcca   2100
gatccccgg taccgagctc gaattcaatt cggcgttaat tcagtacatt aaaaacgtcc   2160
gcaatgtgtt attaagttgt ctaagcgtca atttgtttac accacaatat atcctgccac   2220
cagccagcca acagctcccc gaccggcagc tcggcacaaa atcaccactc gatacaggca   2280
gcccatcagt ccgggacggc gtcagcggga gagccgttgt aaggcggcag actttgctca   2340
tgttaccgat gctattcgga agaacggcaa ctaagctgcc gggtttgaaa cacggatgat   2400
ctcgcggagg gtagcatgtt gattgtaacg atgacagagc gttgctgcct gtgatcaccg   2460
cggtttcaaa atcggctccg tcgatactat gttatacgcc aactttgaaa acaactttga   2520
aaaagctgtt ttctggtatt taaggtttta gaatgcaagg aacagtgaat tggagttcgt   2580
cttgttataa ttagcttctt ggggtatctt taaatactgt agaaaagagg aaggaaataa   2640
taaatggcta aaatgagaat atcaccggaa ttgaaaaaac tgatcgaaaa ataccgctgc   2700
gtaaaagata cggaaggaat gtctcctgct aaggtatata agctggtggg agaaaatgaa   2760
aacctatatt taaaaatgac ggacagccgg tataaaggga ccaccatga tgtggaacgg   2820
gaaaaggaca tgatgctatg gctggaagga agctgcctg ttccaaaggt cctgcacttt   2880
gaacggcatg atggctggag caatctgctc atgagtgagg ccgatggcgt cctttgctcg   2940
gaagagtatg aagatgaaca aagccctgaa aagattatcg agctgtatgc ggagtgcatc   3000
aggctctttc actccatcga catatcggat tgtccctata cgaatagctt agacagccgc   3060
ttagccgaat tggattactt actgaataac gatctggccg atgtggattg cgaaaactgg   3120
gaagaagaca ctccatttaa agatccgcgc gagctgtatg atttttttaaa gacggaaaag   3180
cccgaagagg aacttgtctt ttcccacggc gacctgggac agcaacat ctttgtgaaa   3240
gatggcaaag taagtggctt tattgatctt gggagaagcg gcaggcgga caagtggtat   3300
gacattgcct tctgcgtccg gtcgatcagg gaggatatcg gggaagaaca gtatggtcag   3360
ctattttttg acttactggg gatcaagcct gattgggaga aaataaaata ttatatttta   3420
ctggatgaat gtgttttagta cctagaatgc atgaccaaaa tcccttaacg tgagttttcg   3480
ttccactgag cgtcagaccc cgtagaaaag atcaaaggat cttcttgaga tccttttttt   3540
ctgcgcgtaa tctgctgctt gcaaacaaaa aaaccaccgc taccagcggt ggtttgtttg   3600
ccggatcaag agctaccaac tctttttccg aaggtaactg gcttcagcag agcgcagata   3660
ccaaatactg tccttctagt gtagccgtag ttaggccacc acttcaagaa ctctgtagca   3720
ccgcctacat acctcgctct gctaatcctg ttaccagtgg ctgctgccag tggcgataag   3780
tcgtgtctta ccgggttgga ctcaagacga tagttaccgg ataaggcgca gcggtcgggc   3840
tgaacggggg gttcgtgcac acagcccagc ttggagcgaa cgacctacac cgaactgaga   3900
tacctacagc gtgagctatg agaaagcgcc acgcttcccg aagggagaaa ggcggacagg   3960
tatccggtaa gcggcaggt cggaacagga gagcgcacga gggagcttcc agggggaaac   4020
gcctggtatc tttatagtcc tgtcgggttt cgccacctct gacttgagcg tcgatttttg   4080
tgatgctcgt caggggggcg gagcctatgg aaaaacgcca gcaacgcggc cttttttacgg   4140
```

-continued

```
ttcctggcct tttgctggcc ttttgctcac atgttctttc ctgcgttatc ccctgattct   4200
gtggataacc gtattaccgc ctttgagtga gctgataccg ctcgccgcag ccgaacgacc   4260
gagcgcagcg agtcagtgag cgaggaagcg gaagagcgcc tgatgcggta ttttctcctt   4320
acgcatctgt gcggtatttc acaccgcata tggtgcactc tcagtacaat ctgctctgat   4380
gccgcatagt taagccagta tacactccgc tatcgctacg tgactgggtc atggctgcgc   4440
cccgacaccc gccaacaccc gctgacgcgc cctgacgggc ttgtctgctc ccggcatccg   4500
cttacagaca agctgtgacc gtctccggga gctgcatgtg tcagaggttt tcaccgtcat   4560
caccgaaacg cgcgaggcag ggtgccttga tgtgggcgcc ggcggtcgag tggcgacggc   4620
gcggcttgtc cgcgccctgg tagattgcct ggccgtaggc cagccatttt tgagcggcca   4680
gcggccgcga taggccgacg cgaagcggcg gggcgtaggg agcgcagcga ccgaagggta   4740
ggcgcttttt gcagctcttc ggctgtgcgc tggccagaca gttatgcaca ggccaggcgg   4800
gtttaagag ttttaataag ttttaaagag ttttaggcgg aaaaatcgcc ttttttctct   4860
tttatatcag tcacttacat gtgtgaccgg ttcccaatgt acggctttgg gttcccaatg   4920
tacgggttcc ggttcccaat gtacggcttt gggttcccaa tgtacgtgct atccacagga   4980
aagagacctt ttcgaccttt ttcccctgct agggcaattt gccctagcat ctgctccgta   5040
cattaggaac cggcggatgc ttcgccctcg atcaggttgc ggtagcgcat gactaggatc   5100
gggccagcct gccccgcctc ctccttcaaa tcgtactccg gcaggtcatt tgacccgatc   5160
agcttgcgca cggtgaaaca gaacttcttg aactctccgg cgctgccact gcgttcgtag   5220
atcgtcttga acaaccatct ggcttctgcc ttgcctgcgg cgcggcgtgc caggcggtag   5280
agaaacggc cgatgccggg atcgatcaaa aagtaatcgg ggtgaaccgt cagcacgtcc   5340
gggttcttgc cttctgtgat ctcgcggtac atccaatcag ctagctcgat ctcgatgtac   5400
tccggccgcc cggtttcgct ctttacgatc ttgtagcggc taatcaaggc ttcaccctcg   5460
gataccgtca ccaggcggcc gttcttggcc ttcttcgtac gctgcatggc aacgtgcgtg   5520
gtgtttaacc gaatgcaggt ttctaccagg tcgtctttct gcttccgcc atcggctcgc   5580
cggcagaact tgagtacgtc cgcaacgtgt ggacggaaca cgcggccggg cttgtctccc   5640
ttcccttccc ggtatcggtt catggattcg gttagatggg aaaccgccat cagtaccagg   5700
tcgtaatccc acacactggc catgccggcc ggccctgcgg aaacctctac gtgcccgtct   5760
ggaagctcgt agcggatcac ctcgccagct cgtcggtcac gcttcgacag acggaaaacg   5820
gccacgtcca tgatgctgcg actatcgcgg gtgcccacgt catagagcat cggaacgaaa   5880
aaatctggtt gctcgtcgcc cttgggcggc ttcctaatcg acggcgacc ggctgccggc   5940
ggttgccggg attctttgcg gattcgatca gcggccgctt gccacgattc accggggcgt   6000
gcttctgcct cgatgcgttg ccgctgggcg gcctgcgcgg ccttcaactt ctccaccagg   6060
tcatcaccca gcgccgcgcc gatttgtacc gggccggatg gtttgcgacc gctcacgccg   6120
attcctcggg cttgggggtt ccagtgccat tgcagggccg gcagcaacc cagccgctta   6180
cgcctggcca accgcccgtt cctccacaca tggggcattc cacggcgtcg gtgcctggtt   6240
gttcttgatt ttccatgccg cctcctttag ccgctaaaat tcatctactc atttattcat   6300
ttgctcattt actctggtag ctgcgcgatg tattcagata gcagctcggt aatggtcttg   6360
ccttggcgta ccgcgtacat cttcagcttg gtgtgatcct ccgccggcaa ctgaaagttg   6420
acccgcttca tggctggcgt gtctgccagg ctggccaacg ttgcagcctt gctgctgcgt   6480
gcgctcggac ggccggcact tagcgtgttt gtgcttttgc tcattttctc tttacctcat   6540
taactcaaat gagttttgat ttaatttcag cggccagcgc ctggacctcg cgggcagcgt   6600
cgccctcggg ttctgattca agaacggttg tgccggcggc ggcagtgcct gggtagctca   6660
cgcgctgcgt gatacgggac tcaagaatgg gcagctcgta cccggccagc gcctcggcaa   6720
cctcaccgcc gatgcgcgtg cctttgatcg cccgcgacac gacaaaggcc gcttgtagcc   6780
ttccatccgt gacctcaatg cgctgcttaa ccagctccac caggtcggcg gtggcccata   6840
tgtcgtaagg gcttggctgc accggaatca gcacgaagtc ggctgccttg atcgcggaca   6900
cagccaagtc cgccgcctgg ggcgctccgt cgatcactac gaagtcgcgc cggccgatgg   6960
ccttcacgtc gcggtcaatc gtcgggcggt cgatgccgac aacggttagc ggttgatctt   7020
cccgcacggc cgcccaatcg cgggcactgc cctggggatc ggaatcgact aacagaacat   7080
cggccccggc gagttgcagg gcgcgggcta gatgggttgc gatggtcgtc ttgcctgacc   7140
cgcctttctg gttaagtaca gcgataacct tcatgcgttc cccttgcgta tttgtttatt   7200
tactcatcgc atcatatacg cagcgaccgc atgacgcaag ctgttttact caaatacaca   7260
tcaccttttt agacggcggc gctcggtttc ttcagcggcc aagctggccg gccaggccgc   7320
cagcttggca tcagacaaac cggccaggat ttcatgcagc cgcacggttg agacgtgcgc   7380
gggcggctcg aacacgtacc cggccgcgat catctccgcc tcgatctctt cggtaatgaa   7440
aaacggttcg tcctggccgt cctggtgcgg tttcatgctt gttcctcttg gcgttcattc   7500
tcggcggccg ccagggcgtc ggcctcggtc aatgcgtcct cacggaaggc accgcgccgc   7560
ctggcctcgg tgggcgtcac ttcctcgctg cgctcaagtg cgcggtacag ggtcgagcga   7620
tgcacgccaa gcagtgcagc cgcctctttc acggtgcggc cttcctggtc gatcagctcg   7680
cgggcgtgcg cgatctgtgc cggggtgagg gtagggcgg ggccaaactt cacgcctcgg   7740
gccttggcgg cctcgcgccc gctccggggt cggtcgatga ttagggaacg ctcgaactcg   7800
gcaatgccgg cgaacacggt caacaccatg cggccgccg gcgtggtggt gtcggccac   7860
ggctctgcca ggctacgcag gcccgcgccg gcctcctgga tgcgctcggc aatgtccagt   7920
aggtcgcggg tgctgcgggc caggcggtct agcctggtca ctgtcacaac ctcgccagga   7980
cgtaggtggt caagcatcct ggccagctcc gggcggtcg gcctggtgcc ggtgatcttc   8040
tcggaaaaca gcttggtgca gccggccgcg tgcagttcgg cccgttggtt ggtcaagtcc   8100
tggtcgtcgg tgctgacgcg ggcatagccc agcaggccag cggcggcgct cttgttcatg   8160
gcgtaatgtc tccggttcta gtcgcaagta ttctacttta tgcgactaaa acacgcgaca   8220
agaaaacgcc aggaaaaggg cagggcggca gcctgtcgcg taacttagga cttgtgcgac   8280
atgtcgtttt cagaagacgg ctgcactgaa cgtcagaagc cgactgcact atagcagcgg   8340
aggggttgga tcaaagtact ttgatcccga ggggaaccct gtggttggca tgcacataca   8400
aatggacgaa cggataaacc ttttcacgcc cttttaaata tccgattatt ctaataaacg   8460
ctctttttctc ttaggtttac ccgccaatat atcctgtcaa acactgatag tttaaaagct   8520
ttcccgatct agtaacatag atgacaccgc gcgcgataat ttatcctagt ttgcgcgcta   8580
tattttgttt tctatcgcgt attaaatgta taattgcggg actctaatca taaaaaccca   8640
tctcataaat aacgtcatgc attacatgtt aattattaca tgcttaacgt aattcaacag   8700
aaattatatg ataatcatcg caagaccggc aacaggattc aatcttaaga aactttattg   8760
ccaaatgttt gaacgatcgg ggaaattcga gctaccactt gtacaagaa agctgggttt   8820
aagccttctt gatagcagca gcgagttcat cgtaagcaac ttcccaagcc ctagacaatt   8880
```

-continued

```
catctgacca tttatcacca acagcagctt taatagtttt aagcaaagct tctttcacaa   8940
caacgaactg aggatctgta acagcctttt gagcatgaac tgaacccaaa gcagcatcag   9000
caacaactgt cccagaagct ttaagctgac cagctgaatc tctcaccaga gcaaaaagct   9060
tttctgcatg tccagtcaac ttaggatttg ttggatcaac accgttagcc aaaaatgaaa   9120
acaaatcctt agcagcagga gctttttcca aaattgatgt gtagaaaacc acagaatatt   9180
gtggaatatt tgccttgaaa gcttcaaatg atgatgaaac aagagcatct tgcttttcag   9240
taaaagcaac catggtggca gcctgctttt ttgtacaaac ttgtcagcgt gtcctctcca   9300
aatgaaatga acttccttat atagaggaag ggtcttgcga aggatagtgg gattgtgcgt   9360
catcccttac gtcagtggag atatcacatc aatccacttg ctttgaagac gtggttggaa   9420
cgtcttcttt ttccacgatg ctcctcgtgg gtgggggtcc atctttggga ccactgtcgg   9480
cagaggcatc ttgaacgata gcctttcctt tatcgcaatg atggcatttg taggtgccac   9540
cttccttttc tactgtcctt ttgatgaagt gacagatagc tgggcaatgg aatccgagga   9600
ggtttcccga tattaccctt tgttgaaaag tctcaatagc cctttggtct tctgagactg   9660
tatctttgat attcttggag tagacgagag tgtcgtgctc caccatgttc acatcaatcc   9720
acttgctttg aagacgtggt tggaacgtct tcttttcca cgatgctcct cgtgggtggg   9780
ggtccatctt tgggaccact gtcggcagag gcatcttgaa cgatagcctt tcctttatcg   9840
caatgatggc atttgtaggt gccaccttcc ttttctactg tccttttgat gaagtgacag   9900
atagctgggc aatggaatcc gaggaggttt cccgatatta ccctttgttg aaaagtctca   9960
atagcccttt ggtcttctga gactgtatct ttgatattct tggagtagac gagagtgtcg  10020
tgctccacca tgttggccaa cttttctata caaagttg                          10058
```

SEQ ID NO: 3          moltype = DNA   length = 15312
FEATURE               Location/Qualifiers
source                1..15312
                      mol_type = other DNA
                      organism = synthetic construct
SEQUENCE: 3

```
agcttgcatg cctgcaggtc gactctagag gatcgacttc aaccttatta gtgaatggac    60
aataaaggtt ataagctcct ttactgtgaa agcccaccag taacatcacc ttgcttatat   120
cattcagctt ctttctagta acatttggaa cgtgtttata acagaaaaaa acccaaaaac   180
tctgaaaaga ctcacacttt tcttatctcc agtccacctc tcaaaaggaa caatttcctt   240
cagcttcttg gttggacacc tgttgagcac atatgctgca gtggcaacag tttctcccca   300
caaagtgtta ggaagcttct tctccttcag catgttcctt gtcatatcaa gcaaagttcg   360
gttttcaaca agaccattat gttgaggagt atatggatca gtcacttcat gctcaattcc   420
attctcttta cagaacttct tgaactctgt agagttatac tcacctccac catcagttct   480
gagaatcttc agaagtctga ccactttatt tctcagcctt gattatgaat ttcttaaatt   540
cagcaaacac ctcgtgtttg aatttttataa gggatcccca tgtcatcctt gtgaactcat   600
ccataaatga cataaagtat tattccctcc tagtgaaagg tttgtaatgg gccacacaca   660
taagaatgca ctactcctaa agcatgtttt gctctttgag ctacttttga tgaaaatgac   720
agtcttggtt gcttcccttt catgcacaca ttacatgact tttttggttt cttaattgta   780
ggaattccac gtaccagttt ctttgaattc aaattcccta agctcctaaa gttcaaatga   840
ccaaatcttt tgttccacaa ctcactttcc ttcacaacac ttgttgcgct aaggcattca   900
gagtctgcag ttttaacatt cgccttgaat gttttactcc ttccatgttc tgactccata   960
atcaacttct gataacagtc atacagcttc aaaagaatgt cattcatggt aactggaaat  1020
cccttttcaa ttaattgacc tacactcatc agattgctct tcatgccaag aacgtaccaa  1080
gacgttctga attaatgcag attttctatt attcataatc actctaacat tccccattcc  1140
tttagcattt agttacttat catcagcaca tctaatctg gttttcttcc tagagtcaaa  1200
atcaaccagc catttcttat ttccagtatg atggtttgaa caaccagtgt ccatatatca  1260
ccagtcttct atagacgcac tatcataact agaagccatt aatagcacat gttcatcatg  1320
gtgctcagat ccttagaatg ttcaattgct acaacgatgt aatcaaactg atgagtaaga  1380
gatctaagta ccttctcaat gatactttcc tcataaagag tttctccatg cgacttcatc  1440
tcatttgtga tcagaatcac tctagagatg tagtcagata acttctcatt gttcttcatg  1500
cttagattct catactgctc acgtagagac tgaagtttca ccttctacac tgatgcatca  1560
ctatcgtagc accacaccag tctgtctcac acaacctttt ccgtcattga atcaacgatt  1620
ttcttaaaca cgttcacatc cacacactga tggatgtaga acaacgcatt ctgatccttc  1680
ttcctcatat cacactgagc atttcttttgc gcatccgttg cattttctag aagtgaagca  1740
taaacttcgt tgatgagatc aagaacatct tgagcaccaa ataacacaca catctgaatc  1800
atccaacgat tccagttgtt gtcgtcgaac aatggnagcn tggtgcacag attcacaacg  1860
atatattata anttttgttt tatgaaattt aagaacaaat ttccattatt cttaaaatgt  1920
ttacacactg atgtagactg caaaaggaat aaagatacaa tttgttcaca ccactcactt  1980
gcgtaaatat aagtgagagt taatgagaaa tactaaaata ccctctaaaa ttatgaatta  2040
attctaacaa tctctaatgt tagtataatc cattaaacac tttgatggca ggtataacaa  2100
gggtgtaagt tagtgtatac atattaggct cttattattt ttatattatc tctgcttttc  2160
ttcttcatgt tctcactaat atgatattat ctcccttccc taattattt atatttatta  2220
gaaaaagagt ttcattttt aaaaatatat taccgtaatt tttcaaaaaa taaaatttaa  2280
atatatttta taaaaaaatt atttaataat ttatttacat taatgcataa atataaataa  2340
atactgtcat ttaatatta accttttaac aataaaattat atttatttaa ttcaactaat  2400
ataagctaag ttatctcatc caaccaatta aaaagatcat ttgaaaatac cttttattt   2460
agttgtggc ggtttcaact gtcaaaaaaa aggaattttt acgacgatat aaatttaaac  2520
cagcaaaaaa ttgaagcagt taagcgaacc aactcatggt atgtggtat atttatcttt  2580
gtcgtttata tcggattcga atctctataa tgatgaaaaa ttaatatcaa actttaaata  2640
agaacgtcat ttatagagcc attttgggaa acacatattt catgtacacg tgattcgcaa  2700
atttccaata actctatata tagccctcct cagtttcatg catttgctca caacataacc  2760
ttccttgaat ctggaaaacg tcacattgct tccgcataat gcggtcagcaa cggctaaaat  2820
ccgcttgaat atgttcacac aagccgctca aaacatgatt gacgccgtat acggaagaac  2880
gccgaaaaac cttactaagg aatttcaata agaagaaaaa tcccggttgg ttcagccggg  2940
gtttatttt cgctagataa aaagtactat ttttaaattc tttctattcc tttctttcgt  3000
tgctgataca atgaaaagga atcagcttca catgatgaaa atgggaggta ttgctttgaa  3060
aaaacgatta tcgtggattt ccgtttgttt actggtgctt gtctccgcgg cggggatgct  3120
```

-continued

```
gttttcaaca gctgccaaaa cggaaacatc ttctcacaag gcacacacag aagcacaggt   3180
tatcaacacg tttgacgggg ttgcggatta tcttcagaca tatcataagc tacctgataa   3240
ttacattaca aaatcagaag cacaagccct cggctgggtg gcatcaaaag ggaaccttgc   3300
agacgtcgct ccgggggaaa gcatcggcgg agacatcttc tcaaacaggg aaggcaaact   3360
cccgggcaaa agcggacgaa catggcgtga agcggatatt aactatacat caggcttcag   3420
aaattcagac cggattcttt actcaagcga ctggctgatt tacaaaacaa cggaccatta   3480
tcagaccttt acaaaaatca gataacgaaa aaaacggctt ccctgcggag gccgtttttt   3540
tcagctttac ataaagtgtg taataaattt ttcttcaaac tctgatcggt caatttcact   3600
ttgctagcca ccaccaccac caccacgtgt gagatcgttc aaacatttgg caataaagtt   3660
tcttaagatt gaatcctgtt gccggtcttg cgatgattat catataattt ctgttgaatt   3720
acgttaagca tgtaataatt aacatgtaat gcatgacgtt atttatgaga tgggttttta   3780
tgattagagt cccgcaatta tacatttaat acgcgataga aaacaaaata tagcgcgcaa   3840
actaggataa attatcgcgc gcggtgtcat ctatgttact agatcccggg tacgccaaca   3900
tggtggagca cgacactctc gtctactcca agaatatcaa agatacagtc tcagaagacc   3960
aaagggctat tgagactttt caacaaaggg taatatcggg aaacctcctc ggattccatt   4020
gcccagctat ctgtcacttc atcaaaagga cagtagaaaa ggaaggtggc acctacaaat   4080
gccatcattg cgataaagga aaggctatcg ttcaagatgc ctctgccgac agtggtccca   4140
aagatggacc cccacccacg aggagcatcg tggaaaaaga agcgttcca accacgtctt   4200
caaagcaagt ggattgatgt gaacatggtg gagcacgaca ctctcgtcta ctccaagaat   4260
atcaaagata cagtctcaga agaccaaagg gctattgaga cttttcaaca aagggtaata   4320
tcgggaaacc tcctcggatt ccattgccca gctatctgtc acttcatcaa aaggacagta   4380
gaaaaggaag gtggcaccta caaatgccat cattgcgata aaggaaaggc tatcgttcaa   4440
gatgcctctg ccgacagtgg tcccaaagat ggacccccac ccacgaggag catcgtggaa   4500
aaagaagacg ttccaaccac gtcttcaaag caagtggatt gatgtgatat ctccactgac   4560
gtaagggatg acgcacaatc ccactatcct tcgcaagacc cttcctctat ataaggaagt   4620
tcatttcatt tggagaggac acgctgaaat caccagtctc tctctacaaa tctatctctc   4680
tcgagctttc gcagatccgg ggggcaatga gatatgaaaa agcctgaact caccgcgacg   4740
tctgtcgaga agtttctgat cgaaaagttc gacagcgtct ccgacctgat gcagctctcg   4800
gagggcgaag aatctcgtgc tttcagcttc gatgtaggag ggcgtggata tgtcctgcgg   4860
gtaaatagct gcgccgatgg tttctacaaa gatcgttatg tttatcggca ctttgcatcg   4920
gccgcgctcc cgattccgga agtgcttgac attggggagt ttagcgagag cctgacctat   4980
tgcatctccc gccgttcaca gggtgtcacg ttgcaagacc tgcctgaaac cgaactgccc   5040
gctgttctac aaccggtcgc ggaggctatg gatgcgatcg ctgcggccga tcttagccag   5100
acgagcgggt tcggcccatt cggaccgcaa ggaatcggtc aatacactac atggcgtgat   5160
ttcatatgcg cgattgctga tccccatgtg tatcactggc aaactgtgat ggacgacacc   5220
gtcagtgcgt ccgtcgcgca ggctctcgat gagctgatgc tttgggccga ggactgcccc   5280
gaagtccggc acctcgtgca cgcggatttc ggctccaaca atgtcctgac ggacaatggc   5340
cgcataacag cggtcattga ctggagcgag gcgatgttcg gggattccca atacgaggtc   5400
gccaacatct tcttctggag ccgtggttgt cttgtatgg agcagcagac gcgctacttc   5460
gagcggagagc atccggagct tgcaggatcg ccacgactcc gggcgtatat gctccgcatt   5520
ggtcttgacc aactctatca gagcttggtt gacggcaatt tcgatgatgc agcttgggcg   5580
cagggtcgat gcgacgcaat cgtccgatcc ggagccggga ctgtcgggcg tacacaaatc   5640
gcccgcagaa gcgcggccgt ctggaccgat ggctgtgtag aagtactcgc cgatagtgga   5700
aaccgacgcc ccagcactcg tccgagggca aagaaataga gtagatgccg accgggatct   5760
gtcgatcgac aagctcgagt ttctccataa taatgtgtga gtagttccca gataagggaa   5820
ttagggttcc tatagggttt cgctcatgtg ttgagcatat aagaaaccct tagtatgtat   5880
ttgtatttgt aaaatacttc tatcaataaa atttctaatt cctaaaacca aaatccagta   5940
ctaaaatcca gatcccccgg taccgagctc gaattcaatt cggcgttaat tcagtacatt   6000
aaaaacgtcc gcaatgtgtt attaagttgt ctaagcgtca atttgtttac accacaatat   6060
atcctgccac cagccagcca acagctcccc gaccggcagc tcggcacaaa atcaccactc   6120
gatacaggca gcccatcagt ccggacaggc gtcagcggga gagccgttgt aaggcggcag   6180
actttgctca tgttaccgat gctattcgga agaacggcaa ctaagctgcc gggtttgaaa   6240
cacgatgat ctcgcggagg gtagcatgtt gattgtaacg atgacagagc gttgctgcct   6300
gtgatcaccg cggtttcaaa atcggctccg tcgatactat gttatacgcc aactttgaaa   6360
acaactttga aaaagctgtt ttctggtatt taaggtttta gaatgcaagg aacagtgaat   6420
tggagttcgt cttgttataa ttagcttctt ggggtatctt taaatactgt agaaaagagg   6480
aaggaaataa taaatggcta aaatgagaat atcaccggaa ttgaaaaaac tgatcgaaaa   6540
ataccgctgc gtaaaagata cggaaggaat gtctcctgct aaggtatata agctggtggg   6600
agaaatgaa aacctatatt taaaaatgac ggacagccgg tataaaggga ccacctatga   6660
tgtggaacgg gaaaaggaca tgatgctatg gctggaagga aagctgcctg ttccaaaggt   6720
cctgcacttt gaacgcatg atggctggag caatctgctc atgagtgagg ccgatggcgt   6780
cctttgctcg aagagtatg aagatgaaca aagccctgaa aagattatcg agctgtatgc   6840
ggagtgcatc aggctctttc actccatcga catatcggat tgtcccctata cgaatagctt   6900
agacaccgc ttagccgaat tggattactt actgaataac gatctggccg atgtggattg   6960
cgaaaactgg gaagaagaca ctccatttaa agatccgcgc gagctgtatg attttttaaa   7020
gacgaaaaag cccgaagagg aacttgtctt ttcccacggc gacctgggag acagcaacat   7080
ctttgtgaaa gatggcaaag taagtggctt tattgatctt gggagaagcg gcagggcgga   7140
caagtggtat gacattgcct tctgcgtccg gtcgatcagg gaggatatcg gggaagaaca   7200
gtatgtcgag ctattttttg acttactggg gatcaaactc gattgggaga aataaaaata   7260
ttatatttta ctggatgaat tgttttagta cctagaatgc atgaccaaaa tcccttaacg   7320
tgagttttcg ttccactgag cgtcagaccc cgtagaaaag atcaaaggat cttcttgaga   7380
tcctttttt ctgcgcgtaa tctgctgctt gcaaacaaaa aaaccaccgc taccagcggt   7440
ggtttgtttg ccggatcaag agctaccaac tctttttccg aaggtaactg gcttcagcag   7500
agcgcagata ccaaatactg tccttctagt gtagccgtag ttaggccacc acttcaagaa   7560
ctctgtagca ccgcctacat acctcgctct gctaatcctg ttaccagtgg ctgctgccag   7620
tggcgataag tcgtgtctta ccgggttgga ctcaagacga tagttaccgg ataaggcgca   7680
gcggtcgggc tgaacggggg gttcgtgcac acagcccagc ttggagcgaa cgacctacac   7740
cgaactgaga tacctacagc gtgagctatg agaaagcgcc acgcttcccg aagggagaaa   7800
ggcggacagg tatccggtaa gcggcagggt cggaacagga gagcgcacga gggagcttcc   7860
```

-continued

```
aggggggaaac gcctggtatc tttatagtcc tgtcgggttt cgccacctct gacttgagcg  7920
tcgatttttg tgatgctcgt caggggggcg gagcctatgg aaaaacgcca gcaacgcggc  7980
ctttttacgg ttcctggcct tttgctggcc ttttgctcac atgttctttc ctgcgttatc  8040
ccctgattct gtggataacc gtattaccgc ctttgagtga gctgataccg ctcgccgcag  8100
ccgaacgacc gagcgcagcg agtcagtgag cgaggaagcg gaagagcgcc tgatgcggta  8160
ttttctcctt acgcatctgt gcggtatttc acaccgcata tggtgcactc tcagtacaat  8220
ctgctctgat gccgcatagt taagccagta tacactccgc tatcgctacg tgactgggtc  8280
atggctgcgc cccgacaccc gccaacaccc gctgacgcgc cctgacgggc ttgtctgctc  8340
ccggcatccg cttacagaca agctgtgacc gtctccggga gctgcatgtg tcagaggttt  8400
tcaccgtcat caccgaaacg cgcgaggcag ggtgccttga tgtgggcgcc ggcggtcgag  8460
tggcgacggc gcggcttgtc cgcgccctgg tagattgcct ggccgtaggc cagccatttt  8520
tgagcggcca gcggccgcga taggccgacg cgaagcggcg gggcgtaggg agcgcagcga  8580
ccgaagggta ggcgcttttt gcagctcttc ggctgtgcgc tggccagaca gttatgcaca  8640
ggccaggcgg gttttaagag ttttaataag ttttaaagag ttttaggcgg aaaaatcgcc  8700
ttttttctct tttatatcag tcacttacat gtgtgaccgg ttcccaatgt acggctttgg  8760
gttcccaatg tacgggttcc ggttcccaat gtacggcttt gggttcccaa tgtacgtgct  8820
atccacagga aagagacctt ttcgaccttt ttcccctgct agggcaattt gccctagcat  8880
ctgctccgta cattaggaac cggcggatgc ttcgccctcg atcaggttgc ggtagcgcat  8940
gactaggatc gggccagcct gccccgcctc ctccttcaaa tcgtactccg gcaggtcatt  9000
tgacccgatc agcttgcgca cggtgaaaca gaacttcttg aactctccgg cgctgccact  9060
gcgttcgtag atcgtcttga acaaccatct ggcttctgcc ttgcctgcgg cgcggcgtgc  9120
caggcggtag agaaaacggc cgatgccggg atcgatcaaa aagtaatcgg ggtgaaccgt  9180
cagcacgtcc gggttcttgc cttctgtgat ctcgcggtac atccaatcag ctagctcgat  9240
ctcgatgtac tccggccgcc cggtttcgct ctttacgatc ttgtagcggc taatcaaggc  9300
ttcaccctcg gataccgtca ccaggcggcc gttcttggcc ttcttcgtac gctgcatggc  9360
aacgtgcgtg gtgtttaacc gaatgcaggt ttctaccagg tcgtctttct gctttccgcc  9420
atcggctcgc cggcagaact tgagtacgtc cgcaacgtgt ggacggaaca cgcggccggg  9480
cttgtctccc ttcccttccc ggtatcggtt catggattcg gttagatggg aaaccgccat  9540
cagtaccagg tcgtaatccc acacactggc catgccggcc ggccctgcgg aaacctctac  9600
gtgcccgtct ggaagctcgt agcggatcac ctcgccagct cgtcggtcac gcttcgacag  9660
acggaaaacg gccacgtcca tgatgctgcg actatcgcgg gtgcccacgt catagagcat  9720
cggaacgaaa aaatctggtt gctcgtcgcc cttgggcggc ttcctaatcg acggcgcacc  9780
ggctgccggc ggttgccggg attctttgcg gattcgatca gcggccgctt gccacggattc  9840
accggggcgt gcttctgcct cgatgcgttg ccgctgggcg gcctcgcgg ccttcaactt  9900
ctccaccagg tcatcaccca gcgccgcgcc gatttgtacc gggcggatg gtttgcgacc  9960
gctcacgccg attcctcggg cttggggggtt ccagtgccat tgcagggccg gcaggcaacc  10020
cagccgctta cgcctggcca accgcccgtt cctccacaca tggggcattc cacggcgtcg  10080
gtgcctggtt gttcttgatt ttccatgccg cctcctttag ccgctaaaat tcatctactc  10140
atttattcat ttgctcattt actctggtag ctgcgcgatg tattcagata gcagctcggt  10200
aatggtcttg ccttggcgta ccgcgtacat cttcagcttg gtgtgatcct ccgccggcaa  10260
ctgaaagttg acccgcttca tggctggcgt gtctgccagg ctggccaacg ttgcagcctt  10320
gctgctgcgt gcgctcggac ggccggcact tagcgtgttt gtgcttttgc tcattttctc  10380
tttacctcat taactcaaat gagttttgat ttaatttcag aggtcagtcg ctggacctcg  10440
cgggcagcgt cgccctcggg ttctgattca agaacggttg tgccggcggc ggcagtgcct  10500
gggtagctca cgcgctgcgt gatacgggac tcaagaatgg gcagctcgta cccggccagc  10560
gcctcggcaa cctcaccgcc gatgcgcgtg cctttgatcg cccgcgacac gacaaaggcc  10620
gcttgtagcc ttccatccgt gacctcaatg cgctgcttaa ccggaatcaa gcacgaagtc  10680
gtggcccata tgtcgtaagg gcttggctgc accggaatca gcacgaagtc ggctgccttg  10740
atcgcggaca cagccaagtc cgccgcctgg ggcgctccgt cgatcactac gaagtcgcgc  10800
cggccgatgg ccttcacgtc gcggtcaatc gtcgggcggt cgatgccgac aacgcggttagc  10860
ggttgatctt cccgcacggc cgcccaatcg cgggcactgc cctggggatc ggaatcgatc  10920
aacagaacat cggccccggc gagttgcagg gcgcgggcta gatgggttgc gatggtcgtc  10980
ttgcctgacc cgcctttctg gttaagtaca gcgataacct tcatgcgttc cccttgcgta  11040
tttgtttatt tactcatcgc atcatatacg cagcgaccgc atgacgcaag ctgtttttact  11100
caaatacaca tcaccttttt agacgcaggc gctcggtttc ttcagcggcc aagctggccg  11160
gccaggccgc cagcttggca tcagacaaac cggccaggat ttcatgcagc cgcacggttg  11220
agacgtgcgc gggcggctcg aacacgtacc cggccgcgat catctccgcc tcgatctctt  11280
cggtaatgaa aaacggttcg tcctggccgt cctggtgcgg tttcatgctt gttcctcttg  11340
gcgttcattc tcggcggccg ccagggcgtc ggcctcggtc aatgcgtcct cacggaaggc  11400
accgcgccgc ctggcctcgg tgggcgtcac ttcctgcctg cgctcaagtg cgcggtacag  11460
ggtcgagcga tgcacgccaa gcagtgcagc cgcctctttc acggtgcggc cttcctggtc  11520
gatcagctcg cgggcgtgcg cgatctgtgc cggggtgagg gtaggcgggg gccaaactt  11580
cacgcctcgg gccttggcgg cctcgcgccc gctccgggtg cggtcgatga ttagggaacg  11640
ctcgaactcg gcaatcaatg cgaacacggt caacaccatg cccgccggcg gcgtggtggt  11700
gtcggcccac ggctctgcca ggctacgcag gcccgcgccg gcctcctgga tgcgctcggc  11760
aatgtccagt aggtcgcggg tgctgcgggc caggcggtct agcctggtca ctgtcacaac  11820
gtcgccaggc cgtaggtggt caagcatcct ggccagctcc gggcggtcgc gcctggtgcc  11880
ggtgatcttc tcggaaaaca gcttggtgca gccggccgcg tgcagttcgg cccgttggtt  11940
ggtcaagtcc tggtcgtcgg tgctgacgcg gcatagccga cggttggcag gcggcggcgt  12000
cttgttcatg gcgtaatgtc tccggttcta gtcgcaagta ttctacttta tgcgactaaa  12060
acacgcgaca agaaaacgcc aggaaaaggg cagggcggca gcctgtcgcg taacttagga  12120
cttgtgcgac atgtcgtttt cagaagacgg ctgcactgaa cgtcagaagc cgactgcact  12180
atagcagcgg agggggttgga tcaaagtact ttgatcccga ggggaaccct gtggttggca  12240
tgcacataca aatggacgaa cggataaacc ttttcacgcc cttttaaata tccgattatt  12300
ctaataaacg ctctttttctc ttaggtttac ccgccaatat atcctgtcaa acactgatag  12360
tttaaaagct ttcccgatct agtaacatag atgacaccgc gcgcgataat ttatcctagt  12420
ttgcgcgcta tattttgttt tctatcgcgt attaaatgta taattgcggg actctaatca  12480
taaaaacccca tctcataaat aacgtcatgc attacatgtt aattattaca tgcttaacgt  12540
aattcaacag aaattatatg ataatcatcg caagaccggc aacaggattc aatcttaaga  12600
```

```
aactttattg ccaaatgttt gaacgatcgg ggaaattcga gctaccactt tgtacaagaa   12660
agctgggttt aagccttctt gatagcagca gcgagttcat cgtaagcaac ttcccaagcc   12720
ctagacaatt catctgacca tttatcacca acagcagctt taatagtttt aagcaaagct   12780
tctttcacaa caacgaactg aggatctgta acagcctttt gagcatgaac tgaacccaaa   12840
gcagcatcag caacaactgt cccagaagct ttaagctgac cagctgaatc tctcaccaga   12900
gcaaaaagct tttctgcatg tccagtcaac ttaggatttg ttggatcaac accgttagcc   12960
aaaaatgaaa acaaatcctt agcagcagga gcttttttcca aaaattgatgt gtagaaaacc   13020
acagaatatt gtggaatatt tgccttgaaa gcttcaaatg atgatgaaac aagagcatct   13080
tgcttttcag taaaagcaac catggtggcg gatcccttct tttgcactgt gaatgattag   13140
aataatttct aaaaatctca atatgaggat gccatattta taatagaata aaataaaatg   13200
tgaacaaaga aagagataaa gtagttcact ttttgaaatc taagagagaa atgggaacaa   13260
gaaagagaca aaagtagttt caaacaaact tctcttctaa gtttagtccc tttttaaaat   13320
atgaaaccca atacgtctga ttaagaatag aaaaatatca aattttcaat ataatttata   13380
ctaatcgttt tgaattttttc atactgatat agtgtacgtt tcatcataac aaccaaaacg   13440
ttgttgtttc acaacaataa tatagtagta gttaatttat tatttagtaa taagtggtcc   13500
taaaaattag ataaaatatta ctatgataat ataaaaatat ttgagtcagt cctaaaaaat   13560
tatttagtat tcatacatga atcaaactaa ttagttaagt gtcaacaatt ggacaagtgg   13620
catggaggtt gtaaaagaat gacataagcc aactgctatt tttatccaaa aaaaagaaga   13680
caacttgaca actacatttc ttttattttt ataaatttac taatatcttc tatgcaaaat   13740
tattcggtgc ctttctaaac tttaaggttt ttatttgatg tacacctaaa ttatatttta   13800
ttttaatcac ttcactgaac ttgtttattc cttcatcata tacacctact cctattatga   13860
ctacaagttg gcaaaagtaa tgatatgaat ttctacttaa ataaataata gtcacctaga   13920
taaattaatt taacaaaaga taaatatcaa accttctcac ctaaaatttt gagcaaaact   13980
tctcactaaa acttgtggac taaacccgaa aatcttcaga aaattaatat ttagtactgg   14040
aaaagtcaga ttaaatgtct gcacaagact ttctattgtt gggaataaac aaattaatat   14100
tggattaaaa tagttgaaat atttaggtaa aatgctacat gtcatttatt cattggaaat   14160
tatttcttaa aatttaaaat tcattattta aaagttattt ttgaaaaagg gccgatttct   14220
gaaattcctt ctaagatagg gtctttctag acgtaaagtt gatctattaa attttaaatt   14280
tatcttaaat tcttacaaag taagtattaa tctttgtttc ctttactatt catttacatt   14340
ttgtcctata tttcgtttaa aatatgtcat atattaaaaa aaattaaaaa ttttactttc   14400
ttttttttacg ttatagctat atgacgtgac aaaaaatcaa ctttcacatg cgcctagtag   14460
acttcaagtt aaaagggggat aatggatact ttgcctatct tttaccatat attttaaaat   14520
ccttaattat taagttttcc aatatctctc accattcatt ttctcctatc atatatttta   14580
ggagtcctta ttaattaagt ttactaataa actttattat atattatagg actcctcaat   14640
tattagttct ctttatgtct ctcatcgtac attttcctct tgtcttattt gttaggacac   14700
ttgaaatttt caaaatatat tttgctttta atatatgaag ttgtgtttga ttgtagtttt   14760
tgtaaatata tttaattttt tgaatttttta ttttctaaaa gaaacataaa atttaaaaga   14820
tttaaaagta tcattaaact attagaaata atatatctat gttgttaaaa atgatggttc   14880
ttaattaact gttttattat aaaatatcag ataattcgtt ttatttacgc aaaagttaag   14940
tgaagtaacg aaaattataaa tcccatagaa tattgtgtat atacttggca catgatgatt   15000
gtaacatcct taattattat taattcatcg aacctattat ttcttcattg tctatgtaca   15060
tttatcctta ataattccac ttcaggattt attagttctt tggttattgg tttaagttta   15120
ttttacaacc aagtgaattg aatttgtcct ccattaatat tttggatt aaaaaataaa   15180
taaatttgct cttatttgta gaaagattta gacttttaaa atattacgtt ttctgactct   15240
tttcttatca aaattggact ctctcacttc cacaaaactt aattacatga acaatatcat   15300
tagggaaagc tt                                                        15312
```

```
SEQ ID NO: 4          moltype = DNA   length = 13908
FEATURE               Location/Qualifiers
source                1..13908
                      mol_type = other DNA
                      organism = synthetic construct
SEQUENCE: 4
agcttgcatg cctgcaggtc gactctagag gatcgacttc aaccttatta gtgaatggac   60
aataaaggtt ataagctcct ttactgtgaa agcccaccag taacatcacc ttgcttatat   120
cattcagctt ctttctagta acatttggaa cgtgtttata acagaaaaaa acccaaaaac   180
tctgaaaaga ctcacacttt tcttatctcc agtccacctc tcaaaaggaa caatttcctt   240
cagcttcttg gttggacacc tgttgagcac atatgctgca gtggcaacag tttctcccca   300
caaagtgtta ggaagcttct tctccttcag catgttcctt gtcatatcaa gcaaagttcg   360
gttttcaaca agaccattat gttgaggagt atatggatca gtcacttcat gctcaattcc   420
attctctttta cagaacttct tgaactctgt agagttatac tcacctccac catcagttcc   480
gagaatcttc agaagtctga ccactttatt tctcagcctt gattatgaat ttcttaaatt   540
cagcaaaacac ctcgtgtttg aatttttataa gggatacca tgtcatcctt gtgaactcat   600
ccataaatga cataaagtat tattccctcc tagtgaaagg tttgtaatgg gccacacaca   660
taagaatgca ctactcctaa agcatgtttt gctctttgag ctactttttga tgaaaatggc   720
agtcttggtt gcttcccttt catgcacaca ttacatgact tttttggttt cttaattgta   780
ggaattccac gtaccagttt ctttgaattc aaattcccta agctcctaaa gttcaaatga   840
ccaaatcttt tgttccacaa ctcactttcc ttcacaacac ttgttgcgct aaggcattca   900
gagtctgcag ttttaacatt cgccttgaat gtttttactcc ttccatgttc tgactccata   960
atcaacttct gataacagtc atacagcttc aaaagaatgt cattcatggt aactggaaat   1020
cccttttcaa ttaattgacc tacactcatc agattgctct tcatgccaag aacgtaccaa   1080
gacgttctga attaatgcag attttctatt attcataatc actctaacat tccccattcc   1140
tttagcattt agttacttat catcagcaca tctaatcttg gttttcttcc tagagtcaaa   1200
atcaaccagc catttcttat ttccagtatg atggtttgaa caaccagtgt ccatatatca   1260
ccagtcttct atagacgcac tatcataact agaagccatt aatagcacat gttcatcatg   1320
gtgctcagat ccttagaatg ttcaattgct acaacgatgt aatcaaactg atgagtaaga   1380
gatcaagta ccttctcaat gatactttcc tcataaagag tttctccatg cgacttcatc   1440
tcatttgtga tcagaatcac tctagagatg tagtcagata acttctcatt gttcttcatg   1500
cttagattct catactgctc acgtagagac tgaagtttca ccttctacac tgatgcatca   1560
```

-continued

```
ctatcgtagc accacaccag tctgtctcac acaacctttt ccgtcattga atcaacgatt   1620
ttcttaaaca cgttcacatc cacacactga tggatgtaga acaacgcatt ctgatccttc   1680
ttcctcatat cacactgagc atttctttgc gcatccgttg cattttctag aagtgaagca   1740
taaacttcgt tgatgagatc aagaacatct tgagcaccaa ataacacaca catctgaatc   1800
atccaacgat tccagttgtt gtcgtcgaac aatggnagcn tggtgcacag attcacaacg   1860
atatattata anttttgttt tatgaaattt aagaacaaat ttccattatt cttaaaatgt   1920
ttacacactg atgtagactg caaaaggaat aaagatacaa tttgttcaca ccactcactt   1980
gcgtaaaatat aagtgagagt taatgagaaa tactaaaata ccctctaaaa ttatgaatta   2040
attctaacaa tctctaatgt tagtataatc cattaaacac tttgatggca ggtataacaa   2100
gggtgtaagt tagtgtatac atattaggct cttattattt ttatattatc tctgcttttc   2160
ttcttcatgt tctcactaat atgatattat ctcccttccc taaattattt atatttatta   2220
gaaaaagagt ttcatttttt aaaaatatat taccgtaatt tttcaaaaaa taaaatttaa   2280
atatatttta taaaaaaatt atttaataat ttatttacat taatgcataa atataaataa   2340
atactgtcat ttaatattta accttttaac aataaaattat atttatttaa ttcaactaat   2400
ataagctaag ttatctcatc caaccaatta aaaagatcat ttgaaaatac ctttttattt   2460
agtttgtggc ggtttcaact gtcaaaaaaa aggaattttt acgacgatat aaatttaaac   2520
cagcaaaaaa ttgaagcagt taagcgaacc aactcatggt atgtggatat atttatcttt   2580
gtcgtttata tcggattcga atctctataa tgatgaaaaa ttaatatcaa acttttaaata   2640
agaacgtcat ttatagagcc atttttgggaa acacatattt catgtacacg tgattcgcaa   2700
atttccaata actctatata tagccctcct cagtttcatg catttgctca caacataacc   2760
ttccttgaat ctggaaaacg tcacattgct tccgcatatc gggtcagcaa cggctaaaat   2820
ccgcttgaat atgttcacac aagccgctca aaacatgatt gacgccgtat acggaagaac   2880
gccgaaaaac cttactaagg aatttcaata agaagaaaaa tcccggttgg ttcagccggg   2940
gtttattttt cgctagataa aaagtactat ttttaaattc tttctattcc tttctttcgt   3000
tgctgataca atgaaaagga atcagcttca catgatgaaa atgggaggta ttgctttgaa   3060
aaaacgatta tcgtggattt ccgtttgttt actggtgctt gtctccgcgg cggggatgct   3120
gttttcaaca gctgccaaaa cggaaacatc ttctcacaag gcacacacag aagcacaggt   3180
tatcaacacg tttgacgggg ttgcggatta tcttcagaca tatcataagc tacctgataa   3240
ttacattaca aaatcagaag cacaagccct cggctgggtg gcatcaaaag ggaaccttgc   3300
agacgtcgct ccggggaaaa gcatcggcgg agacatcttc tcaaacaggg aaggcaaact   3360
cccgggcaaa agcggacgaa catggcgtga agcggatatt aactatacat caggcttcag   3420
aaattcagac cggattcttt actcaagcga ctggctgatt tacaaaacaa cggaccatta   3480
tcagaccttt acaaaaatca gataacgaaa aaaacggctt ccctgcggag gccgtttttt   3540
tcagctttac ataaagtgtg taataaattt ttcttcaaac tctgatcggt caatttcact   3600
ttgctagcca ccaccaccac caccacgtgt gagatcgttc aaacatttgg caataaagtt   3660
tcttaagatt gaatcctgtt gccggtcttg cgatgattat catataattt ctgttgaatt   3720
acgttaagca tgtaataatt aacatgtaat gcatgacgtt atttatgaga tgggttttta   3780
tgattagagt cccgcaatta tacatttaat acgcgataga aaacaaaata tagcgcgcaa   3840
actaggataa attatcgcgc gcggtgtcat ctatgttact agatcccggg tacgccaaca   3900
tggtggagca cgacactctc gtctactcca agaatatcaa agatacagtc tcagaagacc   3960
aaagggctat tgagactttt caacaaaggg taatatcggg aaacctcctc ggattccatt   4020
gcccagctat ctgtcacttc atcaaaagga cagtagaaaa ggaaggtggc acctacaaat   4080
gccatcattg cgataaagga aggctatcg ttcaagatgc ctctgccgac aggtggtccca   4140
aagatggacc cccacccacg aggagcatcg tggaaaaaga agacgttcca accacgtctt   4200
caaagcaagt ggattgatgt gaacatggtg gagcacgaca ctctcgtcta ctccaagaat   4260
atcaaagata cagtctcaga agaccaaagg gctattgaga cttttcaaca aagggtaata   4320
tcgggaaacc tcctcggatt ccattgccca gctatctgtc acttcatcaa aaggacagta   4380
gaaaaggaag gtggcaccta caaatgccat cattgcgata aaggaaaggc tatcgttcaa   4440
gatgcctctg ccgacagtgg tcccaaagat ggacccccac ccacgaggag catcgtggaa   4500
aaagaagacg ttcaaccac gtcttcaaag caagtggatt gatgtgatat ctccactgac   4560
gtaaggatg acgcacaatc ccactatcct tcgcaagacc cttcctctat ataaggaagt   4620
tcatttcatt tggagaggac acgctgaaat caccagtctc tctctacaaa tctatctctc   4680
tcgagctttc gcagatccgg ggggcaatga gatatgaaaa agcctgaact caccgcgacg   4740
tctgtcgaga agtttctgat cgaaaagttc gacagcgtct ccgacctgat gcagctctcg   4800
gagggcgaag aatctcgtgc tttcagcttc gatgtaggag ggcgtggata tgtcctgcgg   4860
gtaaatagct gcgccgatgg tttctacaaa gatcgttatg tttatcggca ctttgcatcg   4920
gccgcgctcc cgattccgga agtgcttgac attggggagt ttagcgagag cctgacctat   4980
tgcatctccc gccgttcaca gggtgtcacg ttgcaagacc tgcctgaaac cgaactgccc   5040
gctgttctac aaccggtcgc ggaggctatg gatgcgatcg ctgcggccga tcttagccag   5100
acgagcgggt tcggcccatt cggaccgcaa ggaatcggtc aatacactac atggcgtgat   5160
ttcatatgcg cgattgctga tccccatgtg tatcactggc aaactgtgat ggacgacacc   5220
gtcagtgcgt ccgtcgcgca ggctctcgat gagctgatgc tttgggccga ggactgcccc   5280
gaagtccggc acctcgtgca cgcggatttc ggctccaaca atgtcctgac ggacaatggc   5340
cgcataacag cggtcattga ctggagcgag gcgatgttcg gggattccca atacgaggtc   5400
gccaacatct tcttctggag gccgtggttg gcttgtatgg agcagcagac gcgctacttc   5460
gagcggaggc atccggagct tgcaggatcg ccacgactcc gggcgtatat gctccgcatt   5520
ggtcttgacc aactctatca gagcttggtt gacggcaatt cgatgatgc agcttgggcg   5580
cagggtcgat gcgacgcaat cgtccgatcc ggagccggga ctgtcgggcg tacacaaatc   5640
gcccgcagaa gcgcggccgt ctggaccgat ggctgtgtag aagtactcgc cgatagtggt   5700
aaccgacgcc ccagcactcg tccgagggca aagaaataga gtagatgccg accgggatct   5760
gtcgatcgac aagctcgagt ttctccataa taatgtgtga gtagttccca gataagggaa   5820
ttagggttcc tatagggttt cgctcatgtg ttgagcatat aagaaaccct tagtatgtat   5880
ttgtatttgt aaaatacttc tatcaataaa atttctaatt cctaaaacca aaatccagta   5940
ctaaaatcca gatccccecgg taccgagctc gaattcaatt cggcgttaat tcagtacatt   6000
aaaaacgtcc gcaatgtgtt attaagttgt ctaagcgtca atttgtttac accacaatat   6060
atcctgccac cagccagcca acagctcccc gaccggcagc tcggcacaaa atcaccactc   6120
gatacaggca gcccatcagt ccgggacggc gtcagcggga gagccgttgt aaggcggcag   6180
actttgctca tgttaccgat gctattcgga agaacggcaa ctaagctgcc gggtttgaaa   6240
cacggatgat ctcgcggagg gtagcatgtt gattgtaacg atgacagagc gttgctgcct   6300
```

-continued

```
gtgatcaccg cggtttcaaa atcggctccg tcgatactat gttatacgcc aactttgaaa   6360
acaactttga aaaagctgtt ttctggtatt taaggtttta gaatgcaagg aacagtgaat   6420
tggagttcgt cttgttataa ttagcttctt ggggtatctt taaatactgt agaaaagagg   6480
aaggaaataa taaatggcta aaatgagaat atcaccggaa ttgaaaaaac tgatcgaaaa   6540
ataccgctgc gtaaaagata cggaaggaat gtctcctgct aaggtatata agctggtggg   6600
agaaaatgaa aacctatatt taaaaatgac ggacagccgg tataaaggga ccacctatga   6660
tgtggaacgg gaaaaggaca tgatgctatg gctggaagga aagctgcctg ttccaaaggt   6720
cctgcacttt gaacggcatg atggctggag caatctgctc atgagtgagg ccgatggcgt   6780
cctttgctcg gaagagtatg aagatgaaca aagccctgaa aagattatcg agctgtatgc   6840
ggagtgcatc aggctctttc actccatcga catatcggat tgtccctata cgaatagctt   6900
agacagccgc ttagccgaat tggattactt actgaataac gatctggccg atgtggattg   6960
cgaaaactgg gaagaagaca ctccatttaa agatccgcgc gagctgtatg attttttaaa   7020
gacggaaaag cccgaagagg aacttgtctt ttcccacgcg gacctgggag acagcaacat   7080
ctttgtgaaa gatggcaaag taagtggctt tattgatctt gggaagaagcg gacgggcgga   7140
caagtggtat gacattgcct tctgcgtccg gtcgatcagg gaggatatcg gggaagaaca   7200
gtatgtcgag ctatttttg acttactggg gatcaagcct gattgggaga aaataaaata   7260
ttatatttta ctggatgaat tgtttttagta cctagaatgc atgaccaaaa tcccttaacg   7320
tgagttttcg ttccactgag cgtcagaccc cgtagaaaag atcaaaggat cttcttgaga   7380
tccttttttt ctgcgcgtaa tctgctgctt gcaaacaaaa aaaccaccgc taccagcggt   7440
ggtttgtttg ccggatcaag agctaccaac tcttttttccg aaggtaactg gcttcagcag   7500
agcgcagata ccaaatactg tccttctagt gtagccgtag ttaggccacc acttcaagaa   7560
ctctgtagca ccgcctacat acctcgctct gctaatcctg ttaccagtgg ctgctgccag   7620
tggcgataag tcgtgtctta ccgggttgga ctcaagacga tagttaccgg ataaggcgca   7680
gcggtcgggc tgaacggggg gttcgtgcac acagcccagc ttggagcgaa cgacctacac   7740
cgaactgaga tacctacagc gtgagctatg agaaagcgcc acgcttcccg aagggagaaa   7800
ggcggacagg tatccggtaa gcggcagggt cggaacagga cgggagcttcc   7860
aggggggaaac gcctggtatc tttatagtcc tgtcgggttt cgccacctct gacttgagcg   7920
tcgatttttg tgatgctcgt caggggggcg gagcctatgg aaaaacgcca gcaacgcggc   7980
cttttttacgg ttcctggcct tttgctggcc ttttgctcac atgttctttc ctgcgttatc   8040
ccctgattct gtggataacc gtattaccgc ctttgagtga gctgataccg ctcgccgcag   8100
ccgaacgacc gagcgcagcg agtcagtgag cgaggaagcg gaagagcgcc tgatgcggta   8160
ttttctcctt acgcatctgt gcggtatttc acaccgcata tggtgcactc tcagtacaat   8220
ctgctctgat gccgcatagt taagccagta tacactccgc tatcgctacg tgactgggtc   8280
atggctgcgc cccgacaccc gccaacaccc gctgacgcgc cctgacgggc ttgtctgctc   8340
ccggcatccg cttacagaca agctgtgacc gtctccggga gctgcatgtg tcagaggttt   8400
tcaccgtcat caccgaaacg cgcgaggcag ggtgccttga tgtgggcgcc ggcggtcgag   8460
tggcgacggc gcggcttgtc cgcgccctgg tagattgcct ggccgtaggc cagccatttt   8520
tgagcggcca gcggccgcga taggccgacg cgaagcggcg gggcgtaggg agcgcagcga   8580
ccgaaggggta ggcgcttttt gcagctcttc ggctgtgcgc tggccagaca gttatgcaca   8640
ggccaggcgg gtttttaagag ttttaataag ttttaaagag ttttaggcgg aaaaatcgcc   8700
tttttttctct tttatatcag tcacttacat gtgtgaccgg ttcccaatgt acggctttgg   8760
gttcccaatg tacgggttcc ggttcccaat gtacggcttt gggttcccaa tgtacgtgct   8820
atccacagga aagagacctt ttcgacctttt ttccccctgct agggcaattt gccctagcat   8880
ctgctccgta cattaggaac cggcggatgc ttcgccctcg atcaggttgc ggtagcgcat   8940
gactaggatc gggccagcct gccccgcctc ctccttcaaa tcgtactccg gcaggtcatt   9000
tgacccgatc agcttgcgca cggtgaaaca gaacttcttg aactctccgg cgctgccact   9060
gcgttcgtag atcgtcttga acaaccatct ggcttctgcc ttgcctgcga gcgggcgtgc   9120
caggcggtag agaaaacggc cgatgccggg atcgatcaaa aagtaatcgg ggtgaaccgt   9180
cagcacgtcc gggttcttgc cttctgtgat ctcgcggtac atccaatcag ctagctcgat   9240
ctcgatgtac tccggccgcc cggtttcgct ctttacgatc ttgtagcggc taatcaaggc   9300
ttcacccctcg gataccgtca ccaggcggcc gttcttggcc ttcttcgtac gctgcatggc   9360
aacgtgcgtg gtgtttaacc gaatgcaggt ttctaccagg tcgtctttct gcttccgcc   9420
atcggctcgc cggcagaact tgagtacgtc cgcaacgtgt ggacggaaca cgcggccggg   9480
cttgtctccc ttcccttccc ggtatcggtt catggattcg gttagatggg aaaccgccat   9540
cagtaccagg tcgtaatccc acacactggc catgccggcc ggccctgcag aaacctctac   9600
gtgcccgtct ggaagctcgt agcggatcac ctcgccagct cgtcggtcac gcttcgacag   9660
acggaaaacg gccacgtcca tgatgctgcg actatcgcgg gtgcccacgt catagagcat   9720
cggaacgaaa aaatctggtt gctcgtcgcc cttgggcggc ttcctaatcg acggcgcacc   9780
ggctgccggc ggttgccggg attctttgcg gattcgatca gcggccgctt gccacgattc   9840
accggggcgt gcttctgcct cgatgcggttg ccgctgggcg gcctgcgcgg ccttcaactt   9900
ctccaccagg tcatcaccca gcgccgcgc gatttgtacc gggccggatg gtttgcgacc   9960
gctcacgccg attcctcggg cttggggggtt ccagtgccat tgcagggccg gcaggcaacc   10020
cagccgctta cgcctggcca accgcccgtt cctccacaca tggggcattc cacggcgtcg   10080
gtgcctggtt gttcttgatt ttccatgccg cctcctttag ccgctaaaat tcatctactc   10140
atttattcat ttgctcattt actctggtag ctgcgcgatg tattcagata gcagctcggt   10200
aatggtcttg ccttggcgta ccgcgtacat cttcagcttg gtgtgatcct ccgcggcaa   10260
ctgaaagttg acccgcttca tggctggcgt gtctgccagg ctggccaacg ttgcagcctt   10320
gctgctgcgt gcgctcggac ggccggcact tagcgtgttt gtgcttttgc tcattttctc   10380
tttacctcat taactcaaat gagttttgat ttaatttcag gcggccagcgc ctgaccctcg   10440
cgggcagcgt cgccctcggg ttctgattca agaacggttg tgccggcggc ggcagtgcct   10500
gggtagctca cgcgctgcgt gatacgggac tcaagaatgg gcagctcgta cccggccagc   10560
gcctcggcaa cctcaccgcc gatgcgcgtg cctttgatcg cccgcgacac gacaaaggcc   10620
gcttgtagcc ttccatccgt gacctcaatg cgctgcttaa ccagctccac caggtcggcg   10680
gtggcccata tgtcgtaagg gcttggctgc accggaatca gcacgaagtc ggctgccttg   10740
atcgcggaca cagccaagtc cgccgcctgg ggcgctccgt cgatcactac gaagtcgcgc   10800
cggccgatgg ccttcacgtc gcggtcaatc gtcgggcggt cgatgccgac aacggttagc   10860
ggttgatctt cccgcacggc cgcccaatcg cgggcactgc cctggggatc ggaatcgact   10920
aacagaacat cggccccggc gagttgcagg gcgcgggcta gatgggttgc gatggtcgtc   10980
ttgcctgacc cgcctttctg gttaagtaca gcgataacct tcatgcgttc cccttgcgta   11040
```

```
tttgtttatt tactcatcgc atcatatacg cagcgaccgc atgacgcaag ctgtttttact  11100
caaatacaca tcacctttt agacggcggc gctcggtttc ttcagcggcc aagctggccg   11160
gccaggccgc cagcttggca tcagacaaac cggccaggat ttcatgcagc cgcacggttg   11220
agacgtgcgc gggcggctcg aacacgtacc cggccgcgat catctccgcc tcgatctctt   11280
cggtaatgaa aaacggttcg tcctggccgt cctggtgcgg tttcatgctt gttcctcttg   11340
gcgttcattc tcggcggccg ccagggcgtc ggcctcggtc aatgcgtcct cacggaaggc   11400
accgcgcgc ctggcctcgg tgggcgtcac ttcctcgctg cgctcaagtg cgcggtacag    11460
ggtcgagcga tgcacgccaa gcagtgcagc cgcctcttc acggtgcggc cttcctggtc    11520
gatcagctcg cgggcgtgcg cgatctgtgc cggggtgagg gtagggcggg ggccaaactt    11580
cacgcctcgg gccttggcgg cctcgcgccc gctccgggtg cggtcgatga ttagggaacg    11640
ctcgaactcg gcaatgccgg cgaacacggt caacaccatg cggccggccg gcgtggtggt    11700
gtcggcccac ggctctgcca ggctacgcag gcccgcgccg gcctcctgga tgcgctcggc    11760
aatgtccagt aggtcgcggg tgctgcgggc caggcggtct agcctggtca ctgtcacaac    11820
gtcgccaggg cgtaggtggt caagcatcct ggccagctcc gggcggtcgc gccggtgcc     11880
ggtgatcttc tcggaaaaca gcttggtgca gccggccgcg tgcagttcgg cccgttggtt    11940
ggtcaagtcc tggtcgtcgg tgctgacgcg ggcatagccc agcaggccag cggcggcgct    12000
cttgttcatg gcgtaatgtc tccggttcta gtcgcaagta ttctacttta tgcgactaaa    12060
acacgcgaca agaaaacgcc aggaaaaggg cagggcggca gcctgtcgcg taacttagga    12120
cttgtgcgac atgtcgtttt cagaagacgg ctgcactgaa cgtcagaagc cgactgcact    12180
atagcagcgg aggggttgga tcaaagtact ttgatcccga ggggaaccct gtggttggca    12240
tgcacataca aatggacgaa cggataaacc tttttcacgcc ctttttaaata tccgattatt   12300
ctaataaacg ctcttttctc ttaggtttac ccgccaatat atcctgtcaa acactgatag    12360
tttaaaagct ttcccgatct agtaacatag atgacaccgc gcgcgataat ttatcctagt    12420
ttgcgcgcta tattttgttt tctatcgcgt attaaatgta taattgcggg actctaatca    12480
taaaaaccca tctcataaat aacgtcatgc attacatgtt aattattaca tgcttaacgt    12540
aattcaacag aaattatatg ataatcatcg caagaccggc aacaggattc aatcttaaga    12600
aactttattg ccaaatgttt gaacgatcgg ggaaattcga gctaccactt tgtacaagaa    12660
agctgggttt aagccttctt gatagcagca gcgagttcat cgtaagcaac ttcccaagcc    12720
ctagacaatt catctgacca tttatcacca acagcagctt taatagtttt aagcaaagct    12780
tctttcacaa caacgaactg aggatctgta acagcctttt gagcatgaac tgaacccaaa    12840
gcagcatcag caacaactgt cccagaagct ttaagctgac cagctgaatc tctcaccaga    12900
gcaaaaagct tttctgcatg tccagtcaac ttaggatttg ttggatcaac accgttagcc    12960
aaaaatgaaa acaaatcctt agcagcagga gcttttttcca aaattgatgt gtagaaaacc    13020
acagaatatt gtggaatatt tgccttgaaa gcttcaaatg atgaac agagagcatct         13080
tgcttttcag taaaagcaac catggtggca gcctgctttt ttgtacaaac ttgtcagcgt    13140
gtcctctcca aatgaaatga acttccttat atagaggaag ggtcttgcga aggatagtgg     13200
gattgtgcgt catcccttac gtcagtggag atatcacatc aatccacttg ctttgaagac    13260
gtggttggaa cgtcttcttt ttccacgatg ctcctcgtgg gtgggggtcc atctttggga    13320
ccactgtcgg cagaggcatc ttgaacgata gcctttcct tatcgcaatg atggcatttg     13380
taggtgccac cttccttttc tactgtcctt ttgatgaagt gacagatagc tgggcaatgg    13440
aatccgagga ggtttcccga tattacccctt tgttgaaaag tctcaatagc cctttggtct    13500
tctgagactg tatctttgat attcttggag tagacgagag tgtcgtgctc caccatgttc    13560
acatcaatcc acttgctttg aagacgtggt tggaacgtct tcttttttcca cgatgctcct   13620
cgtgggtggg ggtccatctt tgggaccact gtcggcagag gcatcttgaa cgatagcctt    13680
tcctttatcg caatgatggc atttgtaggt gccaccttcc ttttctactg tccttttgat    13740
gaagtgacag atagctgggc aatggaatcc gaggaggttt cccgatatta ccctttgttg    13800
aaaagtctca atagccctttt ggtcttctga gactgtatct ttgatattct tggagtagac    13860
gagagtgtcg tgctccacca tgttggcaa ctttttctata caaagttg               13908
```

```
SEQ ID NO: 5                 moltype = DNA  length = 435
FEATURE                      Location/Qualifiers
source                       1..435
                             mol_type = genomic DNA
                             organism = Glycine max
SEQUENCE: 5
atggttgctt ttactgaaaa gcaagatgct cttgtttcat catcatttga agctttcaag    60
gcaaatattc cacaatattc tgtggttttc tacacatcaa ttttggaaaa agctcctgct    120
gctaggatt tgttttcatt tttggctaac ggtgttgatc caacaaatcc taagttgact    180
ggacatgcag aaaagctttt tgctctggtg agagattcag ctggtcagct taaagcttct    240
gggacagttg ttgctgatgc tgctttgggt tcagttcatg tcaaaaggc tgttacagat    300
cctcagttcg ttgttgtgaa agaagctttg cttaaaacta ttaaagctgc tgttggtgat    360
aaatggtcag atgaattgtc tagggcttgg gaagttgctt acgatgaact cgctgctgct    420
atcaagaagg cttaa                                                     435
```

```
SEQ ID NO: 6                 moltype = DNA  length = 333
FEATURE                      Location/Qualifiers
source                       1..333
                             mol_type = genomic DNA
                             organism = Bacillus amyloliquefaciens
SEQUENCE: 6
gcacaggtta tcaacacgtt tgacggggtt gcggattatc ttcagacata tcataagcta    60
cctgataatt acattacaaa atcagaagca caagccctcg gctgggtggc atcaaaaggg    120
aaccttgcag acgtcgctcc ggggaaaagc atcggcggga acatcttctc aaacagggaa    180
ggcaaactcc cgggcaaaag cggacgaaca tggcgtgaag cggatattaa ctatacatca    240
ggcttcagaa attcagaccg gattctttac tcaagcgact ggctgatta caaaacaacg    300
gaccattatc agacctttac aaaaaatcaga taa                                333
```

```
SEQ ID NO: 7                 moltype = DNA  length = 1026
FEATURE                      Location/Qualifiers
```

```
source                    1..1026
                          mol_type = other DNA
                          organism = synthetic construct
SEQUENCE: 7
atgaaaaagc ctgaactcac cgcgacgtct gtcgagaagt ttctgatcga aaagttcgac  60
agcgtctccg acctgatgca gctctcggag ggcgaagaat ctcgtgcttt cagcttcgat  120
gtaggagggc gtggatatgt cctgcgggta aatagctgcg ccgatggttt ctacaaagat  180
cgttatgttt atcggcactt tgcatcggcc gcgctcccga ttccggaagt gcttgacatt  240
ggggagttta gcgagagcct gacctattgc atctcccgcc gttcacaggg tgtcacgttg  300
caagacctgc ctgaaaccga actgcccgct gttctacaac cggtcgcgga ggctatggat  360
gcgatcgctg cggccgatct tagccagacg agcgggttcg cccattcgg accgcaagga  420
atcggtcaat acactacatg gcgtgatttc atatgcgcga ttgctgatcc ccatgtgtat  480
cactggcaaa ctgtgatgga cgacaccgtc agtgcgtccg tcgcgcaggc tctcgatgag  540
ctgatgcttt gggccgagga ctgccccgaa gtccggcacc tcgtgcacgc ggatttcgac  600
tccaacaatg tcctgacgga caatggccgc ataacagcgg tcattgactg gagcgaggcg  660
atgttcgggg attcccaata cgaggtcgcc aacatcttct tctggaggcc gtggttggct  720
tgtatggagc agcagacgcg ctacttcgag cggaggcatc cggagcttgc aggatcgcca  780
cgactccggg cgtatatgct ccgcattggt cttgaccaac tctatcagag cttggttgac  840
ggcaatttcg atgatgcagc ttgggcgcag ggtcgatgcg acgcaatcgt ccgatccgga  900
gccgggactg tcgggcgtac acaaatcgcc cgcagaagcg cggccgtctg gaccgatggc  960
tgtgtagaag tactcgccga tagtggaaac cgacgcccca gcactcgtcc gagggcaaag  1020
aaatag                                                              1026

SEQ ID NO: 8            moltype = DNA  length = 2023
FEATURE                 Location/Qualifiers
source                  1..2023
                        mol_type = other DNA
                        organism = synthetic construct
SEQUENCE: 8
atggtagatc tgagggtaaa tttctagttt ttctccttca ttttcttggt taggacccctt  60
ttctcttttt atttttttga gctttgatct ttctttaaac tgatctatttt tttaattgat  120
tggttatggt gtaaatatta catagcttta actgataatc tgattacttt atttcgtgtg  180
tctatgatga tgatgatagt tacagaaccg acgactcgtc cgtcctgtag aaaccccaac  240
ccgtgaaatc aaaaaactcg acggcctgtg ggcattcagt ctggatcgcg aaaactgtgg  300
aattgatcag cgttggtggg aaagcgcgtt acaagaaagc cgggcaattg ctgtgccagg  360
cagttttaac gatcagttcg ccgatgcaga tattcgtaat tatgcgggca acgtctggta  420
tcagcgcgaa gtctttatac cgaaaggttg ggcaggccag cgtatcgtgc tgcgtttcga  480
tgcggtcact cattacggca aagtgtgggt caataatcag gaagtgatgg agcatcaggg  540
cggctatacg ccatttgaag ccgatgtcac gccgtatgtt attgccggga aaagtgtacg  600
tatcaccgtt tgtgtgaaca acgaactgaa ctggcagact atcccgccgg gaatggtgat  660
taccgacgaa aacggcaaga aaaagcagtc ttacttccat gatttcttta actatgccgg  720
aatccatcgc agcgtaatgc tctacaccac gccgaacacc tgggtggacg atatcaccgt  780
ggtgacgcat gtcgcgcaag actgtaacca cgcgtctgtt gactggagca tggtggccaa  840
tggtgatgtc agcgttgaac tgcgtgatgc ggatcaacag gtggttgcaa ctggacaagg  900
cactagcggg actttgcaag tggtgaatcc gcacctctgg caaccgggtg aaggttatct  960
ctatgaactc gaagtcacag ccaaaagcca gacagagtct gatatctacc cgcttcgcgt  1020
cggcatccgg tcagtggcag tgaagggcca acagttcctg attaaccaca aaccgttcta  1080
ctttactggc tttggtcgtc atgaagatgc ggacttacgt ggcaaaggat tcgataacgt  1140
gctgatggtc cacgaccacg cattaatgga ctggattggg gccaactcct accgtacctc  1200
gcattaccct tacgctgaag agatgctcga ctgggcagat gaacatggca tcgtggtgat  1260
tgatgaaact gctgctgtcg gctttcagct gtctttacgt attggtttcg aagcgggcaa  1320
caagccgaaa gaactgtaca gcgaagaggc agtcaacggg gaaactcagc aagcgcactt  1380
acaggcgatt aaagagctga tagcgcgtga caaaaaccac ccaagcgtgg tgatgtggag  1440
tattgccaac gaaccggata cccgtccgca aggtgcacgg gaatatttcg cgccactggc  1500
ggaagcaacg cgtaaactcg acccgacgcg tccgatcacc tgcgtcaatg taatgttctg  1560
cgacgctcac accgatacca tcagcgatct ctttgatgtg ctgtgcctga accgttatta  1620
cggatggtat gtccaaagcg gcgatttgga aacggcagag aaggtactgg aaaaagaact  1680
tctggcctgg caggagaaac tgcatcagcc gattatcatc accgaatacg gcgtggatac  1740
gttagccggg ctgcactcaa tgtacaccga catgtggagt gaagagtatc agtgtgcatg  1800
gctggatatg tatcaccgcg tctttgatcg cgtcagcgcc gtcgtcggtg aacaggtatg  1860
gaatttcgcc gattttgcga cctcgcaagg catattgcgc gttggcggta acaagaaagg  1920
gatcttcact cgcgaccgca aaccgaagtc ggcggctttt ctgctgcaaa aacgctggac  1980
tggcatgaac ttcggtgaaa aaccgcagca gggaggcaaa caa                    2023

SEQ ID NO: 9            moltype = DNA  length = 677
FEATURE                 Location/Qualifiers
source                  1..677
                        mol_type = genomic DNA
                        organism = Cauliflower mosaic virus
SEQUENCE: 9
tgagactttt caacaaaggg taatatcggg aaacctcctc ggattccatt gcccagctat  60
ctgtcacttc atcaaaagga cagtagaaaa ggaaggtggc acctacaaat gccatcattg  120
cgataaagga aaggctatcg ttcaagatgc ctctgccgac agtggtccca aagatggacc  180
cccacccacg aggagcatcg tggaaaaaga agacgttcca accacgtctt caaagcaagt  240
ggattgatgt gaacatggtg gagcacgaca ctctcgtcta ctccaagaat atcaaagata  300
cagtctcaga agaccaaagg gctattgaga cttttcaaca aagggtaata tcgggaaacc  360
tcctcggatt ccattgccca gctatctgtc acttcatcaa aaggacagta gaaaaggaag  420
gtggcaccta caaatgccat cattgcgata aggaaaggc tatcgttcaa gatgcctctg  480
ccgacagtgg tcccaaagat ggacccccac ccacgaggag catcgtggaa aaagaagacg  540
```

-continued

```
ttccaaccac gtcttcaaag caagtggatt gatgtgatat ctccactgac gtaaggatg   600
acgcacaatc ccactatcct tcgcaagacc cttcctctat ataaggaagt tcatttcatt   660
tggagaggac acgctga                                                  677

SEQ ID NO: 10          moltype = DNA  length = 2203
FEATURE                Location/Qualifiers
source                 1..2203
                       mol_type = genomic DNA
                       organism = Solanum lycopersicum
SEQUENCE: 10
aagctttccc taatgatatt gttcatgtaa ttaagttttg tggaagtgag agagtccaat   60
tttgataaga aaagagtcag aaaacgtaat attttaaaag tctaaatctt tctacaaata   120
agagcaaatt tatttatttt ttaatccaat aaatattaat ggaggacaaa ttcaattcac   180
ttggttgtaa aataaactta aaccaataac caaagaacta ataaatcctg aagtggaatt   240
attaaggata aatgtacata gacaatgaag aaataatagg ttcgatgaat taataataat   300
taaggatgtt acaatcatca tgtgccaagt atatacacaa tattctatgg gatttataat   360
ttcgttactt cacttaactt ttgcgtaaat aaaacgaatt atctgatatt ttataataaa   420
acagttaatt aagaaccatc atttttaaca acatagatat attatttcta atagtttaat   480
gatactttta aatcttttaa attttatgtt tcttttagaa aataaaaatt caaaaaatta   540
aatatattta caaaaactac aatcaaacac aacttcatat attaaaagca aaatatattt   600
tgaaaatttc aagtgtccta acaaataaga caagaggaaa atgtacgatg agagacataa   660
agagaactaa taattgagga gtcctataat atataataaa gtttattagt aaacttaatt   720
attaaggact cctaaaatat atgataggag aaaatgaatg gtgagagata ttggaaaact   780
taataattaa ggattttaaa atatatggta aaagataggc aaagtatcca ttatcccctt   840
ttaacttgaa gtctactagg cgcatgtgaa agttgatttt ttgtcacgtc atatagctat   900
aacgtaaaaa aagaaagtaa aatttttaat tttttttaat atatgacata ttttaaacga   960
aatataggac aaaatgtaaa tgaatagtaa aggaaacaaa gattaatact tactttgtaa   1020
gaatttaaga taaatttaaa atttaataga tcaactttac gtctagaaag accctatctt   1080
agaaggaatt tcagaaatcg gcccttttc aaaaataact tttaaataat gaattttaaa   1140
ttttaagaaa taatttccaa tgaataaatg acatgtagca ttttacctaa atatttcaac   1200
tattttaatc caatattaat ttgtttattc ccaacaatag aaagtcttgt gcagacattt   1260
aatctgactt ttccagtact aaaatattaat tttctgaaga ttttcgggtt tagtccacaa   1320
gttttagtga gaagttttgc tcaaaatttt aggtgagaag gtttgatatt tatctttgt   1380
taaattaatt tatctaggtg actattattt atttaagtag aaattcatat cattactttt   1440
gccaacttgt agtcataata ggagtaggtg tatatgatga aggaataaac aagttcagtg   1500
aagtgattaa aataaaatat aatttaggtg tacatcaaat aaaaaccta aagtttagaa   1560
aggcaccgaa taattttgca tagaagatat tagtaaattt ataaaaataa aagaaatgta   1620
gttgtcaagt tgtcttcttt tttttggata aaaatagcag ttggcttatg tcattctttt   1680
acaacctcca tgccacttgt ccaattgttg acacttaact aattagtttg attcatgtat   1740
gaatactaaa taattttta ggactgactc aaatattttt atattatcat agtaatattt   1800
atctaatttt taggaccact tattactaaa taataaatta actactacta tattattgtt   1860
gtgaaacaac aacgttttgg ttgttatgat gaaacgtaca ctatatcagt atgaaaaatt   1920
caaaacgatt agtataaatt atattgaaaa tttgatattt ttctattctt aatcagacgt   1980
attgggtttc atattttaaa aagggactaa acttagaaga gaagtttgtt tgaaactact   2040
tttgtctctt tcttgttccc atttctctct tagatttcaa aaagtgaact actttatctc   2100
tttctttgtt cacatttat tttattctat tataaatatg gcatcctcat attgagattt   2160
ttagaaatta ttctaatcat tcacagtgca aaagaaggga tcc                     2203

SEQ ID NO: 11          moltype = DNA  length = 2736
FEATURE                Location/Qualifiers
source                 1..2736
                       mol_type = genomic DNA
                       organism = Pisum sativum
SEQUENCE: 11
gacttcaacc ttattagtga atggacaata aaggttataa gctcctttac tgtgaaagcc   60
caccagtaac atcaccttgc ttatatcatt cagcttcttt ctagtaacat ttggaacgtg   120
tttataacag aaaaaaaccc aaaaactctg aaaagactca cactttcttt atctccagtc   180
cacctctcaa aaggaacaat ttccttcagc ttcttggttg gacacctgtt gagcacatat   240
gctgcagtgg caacagtttc tccccacaaa gtgttaggaa gcttcttctc cttcagcatg   300
ttccttgtca tatcaagcaa agttcggttt tcaacaagac cattatgttg aggagtatat   360
ggatcagtca cttcatgctc aattccattc tctttacaga acttcttgaa ctctgtagag   420
ttatactcac ctccaccatc agttctgaga atcttcagaa gtctgaccac tttatttctc   480
agccttgatt atgaatttct taaattcagc aaacacctcg tgtttgaatt ttataaggga   540
tacccatgtc atccttgtga actcatccat aaatgacata agtattatt ccctcctagt   600
gaaaggtttg taatgggcca cacacataag aatgcactac tcctaaagca tgtttttgctc   660
tttgagctac ttttgatgaa aatggcagtc ttggttgctt cccttttcatg cacacattac   720
atgacttttt tggtttctta attgtaggaa ttccacgtac cagtttcttt gaattcaaat   780
tccctaagct cctaaagttc aaatgaccaa atctttttgtt ccacaactca ctttccttca   840
caacacttgt tgcgctaagg cattcagagt ctgcagtttt aacattcgcc ttgaatgttt   900
tactccttcc atgttctgac tccataatca acttctgata acagtcatac agcttcaaaa   960
gaatgtcatt catggtaact ggaaatccct tttcaattaa ttgacctaca ctcatcagat   1020
tgctcttcat gccaagaacg taccaagacg ttctgaatta atgcagattt tctattattc   1080
ataatcactc taacattccc cattcctta gcatttagtt acttatcatc agcacatca   1140
atcttggttt tcttcctaga gtcaaaatca accagccatt tcttatttcc agtatgatgg   1200
tttgaacaac cagtgtccat atatcaccag tcttctatag acgcactatc ataactagaa   1260
gccattaata gcacatgttc atcatggtgc tcagatcctt agaatgttca attgctacaa   1320
cgatgtaatc aaactgatga gtaagagatc taagtacctt ctcaatgata ctttcctcat   1380
aaagagtttc tccatgcgac ttcatctcat ttgtgatcag aatcactcta gagatgtagt   1440
cagataactt ctcattgttc ttcatgctta gattctcata ctgctcacgt agagactgaa   1500
```

-continued

```
gtttcacctt ctacactgat gcatcactat cgtagcacca caccagtctg tctcacacaa   1560
cctttttccgt cattgaatca acgattttct taaacacgtt cacatccaca cactgatgga   1620
tgtagaacaa cgcattctga tccttcttcc tcatatcaca ctgagcattt ctttgcgcat   1680
ccgttgcatt ttctagaagt gaagcataaa cttcgttgat gagatcaaga acatcttgag   1740
caccaaataa cacacacatc tgaatcatcc aacgattcca gttgttgtcg tcgaacaatg   1800
gnagcntggt gcacagaatt caacgatat attataantt ttgttttatg aaatttaaga   1860
acaaatttcc attattctta aaatgtttac acactgatgt agactgcaaa aggaataaag   1920
atacaatttg ttcacaccac tcacttgcgt aaatataagt gagagttaat gagaaatact   1980
aaaataccct ctaaaattat gaattaattc taacaatctc taatgttagt ataatccatt   2040
aaacactttg atggcaggta taacaagggt gtaagttagt gtatacatat taggctctta   2100
ttatttttat attatctctg cttttcttct tcatgttctc actaatatga tattatctcc   2160
cttccctaaa ttatttatat ttattagaaa aagagtttca ttttttaaaa atatattacc   2220
gtaattttc aaaaaataaa atttaaatat attttataaa aaaattattt aataatttat   2280
ttacattaat gcataaatat aaatataac tgtcatttaa tatttaacct tttaacaata   2340
aattatattt atttaattca actaatataa gctaagttat ctcatccaac caattaaaaa   2400
gatcatttga aaataccttt ttatttagtt tgtggcggtt tcaactgtca aaaaaaagga   2460
attttttacga cgatataaat ttaaaccagc aaaaaattga agcagttaag cgaaccaact   2520
catggtatgt ggatatattt atctttgtcg tttatatcgg attcgaatct ctataatgat   2580
gaaaaattaa tatcaaactt taaataagaa cgtcatttat agagccattt tgggaaacac   2640
atatttcatg tacacgtgat tcgcaaattt ccaataactc tatatatagc cctcctcagt   2700
ttcatgcatt tgctcacaac ataaccttcc ttgaat                             2736
```

```
SEQ ID NO: 12         moltype = DNA   length = 864
FEATURE               Location/Qualifiers
source                1..864
                      mol_type = genomic DNA
                      organism = Nicotiana tabacum
SEQUENCE: 12
cttttttggtt agcgaatgca attaatttag acattgtgtt atgttccagt taaccgcttc   60
cctgcacttc tttcaatcta tctctcgata gaaaattgtg atactttgcg acttctatca   120
gaggactttt tgtttttccat gtaacaatct gtcatttcg atggggagat ttgcacaaat   180
aggctatta tgtgtcccaa tttaaatttt aaccccatgt cgatcagaac ttagccacga   240
gcaccagaag tttgatggat atgtgacttt gtcactatcc ggtttactaa tcaagagcta   300
tttttattca aaattggata tctagctaag tataactgga taatttgcat taacagattg   360
aatatagtgc caaacaagaa gggacaattg acttgtcact ttatgaaaga tgattcaaac   420
atgatttttt atgtactaat atatacatcc tactcgaatt aaagcgacat aggctcgaag   480
tatgcacatt tagcaatgta aattaaatca gtttttgaat caagctaaaa gcagacttgc   540
ataaggtggg tggctggact agaataaaca tcttctctag cacagcttca taatgtaatt   600
tccataactg aaatcagggt gagacaaaat tttggtactt tttcctcaca ctaagtccat   660
gtttgcaaca aattaataca tgaaacctta atgttaccct cagattagcc tgctactccc   720
cattttcctc gaaatgctcc aacaaaagtt agttttgcaa gttgttgtgt atgtcttgtg   780
ctctatatat gcccttgtgg tgcaagtgta acagtacaac atcatcactc aaatcaaagt   840
ttttacttaa agaaattagc taaa                                          864
```

```
SEQ ID NO: 13         moltype = DNA   length = 253
FEATURE               Location/Qualifiers
source                1..253
                      mol_type = genomic DNA
                      note = Agrobacterium tumefaciens
                      organism = unidentified
SEQUENCE: 13
gatcgttcaa acatttggca ataaagtttc ttaagattga atcctgttgc cggtcttgcg   60
atgattatca tataatttct gttgaattac gttaagcatg taataattaa catgtaatgc   120
atgacgttat ttatgagatg ggtttttatg attagagtcc cgcaattata catttaatac   180
gcgatagaaa acaaaatata gcgcgcaaac taggataaat tatcgcgcgc ggtgtcatct   240
atgttactag atc                                                      253
```

```
SEQ ID NO: 14         moltype = DNA   length = 175
FEATURE               Location/Qualifiers
source                1..175
                      mol_type = genomic DNA
                      organism = Cauliflower mosaic virus
SEQUENCE: 14
tttctccata ataatgtgtg agtagttccc agataaggga attagggttc ctatagggtt   60
tcgctcatgt gttgagcata taagaaaccc ttagtatgta tttgtatttg taaaatactt   120
ctatcaataa aatttctaat tcctaaaacc aaaatccagt actaaatcc agatc          175
```

```
SEQ ID NO: 15         moltype = DNA   length = 25
FEATURE               Location/Qualifiers
source                1..25
                      mol_type = genomic DNA
                      note = Agrobacterium tumefaciens
                      organism = unidentified
SEQUENCE: 15
gtttacacca caatatatcc tgcca                                          25
```

-continued

```
SEQ ID NO: 16          moltype = DNA   length = 25
FEATURE                Location/Qualifiers
source                 1..25
                       mol_type = genomic DNA
                       note = Agrobacterium tumefaciens
                       organism = unidentified
SEQUENCE: 16
gtttacccgc caatatatcc tgtca                                              25
```